United States Patent
Spees

(10) Patent No.: US 9,913,864 B2
(45) Date of Patent: Mar. 13, 2018

(54) COMPOSITIONS AND METHODS FOR CARDIAC TISSUE REPAIR

(71) Applicant: THE UNIVERSITY OF VERMONT AND STATE AGRICULTURE COLLEGE, Burlington, VT (US)

(72) Inventor: Jeffrey Spees, Colchester, VT (US)

(73) Assignee: THE UNIVERSITY OF VERMONT AND STATE AGRICULTURE COLLEGE, Burlington, VT (US)

( * ) Notice: Subject to any disclaimer, the term of this patent is extended or adjusted under 35 U.S.C. 154(b) by 0 days.

(21) Appl. No.: 14/826,613

(22) Filed: Aug. 14, 2015

(65) Prior Publication Data

US 2016/0067283 A1    Mar. 10, 2016

Related U.S. Application Data

(60) Division of application No. 13/220,555, filed on Aug. 29, 2011, now Pat. No. 9,132,155, which is a continuation-in-part of application No. PCT/US2010/001540, filed on May 26, 2010.

(60) Provisional application No. 61/181,071, filed on May 26, 2009.

(51) Int. Cl.

| | |
|---|---|
| *C12N 5/077* | (2010.01) |
| *A61K 35/34* | (2015.01) |
| *A61K 38/18* | (2006.01) |
| *A61K 38/30* | (2006.01) |
| *C12N 5/071* | (2010.01) |
| *A61K 38/19* | (2006.01) |

(52) U.S. Cl.
CPC .......... *A61K 35/34* (2013.01); *A61K 38/1833* (2013.01); *A61K 38/1866* (2013.01); *A61K 38/195* (2013.01); *A61K 38/30* (2013.01); *C12N 5/069* (2013.01); *C12N 5/0657* (2013.01); *C12N 2501/10* (2013.01); *C12N 2501/105* (2013.01); *C12N 2501/12* (2013.01); *C12N 2501/165* (2013.01); *C12N 2502/00* (2013.01)

(58) Field of Classification Search
None
See application file for complete search history.

(56) References Cited

U.S. PATENT DOCUMENTS

| | | | |
|---|---|---|---|
| 7,745,113 B2 | 6/2010 | Evans et al. | |
| 2003/0054973 A1* | 3/2003 | Anversa | A61K 38/18 514/1 |
| 2003/0232431 A1* | 12/2003 | Law | C12N 5/0657 435/366 |
| 2008/0241111 A1 | 10/2008 | Oh et al. | |
| 2009/0081170 A1 | 3/2009 | Riley | |
| 2011/0110897 A1 | 5/2011 | Schwarz et al. | |

FOREIGN PATENT DOCUMENTS

WO    2009045370    4/2009

OTHER PUBLICATIONS

International Search Report in corresponding Application No. PCT/US2010/001540, dated May 26, 2010.
Kabota et al., "Concentrations of Hepatocyte Growth Factor, Basic Fibroblast Growth Factor, and Vascular Endothelial Growth Factor in Pericardial fluid and Plasma," JPN Heart J., vol. 45, No. 6, pp. 989-998 (2004).
Messina et al., Circ. Res., vol. 95(9), pp. 911-921 (2004).
Nakamura et al., "A synthetic small molecule, ONO-1301, enhances endogenous growth factor expression and augments angiogenesis in the ischaemic heart," Clinical Science, 112, pp. 607-616 (2007).
Winter et al., "Epicardium-derived cells in cardiogenesis and cardiac regeneration," Cell. Mol. Life Sci., vol. 64, pp. 692-703 (2007).

* cited by examiner

*Primary Examiner* — Daniel C Gamett
(74) *Attorney, Agent, or Firm* — Melissa Hunter-Ensor; Elbert Chiang; Greenberg Traurig, LLP

(57) ABSTRACT

The invention features compositions comprising agents having cardiac protective activity isolated from epicardial progenitor cells and derivatives thereof, and methods for the use of such compositions.

4 Claims, 42 Drawing Sheets

FIG. 3A
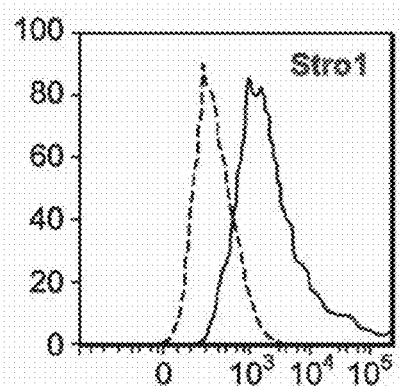
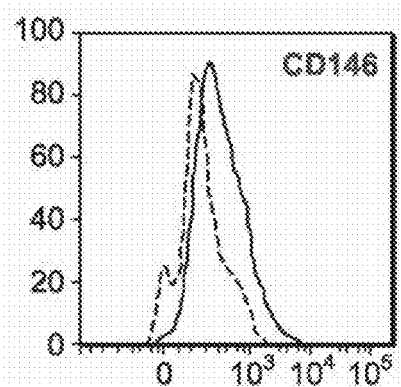
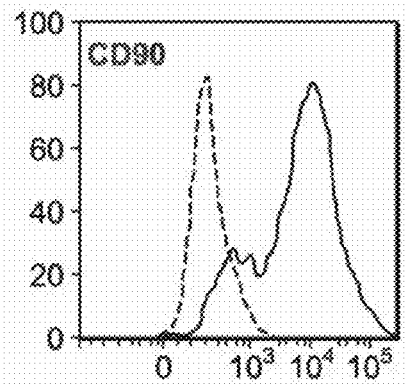
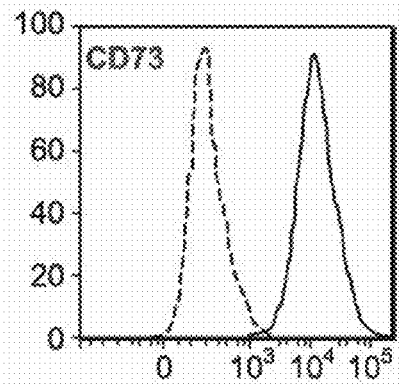
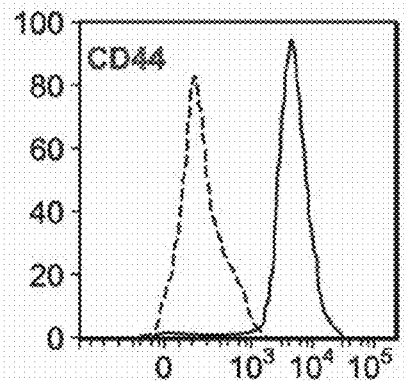
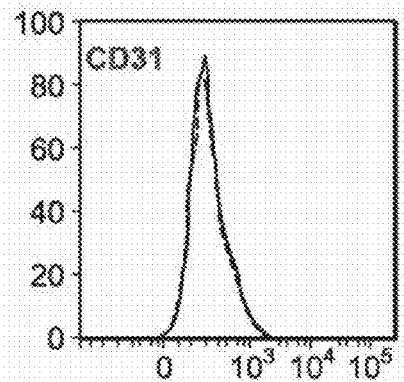
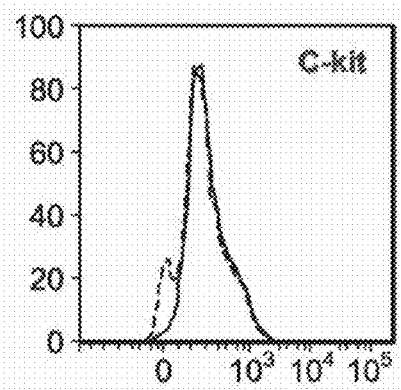
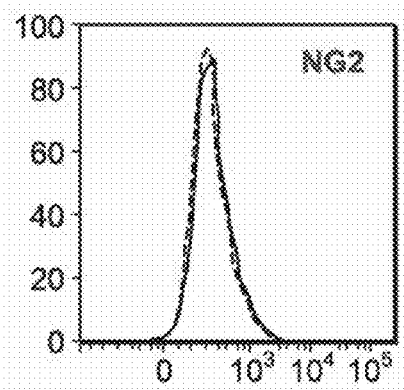

FIG. 3A (continued)
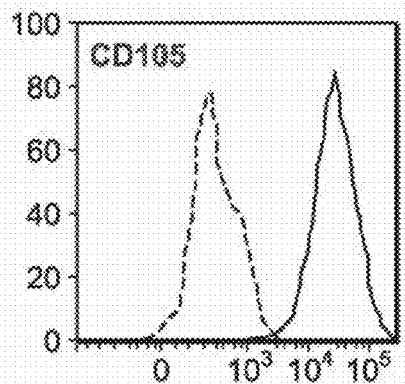
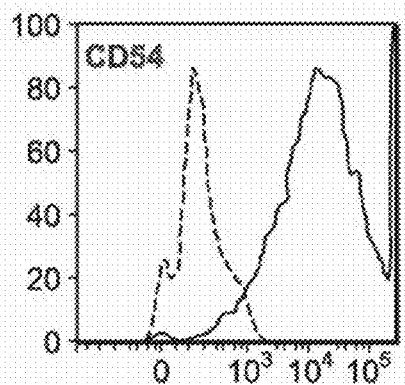
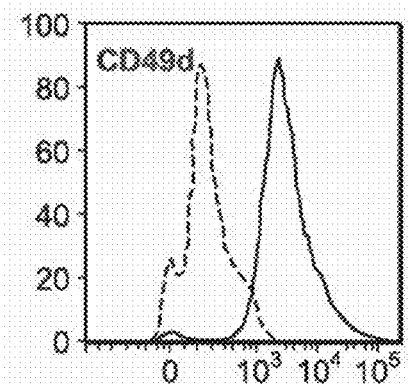
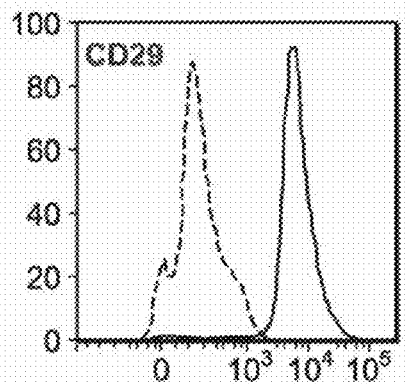
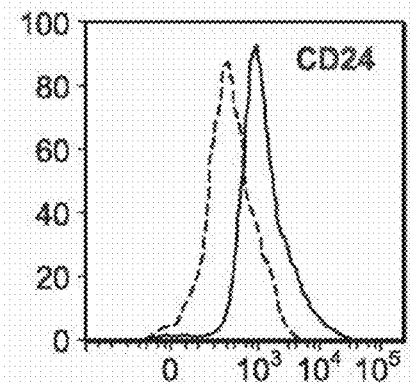
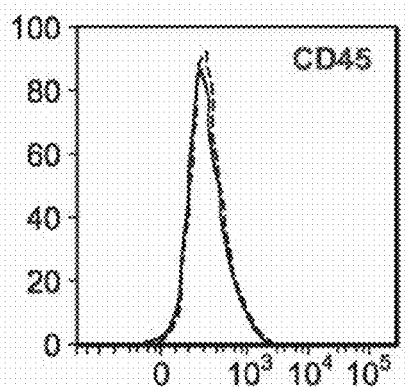
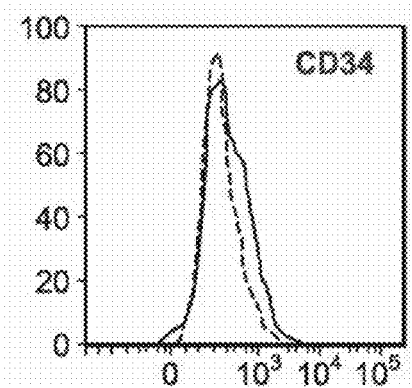

FIG. 3B (continued)
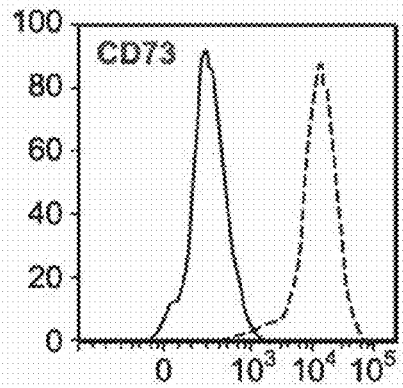
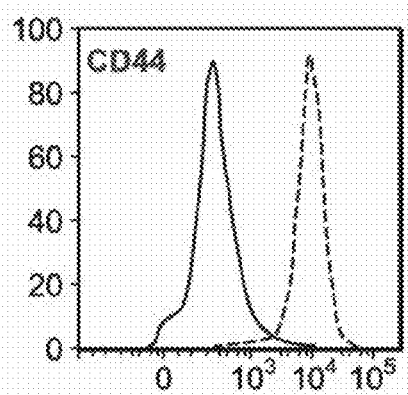
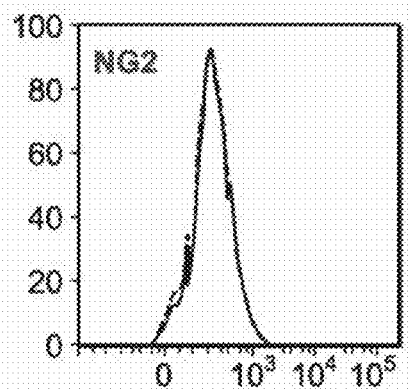
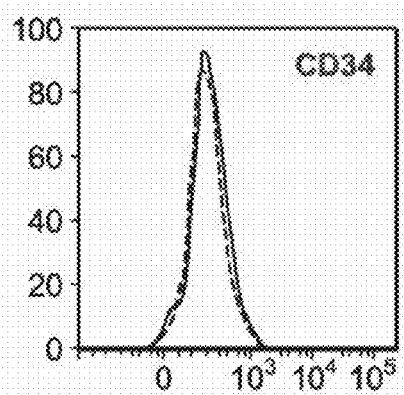

FIG. 11

Epicardin
LOCUS       NP_938206                179 aa            linear   PRI 23-
NOV-2008
DEFINITION  transcription factor 21 [Homo sapiens].
ACCESSION   NP_938206

1 mstgslsdve dlgevenlec dglkmdsnke fvtsnestee ssncengspq kgrgglgkrr
 61 kaptkkspls gvsqegkqvq rnaanarera rmrviskafs rikttipwvp pdtkiskldt
121 lrlassyiah lrgllandky engyihpvnl twpfmvagkp esdlkevvta sricgttas / NK2 transcription factor related, locus 5                Nkx 2.5
LOCUS       BAA35181                 324 aa            linear   PRI 22-
DEC-1996
DEFINITION  Nkx-2.5 [Homo sapiens].
ACCESSION   BAA35181

1 mfpspaltpt pfsvkdilnl eqggrslaaa gelsarleat lapsscmlaa fkpeayagpe
 61 aaapgipelr aelgrapspa kcasafpaap afypraysdp dpakdpraek kelcalqkav
121 elekteadna erpratrrrk prvlfsgaqv yelerrfkqq yelsaperdq lasvrkltst
181 qvkiwfqnrr yckcrqrgdq tlelvglppp ppppaariav pvivrdgkpc lgdsapyapa
241 ygvginpygy naypaypgy gaacspgysc taaypagpsp agpataaann nfvnfgvgdi
301 navgspgipq susgvstlhg lraw

FIG. 11 (continued)

```
GATA binding protein 4
LOCUS       BAA11334                 439 aa            linear   PRI 06-
FEB-2003
DEFINITION  GATA-4 transcription factor [Homo sapiens].
ACCESSION   BAA11334

1 myqslpwppt tgrppvptrr aapapsctar arprqstcph tgallragpv lppgrrrglc
 61 vrrpsgssg gaasgagpgt qggspgwsqa gadgaaytpp pvsprfsfpg ttgslaaaaa
121 aaareaaays sgggaagagl agreqygraa fagsysspyp aymadvgasw aaaaaasagp
181 fdspylhsip granpgarhp nldmfddfse grecvncgam stplwrrdgt ghylcnacgl
241 yhkmnginrp likpqrrlsa srvglscan cqttttiwr rnaegepvcn acglymklhg
301 vprplamrke gigtrkrkpk ninksktpaa psgsesippa sgassnssna ttssseemrp
361 iktepglssh yghsssvsqt fsvsamsghg psihpvlsal klspggvasp vsgspgtssk
421 qdswnslvla dshgdiita GATA binding protein 5
LOCUS       NP_536721                397 aa            linear   PRI 06-
APR-2008
DEFINITION  GATA binding protein 5 [Homo sapiens].
ACCESSION   NP_536721
```

FIG. 11 (continued)

```
  1 mgslaiaas prgaayadsg sflhapgags pmfvpparvp smlsvlsgce pspappelaa
 61 rpgwagtata dssafgpgsp hppaahppga tafpfahsps gpgsggsagg rdgsayggal
121 lpreqfaapl grpvgtsysa typayvspdv aqswtagpfd gsvlhglpgr rptfvsdfle
181 efpgegrecv ncgalstplw rrdgtghylc nacglyhkmn gvnrplvrpg krissrrag
241 lcctnchttn ttlwrrnseg epvcnacgly mklhgvprpl amkkesiqtr krkpktiaka
301 rgsgstrna saspsavast dssaatskak pslaspvcpg psnapgasgg eddslapghl
361 efkfepedfa fpstapspga glrgalrgea wcalala T-box 18
LOCUS       CAB37937              182 aa            linear    PRI 15-
APR-2005
DEFINITION  TBX18 protein [Homo sapiens].
ACCESSION   CAB37937                                                Tbx18 /

1 lwkrfheigt enlitkagir mfpamrvkis gldphqgyvi amdivpvdnk ryryvyhssk
 61 wmvagnadsp vpprvyihpd spasgetwmr qvisfdkiki tnneldqggh iiihsmhkyq
121 prvhvirkdc gddlspikpv psgegvakafs fpetvfftvt aygnqqitrl kldrnpfakg
181 fr
```

FIG. 11 (continued)

```
T-box 5                                                                  Tbx5 /
LOCUS       NP_000183               518 aa            linear   PRI 26-
APR-2009
DEFINITION  T-box 5 isoform 1 [Homo sapiens].
ACCESSION   NP_000183

1 madadegfgl ahtplepdak dlpcdskpes algapsksps spgaaftqgg megikvflhe
 61 relwlkfhev gtemiitkag rrmfpsykvk vtglnpktky illndivpad dhrykfadnk
121 wsvtgkaepa mpgrlyvhpd spatgahwmr qlvsfqkikl tnnhldpfgh ilinsmhkyq
181 prlhivkade nngfgsknta fcthvfpeta fiavtsvgnh kitglkienn pfakgfrgsd
241 dmelhrmsrm qskeypvvpi stvrqkvasn hspfssesra lstssnlgsq yqcengvsgp
301 sqdipppnp vplpgehsqi vhctkrkeee csttdhpykk pymetspsee dsfyrssypa
361 qqglgasyrt esagrgacmy assappsepv psledisont wpsmpsyssc tvtvgpmdr
421 lpychfsahf tsgplvpria gmanhgspql gegmfghqts vahqpvvrqc gpqtglqspg
481 tlqppeflys hgvprtlsph qynsvhgvgm vpewsdns Wilms tumor 1                                                           Wt1 /
LOCUS       NP_000369               497 aa            linear   PRI 10-
MAY-2009
DEFINITION  Wilms tumor 1 isoform A [Homo sapiens].
ACCESSION   NP_000369
```

FIG. 11 (continued)

```
  1 mgdpastcvp epasqhtlrs gpgclgpeg ggvrdpggiw aklgaaeasa erlggrisrg
 61 asgsepqgmg sdvrdlnall pavpslgggg gcalpvsgaa qwapvldfap pgasaygslg
121 gpapppappp ppppphsfi kqepswggae pheeqclsaf tvhfsgqftg tagacrygpf
181 gpppsgass ggarmfpnap yipsclesgp airnggystv tfdgtpsygh tpshhaaqfp
241 nhsfkhedpm gqggslgegq ysvppppvgc htptdsctgs qallirtpys sdnlygmtsq
301 lecmtwnqmn lgatlkghst gyesdnhtcp ilcgayrih thgvfrgigd virpgvapt
361 lvrsasetse krpfmcaypg cnkryfklsh lqmhsrkhtg ekpyqcdfkd cerifsrsdq
421 ikrhgrrhtg vkpfqcktcq rkfsrsdhlk lqmhsrkhtg ekpyqcdfkd cerifsrsdq
481 rhhnmhqrnm tkigial                                    Isl-1 /
```

```
islet-1 transcription factor
LOCUS       NP_002193                349 aa            linear   PRI 28-
JAN-2009
DEFINITION  islet-1 [Homo sapiens].
ACCESSION   NP_002193
```

```
  1 mgdmgdppkk krlisicvgc gngindqyil rvspdlewha aclkcaecnq ylidesctcfv
 61 rdgktycrd yirlygikca kcsigfsknd fvmrarskvy hiecfrcvac srqilpgdef
121 alredglfcr adhavveras lgagdplspl hparplqmaa hparplqmaa episarqpal rphvhkqpek
181 ttvrtvlne kqlhtlrtcy aanprpdalm keglventgl sprvirwfg nkrckdkkrs
241 immkqiqqq pndktniqgm tgtpmvaasp erhdgylqan pvevgsyqpp wkvlsdfalg
301 sdidpafgq lvnfseggpg snstgsevas mssqlpdtpn smvasplea             Mef2c /
```

FIG. 11 (continued)

```
myocyte enhancer factor 2c (isoform 1)
LOCUS       NP_002388                473 aa            linear   PRI 29-
MAR-2009
DEFINITION  myocyte enhancer factor 2C isoform 1 [Homo sapiens].
ACCESSION   NP_002388

1 mgrkkiqitr imdernrqvt ftkrkfglmk kayelsvlcd celaliifns tnklfqyast
 61 dmdkvlkyt eynephesrt nsdivetlrk kglngcdspd pdaddsvghs pesedkyrki
121 necidimisr grlcavpppn fempvsipvs shnslvysnp vssignpnli piahpsiqrn
181 smspgvthrp psagntgglm ggdltsgagt sagngygnpr nspglivspg ninknmqaks
241 ppmnlgmnn rkpdlrvllp pgsknntmpsv sedvdillng rinnsgsacs latpvvsvat
301 ptipggngg ypsaisttvg teyslssadl ssisgfntas alhlgsvtgw qqqhlhnmpp
361 salsqlgact sthisqssni sipstqsini ksepvspprd rtttpsrypq htrheagrsp
421 vdslsscss ydgsdredhr nefhspiglt rpspderesp svkrmrlseg wat Mef2c / myocyte enhancer factor 2C (isoform 2)
LOCUS       NP_001124477             463 aa            linear   PRI 29-
MAR-2009
DEFINITION  myocyte enhancer factor 2C isoform 2 [Homo sapiens].
ACCESSION   NP_001124477
```

FIG. 11 (continued)

```
  1 mgrkkiqitr imdernrqvt ftkrkfglmk kayelsvlcd ceiaiiifns tnklifqyast
 61 dmdkvlkyt eynephesrt nsdivealnk kenkgcespd pdssyaltpr teekykkine
121 efdnmikshx ipavpppnfe mpvsipvssh nslvysnpvs signpulpl ahpsiqrnsm
181 spgvthrpps agntggimgg ditsgagtsa gngygnprns pglivspgni nknmgakspp
241 pmnlgmnnrk pdlrvlippg skntmpsvng rinnsqsaqs latpvvsvat ptlpgqmgg
301 ypsaisttyg teyslssadl ssisgfntas alhlgsvtgw qqqhlhmpp salsqiqact
361 sthlsqssnl slpstqslni ksepvspprd rtttpsrypa htrheagrsp vdslsscsse
421 ydgsdredhr nefnspigit rpspderesp svkrmriseg wat
```

```
LOCUS       NP_705832                939 aa            linear   PRI 12-
APR-2009
DEFINITION  myocardin isoform 2 [Homo sapiens].
ACCESSION   NP_705832
```

FIG. 11 (continued)

```
  1 mtligsehsl lirskfrsvl qlrlggrltq eqlanggllp plkrpaefhe qrkhldsdka
 61 knslkrkarn rcnsadlvnm hllgastaer siptagmklk rarladdlne klalrpgple
121 lveknllpvd savkealkgn qvsfskstda fafeedsssd glspqgtrse dpqnsagspp
181 dakasdtpst gslgtngdla sgsendrnds asgpshqsda gkqglgppst plavhaavks
241 kslgdsknrh kkpkdpkpkv kklkyhqylp pdqkaekspp pmdsayarll qqglflqlq
301 llsqgqgqgq hrfsylgmhq aglkepneqm vrnpssstp lsntplspvk nsfsggtgvs
361 sfkpgplppn lddlkvselr qglrlrglpv sgtktalmdr lrpfqdcsgn pvpnfgdltt
421 vtfpvtpntl pnygssstss alsngfyhfg stssppisp assdlsvags lpdtfndasp
481 sfglhpspvh vcteeslmss lnggsvpsel dglsekdkm lvekqkvlne ltwklqgeqr
541 qveelrmglg kqkrnncsek kplpflaasl kqeeavsscp fasqvpvkrq sssechppa
601 ceaaglqplg nahcvessdq tnvlsstfls pqcspqghspl gavkspqhls lppspnnphf
661 lpssgagge ghrvsspiss qvctagmagl hssdkvgpkf slpsptfsks ssalsevtqp
721 psyedavkqq mtrsqgmdel ldvllesgem padaredhsc lqkvpkiprs srsptavtk
781 psasfeqass gsqlpfdpya tdsdehlevl lnsqsplgkm sdvtllkigs eephfdglmd
841 gfsgkaaedl fnaheilpgp lspmqtqfsp ssvdsnglgl sftespwetm ewldltppns
901 tpgflsaltts spslfnldfl dvtdlnlnss mdlhlggw
```

Treated with 25x EPI CdM

Treated with 25x EPI CdM

COMPOSITIONS AND METHODS FOR CARDIAC TISSUE REPAIR

CROSS-REFERENCE TO RELATED APPLICATIONS

This application is a divisional of U.S. patent application Ser. No. 13/220,555, allowed, which is a continuation-in-part of International Application No. PCT/US2010/001540, which was filed on May 26, 2010, and published as International Publication No. WO 2010/138180, which claims the benefit of U.S. Provisional Application No. 61/181,071, which was filed on May 26, 2009, the disclosures of which are hereby incorporated in their entireties.

STATEMENT OF RIGHTS TO INVENTIONS MADE UNDER FEDERALLY SPONSORED RESEARCH

This work was supported by the following grant from the National Institutes of Health, Grant No: HL085210-02. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 26, 2011, is named 83811CIP.txt and is 49,195 bytes in size.

BACKGROUND OF THE INVENTION

Mammalian cells require a consistent source of oxygen and nutrients to allow them to function normally. When their access to oxygen and nutrients is interrupted, cell damage and death can quickly result. Certain cell types, including muscle cells and neurons are particularly vulnerable to ischemic injury in connection with myocardial infarction and stroke. Despite recent advances in treating ischemic injuries, stroke and myocardial infarction continue to kill or disable vast numbers of people each year. In the United States alone, 600,000 new myocardial infarctions and 320,000 recurrent attacks occur annually. About 38 percent of the people who experience a myocardial infarction in a given year will die, while many of those who survive will experience some loss in cardiac function. Current cell replacement strategies for treating myocardial infarction involving the injection of stem/progenitor cells result in modest improvements in cardiac function, at best. Low levels of engraftment, survival, and cell replacement after injection of adult or embryonic stem cells into the injured left ventricle wall are current issues that reduce the potential effectiveness of cell replacement strategies after myocardial infarction. Moreover, infusion of cultured adult stem/progenitor cells can be accompanied by microembolism and cardiac arrhythmias. Accordingly, improved methods of treating tissue injury, particularly ischemic injuries associated with myocardial infarction, are urgently required.

SUMMARY OF THE INVENTION

As described below, the present invention features compositions and methods for treating or preventing cardiac tissue damage, including damage associated with an ischemic event.

In one aspect, the invention provides a pharmaceutical composition containing or consisting essentially of one or more cellular factors (e.g., HGF, VEGF, SDF-1 alpha, and/or IGF-1) having cardiac protective activity in a pharmaceutically acceptable excipient, where the cellular factor is isolated from a cultured epicardial progenitor cell. In one embodiment, the pharmaceutical composition comprises one or more cellular factors isolated from a cultured epicardial progenitor cell, and one or more recombinant cellular factors (e.g., HGF, VEGF, SDF-1 alpha, and/or IGF-1).

In another aspect, the invention provides a pharmaceutical composition containing a secreted cellular factor (e.g., HGF, VEGF, SDF-1 alpha, and/or IGF-1) in a pharmaceutically acceptable excipient, where the cellular factor is isolated from an epicardial progenitor cell selected for expression of epicardin, Nkx 2.5, Isl-1, GATA 5, WT1, Tbx18, and/or Tbx5 polypeptides or polynucleotides; has a biological activity that is any one or more of reducing cell death in a cell population at risk thereof, increasing cell survival, reducing inflammation, increasing epicardial cell proliferation, increasing epithelial to mesenchymal transformation, and increasing cardiac function; has a molecular weight that is at least about 5 kD; and is inactivated by heat denaturation. In one embodiment, the pharmaceutical composition comprises one or more cellular factors isolated from a cultured epicardial progenitor cell, and one or more recombinant cellular factors (e.g., HGF, VEGF, SDF-1 alpha, and/or IGF-1).

In another aspect, the invention provides a method for producing a pharmaceutical composition containing one or more cellular factors (e.g., HGF, VEGF, SDF-1 alpha, and/or IGF-1), the method involving selecting an isolated epicardial progenitor cell that expresses any one or more of epicardin, Nkx 2.5, Isl-1, GATA 5, WT1, Tbx18, and Tbx5 polypeptides or polynucleotides; and isolating a composition comprising one or more cellular factors from the cell, thereby generating a composition that promotes cardiac tissue repair. In one embodiment, the method involves identifying one or more of said cellular factors. Once identified, the cellular factors may be recombinantly expressed and added to the pharmaceutical composition to increase the concentration of such factors present in the composition.

In still another aspect, the invention provides a method for reducing cardiac cell death or increasing cardiac cell survival or proliferation, the method involving contacting a cardiac cell at risk of cell death with a composition comprising or consisting essentially of one or more secreted cellular factors (e.g., HGF, VEGF, SDF-1 alpha, and/or IGF-1) having cardiac protective activity, where the factor is isolated from an epicardial progenitor cell in vitro. In one embodiment, the pharmaceutical composition comprises one or more cellular factors isolated from a cultured epicardial progenitor cell, and one or more recombinant cellular factors (e.g., HGF, VEGF, SDF-1 alpha, and/or IGF-1).

In yet another aspect, the invention provides a method for stabilizing or reducing cardiac tissue damage in a subject (e.g., a human or rodent), the method involving contacting a cardiac cell of the subject with a composition comprising one or more secreted cellular factors (e.g., HGF, VEGF, SDF-1 alpha, and/or IGF-1) having epicardial protective activity, thereby stabilizing or reducing cardiac tissue damage in the subject. In one embodiment, one or more of said cellular factors are recombinantly expressed.

In another aspect, the invention provides a method for increasing cardiac function in a subject at risk of ischemic cardiac tissue damage, the method involving contacting a cardiac cell of the subject with one or more secreted cellular factors (e.g., HGF, VEGF, SDF-1 alpha, and/or IGF-1) having epicardial protective activity, thereby increasing cardiac function in the subject. In one embodiment, one or more of said cellular factors are recombinantly expressed.

In yet another aspect, the invention provides a method for treating or preventing vascular rhexis in a subject (e.g., a human or rodent), the method involving contacting a cardiac cell of the subject with a composition comprising one or more secreted cellular factors (e.g., HGF, VEGF, SDF-1 alpha, and/or IGF-1) having epicardial protective activity, thereby treating or preventing vascular rhexis in the subject. In one embodiment, one or more of said cellular factors are recombinantly expressed.

In still another aspect, the invention provides a method for reducing cardiac cell death or increasing cardiac cell survival or proliferation, the method involving contacting a cardiac cell at risk of cell death (e.g., apoptotic, necrotic) with an effective amount of a composition containing one or more secreted cellular factors (e.g., HGF, VEGF, SDF-1 alpha, and/or IGF-1) isolated from an epicardial progenitor cell that expresses any one or more of epicardin, Nkx 2.5, Isl-1, GATA 5, WT1, Tbx18, and Tbx5; thereby increasing cardiac cell survival or proliferation. In one embodiment, one or more of said cellular factors are recombinantly expressed.

In another aspect, the invention provides a method for stabilizing or reducing cardiac tissue damage in a subject at risk thereof, the method involving contacting a cardiac cell of the subject with an effective amount of a composition containing one or more secreted cellular factors (e.g., HGF, VEGF, SDF-1 alpha, and/or IGF-1) isolated from an epicardial progenitor cell that expresses epicardin, Nkx 2.5, Isl-1, GATA 5, WT1, Tbx18, and Tbx5, thereby stabilizing or reducing cardiac tissue or heart damage. In one embodiment, one or more of said cellular factors are recombinantly expressed.

In yet another aspect, the invention provides a method for increasing cardiac function in a subject at risk of ischemic tissue damage, the method involving contacting a cardiac cell of the subject with an effective amount of a composition containing one or more secreted cellular factors (e.g., HGF, VEGF, SDF-1 alpha, and/or IGF-1) isolated from an epicardial progenitor cell that expresses any one or more of epicardin, Nkx 2.5, Isl-1, GATA 5, WT1, Tbx18, and Tbx5, thereby increasing cardiac function. In one embodiment, one or more of said cellular factors are recombinantly expressed.

In another aspect, the invention provides a method for treating or preventing vascular rhexis in a subject, the method involving contacting a cardiac cell of the subject with an effective amount of a composition containing one or more secreted cellular factors (e.g., HGF, VEGF, SDF-1 alpha, and/or IGF-1) isolated from an epicardial progenitor cell that expresses epicardin, Nkx 2.5, Isl-1, GATA 5, WT1, Tbx18, and Tbx5, thereby treating or preventing vascular rhexis in the subject.

In still another aspect, the invention provides a method for identifying an agent useful for cardiac tissue repair or regeneration, the method involving contacting a cardiac cell at risk of cell death with a composition containing a secreted cellular factor isolated from an epicardial progenitor cell selected for expression of any one or more of epicardin, Nkx 2.5, Isl-1, GATA 5, WT1, Tbx18, and Tbx5; detecting an increase in cell survival, growth, or proliferation or a decrease in cell death relative to an untreated control cell; and isolating the agent, thereby identifying an agent useful for cardiac tissue repair or regeneration. In one embodiment, the method further involves purifying the factor. In other embodiments, the purification involves selecting fractions having a desired biological activity. In still other embodiments, the selected fraction increases cardiac cell survival, reduces cardiac cell death, increases cardiac cell proliferation, or increases cardiac tissue or heart function.

In another aspect, the invention provides a cellular composition containing an isolated epicardial progenitor cell or progeny cell thereof that expresses any one or more of epicardin, Nkx 2.5, Isl-1, GATA 5, WT1, Tbx18, and Tbx5. In various embodiments, at least about 50% (60%, 70%, 80%, 90%, 95%, or 100%) of the cells present in the composition express any one or more of epicardin, Nkx 2.5, Isl-1, GATA 5, WT1, Tbx18, and Tbx5 polypeptides or polynucleotides or are derived from a progenitor cell that expresses any one or more of epicardin, Nkx 2.5, Isl-1, GATA 5, WT1, Tbx18, and Tbx5 polypeptides or polynucleotides. In various embodiments, the cellular composition contains cells that express one or more polypeptides of GATA 4, Mef2c, myocardin, $CD105^+$, $CD90^+$, $CD73^+$, $CD44^+$, $CD29^+$, and Stro-1. In various embodiments, the cellular composition contains cells that fail to express detectable levels or express reduced levels (relative to a reference cell) of a polypeptide that is any one or more of $CD34^+$, $CD45^+$, c-kit, and vascular pericyte marker.

In still another aspect, the invention provides an isolated epicardial progenitor cell that expresses any one or more of epicardin, Nkx 2.5, Isl-1, GATA 5, WT1, Tbx18, and Tbx5. In various embodiments, the isolated epicardial progenitor cell expresses a polypeptide that is any one or more of GATA 4, Mef2c, myocardin, $CD105^+$, $CD90^+$, $CD73^+$, $CD44^+$, $CD29^+$, and Stro-1. In particular embodiments, the isolated epicardial progenitor cell fails to express detectable levels or expresses reduced levels of a polypeptide that is any one or more of $CD34^+$, $CD45^+$, c-kit, and vascular pericyte marker.

In another aspect, the invention provides an isolated population of epicardial progenitor cells, where the epicardial progenitor cells express any one or more of epicardin, Nkx 2.5, Isl-1, GATA 5, WT1, Tbx18, and Tbx5. In various embodiments, the epicardial progenitor cells express a polypeptide that is any one or more of GATA 4, Mef2c, myocardin, $CD105^+$, $CD90^+$, $CD73^+$, $CD44^+$, $CD29^+$, and Stro-1. In particular embodiments, the epicardial progenitor cells fail to express detectable levels or expresses reduced levels of a polypeptide that is any one or more of $CD34^+$, $CD45^+$, c-kit, and vascular pericyte marker.

The invention further provides a pharmaceutical composition comprising one or more secreted cellular factors isolated from an epicardial progenitor cell of any previous claim or otherwise delineated herein. In one embodiment, the composition supports cardiac cell survival, growth, or proliferation.

In yet another aspect, the invention provides a method of culturing an isolated epicardial progenitor cell or progeny thereof that expresses any one or more of epicardin, Nkx 2.5, Isl-1, GATA 5, WT1, Tbx18, and Tbx5, involving culturing an isolated epicardial progenitor cell or progeny thereof on polystyrene. In particular embodiments, the isolated epicardial progenitor cell or progeny thereof fails to undergo epithelial to mesenchymal transformation.

In various embodiments of any of the above aspects or any other aspect of the invention delineated herein, the epicardial progenitor cell or progeny cell thereof expresses or is selected for expression of one or more of epicardin, Nkx 2.5, Isl-1, GATA 5, WT1, Tbx18, and/or Tbx5 polypeptides or polynucleotides. For example, the epicardial progenitor cell expresses one, two, three, four, five, six or seven of epicardin, Nkx 2.5, Isl-1, GATA 5, WT1, Tbx18, and/or Tbx5 polypeptides or polynucleotides. In various embodiments of any of the above aspects or any other aspect of the invention delineated herein, the epicardial progenitor cell or progeny cell thereof expresses a polypeptide that is any one or more of GATA 4, Mef2c, myocardin, $CD105^+$, $CD90^+$, $CD73^+$, $CD44^+$, $CD29^+$, and Stro-1. In various embodiments of any of the above aspects, the epicardial progenitor cell or progeny cell thereof is selected for expression of one or more of a cell surface marker (e.g., $CD105^+$, $CD90^+$, $CD73^+$, $CD44^+$, $CD29^+$, and Stro-1). In particular embodiments, the epicardial progenitor cell or progeny cell thereof is selected for expression of one or more of a cell surface marker prior to selection for expression of an internal marker (e.g., epicardin, Nkx 2.5, Isl-1, GATA 5, WT1, Tbx18, Tbx5, GATA 4, Mef2c, and/or myocardin). In various embodiments of any of the above aspects, the epicardial progenitor cell or progeny cell thereof fails to express detectable levels or expresses reduced levels of one or more of $CD34^+$, $CD45^+$, c-kit, and vascular pericyte marker.

In various embodiments of the above aspects or any other aspect of the invention delineated herein, the epicardial progenitor cell or progeny cell thereof is a human cell in vitro. In various embodiments of any of the above aspects delineated herein, the epicardial progenitor cell or progeny cell thereof is an epithelial cell. In various embodiments, the epithelial cell or progeny cell thereof is isolated prior to, during, or subsequent to epithelial-mesenchymal transformation (EMT). In still other embodiments, a selected cell is capable of differentiating into any one or more of myocytes, cardiac fibroblasts, smooth muscle cells, or endothelial cells.

In various embodiments of any of the above aspects, the secreted cellular factor is isolated from an epicardial progenitor cell selected for expression of any one or more of epicardin, Nkx 2.5, Isl-1, GATA 5, WT1, Tbx18, and Tbx5. In various embodiments, the cellular factor has a biological activity that is any one or more of reducing cell death in a cell population at risk thereof, increasing cell survival, reducing inflammation, increasing epicardial cell proliferation, increasing epithelial to mesenchymal transformation, and increasing cardiac function. In various embodiments of any of the above aspects delineated herein, the factor has a molecular weight that is at least about 5 kD. In other embodiments, the factor is inactivated by heat denaturation. In other embodiments, the cellular factor is isolated from a primary cultured or a cell passaged for at least one, two, three, four, five, six or more passages.

In various embodiments of any of the above aspects delineated herein, the method reduces apoptosis or increases cell proliferation (e.g., an alteration of at least about 5%, 10%, 20%, 25%, 50%, 75%, or 100%). In various embodiments of any of the above aspects delineated herein, the method increases cardiac cell number or reduces cardiac cell death.

In particular embodiments, the method increases cardiac cell number by at least about 5%, 10%, 25%, 50%, 75%, 80%, 90% or 100% compared to a corresponding untreated control cardiac tissue or heart.

In various embodiments of any of the above aspects delineated herein, the composition is administered to a subject directly to a site of cardiac tissue damage or cardiac disease or is administered systemically. In various embodiments of any of the above aspects delineated herein, the composition is administered to a subject directly to a site of cardiac tissue damage or cardiac disease or is administered systemically. In various embodiments of any of the above aspects delineated herein, the subject has a disease or disorder that is any one or more of myocardial infarction, congestive heart failure, stroke, and ischemia. In various embodiments of any of the above aspects delineated herein, the method prevents or ameliorates ischemic damage. In particular embodiments, the method prevents or ameliorates ischemic damage in a cardiac tissue post-myocardial infarction.

In various embodiments of any of the above aspects delineated herein, a reduction in cardiac tissue damage is indicated by a reduction in the total percentage of left ventricle with infarction, a reduction in the percent of myocardial infarction in the anterior wall of the left ventricle, an increase in cardiac function, or a reduction in vascular rhexis. In various embodiments of any of the above aspects delineated herein, an increase in cardiac function is indicated by increased cardiac output, reduced left ventricular end diameter during diastole (LVEDD), improves echocardiography scoring for wall motion, increases the difference in left ventricle anterior wall thickness between diastole and systole, or improves percent fractional shortening.

In still other embodiments, a pharmaceutical composition of the invention comprises one or more cellular factors isolated from a cultured epicardial progenitor cell, and one or more recombinant cellular factors (e.g., HGF, VEGF, SDF-1 alpha, and/or IGF-1). In other embodiments, the method involves identifying one or more of said secreted cellular factors. Once identified, the cellular factors may be recombinantly expressed and added to the pharmaceutical composition to increase the concentration of such factors present in the composition.

In particular embodiments, the cellular factor is one or more of HGF, VEGF, SDF-1 alpha, and IGF-1. In other embodiments, a composition of the invention contains or consists of HGF, VEGF, SDF-1 alpha and IGF-1. In particular embodiments, the amount of HGF is between about 3-500 ng/ml (e.g., 3, 4, 5, 10, 20, 30, 40, 50, 75, 100, 125, 150, 200, 225, 250, 300, 350, 400, 450, 500 ng/ml), VEGF is between about 0.5-500 ng/ml (e.g., 0.5, 0.6, 0.7, 0.8, 0.9, 1, 2, 3, 4, 5, 10, 20, 30, 40, 50, 75, 100, 125, 150, 200, 225, 250, 300, 350, 400, 450, 500 ng/ml), SDF-1 alpha is between about 0.15 ng-500 ng/ml (e.g., 0.15, 0.2, 0.3, 0.4, 0.5, 0.6, 0.7, 0.8, 0.9, 1, 2, 3, 4, 5, 10, 20, 30, 40, 50, 75, 100, 125, 150, 200, 225, 250, 300, 350, 400, 450, 500 ng/ml), and IGF-1 is between about 0.03 ng-500 ng/ml (e.g., 0.3, 0.4, 0.5, 0.6, 0.7, 0.8, 0.9, 1, 2, 3, 4, 5, 10, 20, 30, 40, 50, 75, 100, 125, 150, 200, 225, 250, 300, 350, 400, 450, 500 ng/ml). In other embodiments, the composition comprises at least HGF, VEGF, and SDF or at least HGF and VEGF.

Other features and advantages of the invention will be apparent from the detailed description, and from the claims.

Definitions

By "epicardial progenitor cell" is meant a cell that gives rise to a cell of the epicardium, or a cell that expresses or whose progeny express any one or more of epicardin, Nkx 2.5, Isl-1, GATA 5, WT1, Tbx18, and Tbx5. In other embodiments, an epicardial progenitor cell expresses one or more of GATA 4, Mef2c, myocardin, $CD105^+$, $CD90^+$, $CD73^+$, $CD44^+$, $CD29^+$, and Stro-1. Exemplary amino acid sequences for the aforementioned polypeptides are known in the art and/or described herein at FIG. 11.

By "increasing epicardial cell proliferation" is meant increasing cell division of an epicardial progenitor cell or a cell derived from an epicardial progenitor cell in vivo or in vitro. Increasing epicardial cell proliferation may also include promoting, supporting, or inducing the differentiation and/or migration of epicardial cells. Epicardial cell proliferation may be measured by determining the number of cells expressing one or more of epicardin, Nkx 2.5, Isl-1, GATA 5, WT1, Tbx18, Tbx5 or any marker described herein (e.g., by fluorescence-activated cell sorting). For example, an increase in cell number may be at least about a 5%, 10%, 15%, 20%, 30%, 40%, 50%, 60%, 70%, 80%, 90%, or even 100% increase in the number of epicardial cells relative to the number of cells present in a naturally-occurring, corresponding cardiac tissue or heart.

By "cardiac protective activity" is meant any biological activity that maintains or increases the survival or function of a cardiac cell or cardiac tissue in vitro or in vivo.

By "cardiac function" is meant the biological function of cardiac tissue or heart (e.g., contractile function). Methods for measuring the biological function of the heart are standard in the art (e.g., Textbook of Medical Physiology, Tenth edition, (Guyton et al., W.B. Saunders Co., 2000) and are also described herein. By "increasing in cardiac function" is meant an increase in a biological function of the heart by at least about 5%, 10%, 15%, 20%, 30%, 40%, 50%, 60%, 70%, 80%, 90%, or even 100% relative to the biological function present in a naturally-occurring, corresponding cardiac tissue or heart.

By "cell survival" is meant cell viablility.

By "reducing cell death" is meant reducing the propensity or probability that a cell will die. Cell death can be apoptotic, necrotic, or by any other means.

By "reducing inflammation" is meant reducing the severity or symptoms of an inflammatory reaction in a tissue. An inflammatory reaction within tissue is generally characterized by leukocyte infiltration, edema, redness, pain, neovascularization (in advanced cases), and finally impairment of function. Inflammation can also be measured by analyzing levels of cytokines, C reactive protein, or any other inflammatory marker.

By "cellular factor" is meant any biological agent produced by a cell. While cellular factors isolated from culture media are typically secreted by cells in culture, the scope of the invention is intended to include any factor released from a cultured cell into growth media. In one embodiment, a cellular factor of the invention is secreted by a cell or is released into culture media when a cell breaks open and releases its contents into the growth media. Exemplary cellular factors include HGF, VEGF, SDF-1 alpha, and IGF-1.

By "epithelial to mesenchymal transformation" or "EMT" is meant a program of development of biological cells characterized by loss of cell adhesion, repression of E-cadherin expression, and increased cell mobility. Epithelial to mesenchymal transformation plays a role in numerous developmental processes including mesoderm formation and neural tube formation. Epithelial to mesenchymal transformation may be measured by loss of cell adhesion, repression of E-cadherin expression, and/or increased cell mobility. For example, an increase in cell mobility may be a 5%, 10%, 15%, 20%, 30%, 40%, 50%, 60%, 70%, 80%, 90%, or even 100% increase in the mobility of cells of epithelial cells relative to the mobility of epithelial cells present in a naturally-occurring, corresponding tissue or organ.

By "vascular rhexis" is meant loss of vascular integrity following reperfusion after myocardial infarction. Vascular rhexis can lead to progressive loss of myocyte function, necrosis, and infarct expansion in damaged cardiac tissue. Vascular rhexis may be assessed by methods to determine vascular damage (e.g., extravasation; cell death).

By "secreted cellular factor" is meant any biologically active agent that a cell secretes during in vitro culture.

By "epicardin polypeptide" is meant a protein or fragment thereof having at least about 85% identity to NCBI Accession No. NP_938206, or that binds an antibody generated against the epicardin antigen.

By "epicardin nucleic acid molecule" is meant a polynucleotide encoding a epicardin polypeptide.

By "Nkx 2.5 or NK2 transcription factor related, locus 5 polypeptide" is meant a protein or fragment thereof having at least about 85% identity to NCBI Accession No. BAA35181 or that binds an antibody generated against the Nkx 2.5 antigen.

By "NK2 transcription factor related, locus 5 nucleic acid molecule" is meant a polynucleotide encoding a Nkx 2.5 polypeptide.

By "GATA 4 or GATA binding protein 4 polypeptide" is meant a protein or fragment thereof having at least about 85% identity to NCBI Accession No. BAA11334 or that binds an antibody generated against the GATA 4 antigen.

By "GATA 4 nucleic acid molecule" is meant a polynucleotide encoding a GATA 4 polypeptide.

By "GATA 5 or GATA binding protein 5 polypeptide" is meant a protein or fragment thereof having at least about 85% identity to NCBI Accession No. NP_536721 or that binds an antibody generated against the GATA 5 antigen.

By "GATA 5 nucleic acid molecule" is meant a polynucleotide encoding a GATA 5 polypeptide.

By "Tbx18 or T-box 18 polypeptide" is meant a protein or fragment thereof having at least about 85% identity to NCBI Accession No. CAB37937 or that binds an antibody generated against the Tbx18 antigen.

By "Tbx18 nucleic acid molecule" is meant a polynucleotide encoding a Tbx18 polypeptide.

By "Tbx5 or T-box 5" is meant a polypeptide or fragment thereof having at least about 85% identity to NCBI Accession No. NP_000183 or that binds an antibody generated against the Tbx5 antigen.

By "Tbx5 nucleic acid molecule" is meant a polynucleotide encoding a Tbx5 polypeptide.

By "Wt1 or Wilms tumor 1 polypeptide" is meant a protein or fragment thereof having at least about 85% identity to NCBI Accession No. NP_000369 or that binds an antibody generated against the Wt1 antigen.

By "Wt1 nucleic acid molecule" is meant a polynucleotide encoding a Wt1 polypeptide.

By "Isl-1 or islet-1 transcription factor polypeptide" is meant a protein or fragment thereof having at least about 85% identity to NCBI Accession No. NP_002193 or that binds an antibody generated against the Isl-1 antigen.

By "Isl-1 nucleic acid molecule" is meant a polynucleotide encoding a Isl-1 polypeptide.

By "Mef2c or myocyte enhancer factor 2c" is meant a polypeptide or fragment thereof having at least about 85% identity to NCBI Accession No. NP_002388 (isoform 1) or NCBI Accession No. NP_001124477 (isoform 2) or that binds an antibody generated against the Mef2c antigen.

By "Mef2c nucleic acid molecule" is meant a polynucleotide encoding a Mef2c polypeptide.

By "myocardin polypeptide" is meant a protein or fragment thereof having at least about 85% identity to NCBI Accession No. NP_705832 or that binds an antibody generated against the myocardin antigen.

By "myocardin nucleic acid molecule" is meant a polynucleotide encoding a myocardin polypeptide.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "deficiency of a particular cell-type" is meant fewer of a specific set of cells than are normally present in a tissue or organ not having a deficiency. For example, a deficiency is a 5%, 10%, 15%, 20%, 30%, 40%, 50%, 60%, 70%, 80%, 90%, or even 100% deficit in the number of cells of a particular cell-type (e.g., cardiomyocytes, epicardial progenitor cells, embryonic stem cells, endothelial cells, endothelial precursor cells, fibroblasts, neurons, adipocytes) relative to the number of cells present in a naturally-occurring, corresponding tissue or organ. Methods for assaying cell-number are standard in the art, and are described in (Bonifacino et al., Current Protocols in Cell Biology, Looseleaf, John Wiley and Sons, Inc., San Francisco, Calif., 1999; Robinson et al., Current Protocols in Cytometry Loose-leaf, John Wiley and Sons, Inc., San Francisco, Calif., October 1997).

"Derived from" as used herein refers to the process of obtaining a cell from a subject, embryo, biological sample, or cell culture.

"Detect" refers to identifying the presence, absence or amount of the object to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include any disease or injury that results in a reduction in cell number or biological function, including ischemic injury, such as stroke, myocardial infarction, or any other ischemic event that causes tissue damage.

By "effective amount" is meant the amount of a required to ameliorate the symptoms of a disease relative to an untreated patient. The effective amount of active compound(s) used to practice the present invention for therapeutic treatment of a ischemic injury varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis. When a cellular factor is "isolated" from a cultured epicardial progenitor cell the cellular factor is typically separated from cells and cellular debris. It need not be purified to homogeneity. In fact, the composition comprising an isolated cellular factor typically comprises any number of cellular factors whose presence contributes to the biological activity (e.g., growth promoting, survival promoting, or proliferation promoting activity) of the composition. In one embodiment, a composition of the invention comprises or consists of conditioned media from which cells and cellular debris have been removed. If desired, the composition is supplemented with one or more recombinant polypeptides (HGF VEGF SDF-1 alpha and IGF-1).

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "repair" is meant to ameliorate damage or disease in a tissue or organ.

By "tissue" is meant a collection of cells having a similar morphology and function.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

BRIEF DESCRIPTION OF THE DRAWINGS

FIGS. 1A-1H are micrographs of epicardial stem/progenitor cells in vitro. FIG. 1A depicts an explant culture of right atrial appendage to generate feeder layer. FIG. 1B depicts the formation of floating spheroids and bunches of cells following switch to medium that favors the growth of stem/progenitor cells. FIG. 1C depicts maintenance of epicardial stem/progenitor cells with epithelial phenotype on uncoated dishes. FIG. 1D depicts epithelial to mesenchymal transformation (EMT) at 3 days following collection and transfer of floating cells (arrows: some cells do not undergo EMT and remain epithelial-like). FIG. 1E depicts epicardial cells with the epithelial phenotype expressing keratin proteins, while derived precursors express vimentin but not keratin. FIG. 1F-1H depict immunocytochemistry for transcription factors associated with cardiac development and repair: Epicardin, Nkx 2.5, GATA 4, respectively. FIG. 1P depicts epicardial cell monolayer 4 d after switching medium to adult stem/progenitor expansion medium. Note the formation of "bunches of grapes" due to epicardial progenitor-like cells adhering to each other and growing upward in the culture dish (within yellow dashes). In the isolation methods described herein, the bunches of progenitor cells pictured in FIG. 1P could be gathered and transferred to a medium containing 10% FCS to induce EMT.

FIGS. 2A-2M depict the expansion of atrial progenitor cells after epithelial to mesenchymal transformation (EMT). FIGS. 2A-2L are fluorescence micrographs of cells in culture. FIGS. 2A-2D depict expression of contractile proteins associated with cardiac myocytes: cardiac alpha actin (10×), cardiac alpha actin (40×), and phosphorylated myosin light chain (MCLPS20 and MLC2v). Note that cardiac alpha actin is not organized into mature sarcomeres. FIGS. 2E and 2F depict immunocytochemistry for markers of smooth muscle cells and endothelial cells: smooth muscle myosin (SMM) and von Willebrand Factor (vWF), respectively. Arrows indicate positive cells. FIGS. 2G and 2H depict the expression of gap junction proteins Cx40 and Cx43, respectively (arrows: Cx43 localization at membrane interaction between cells). FIGS. 2I and 2J depict the expression of the calcium binding protein Calsequestrin and the calcium ATPase SERCA2a, respectively. FIG. 2K shows that a subset of atrial progenitors express the MSC marker Stro-1 (arrow: positive cell; arrowhead: negative cell). FIG. 2L depicts non-specific mouse IgM staining control for immunocytochemistry experiments. FIG. 2M depicts results of a reverse transcriptase polymerase chain reaction (RT-PCR) for cardiac lineage mRNAs (cardiac alpha actin, MLC4, MLC2a, MLC2v, alpha SMA, vWF, Connexin 43, SERCA2a) derived from 3 human donors.

FIGS. 3A and 3B show results of FACS analysis for cell surface epitopes (Stro-1, CD 146, CD105, CD90, CD73, CD54, CD49d, CD44, CD31, CD29, CD24, c-kit, NG2, CD45, and CD34) in epicardial progenitors after epithelial to mesenchymal transformation (EMT) of two isolation procedures. Note that the expanding cell population was negative for CD45 and CD34 as well as c-kit. Many of the cells were positive for markers associated with MSCs: CD105, CD90, CD73, CD44, CD29 and Stro-1. In FIG. 3A, the green line represents the signal from cells (isolated using method#1) stained with isotype control antisera and the red line represents the signal from cells from the same culture stained with the specific antisera. In FIG. 3B, the red line represents the signal from cells (isolated using method#2) stained with isotype control antisera and the green line represents the signal from cells from the same culture stained with the specific antisera.

FIG. 4A shows that treatment with CdM significantly increases (improves) percent fractional shortening after MI compared to treatment with vehicle alone (alpha Minimum Essential Medium; alpha MEM) (* $p \leq 0.001$). FIG. 4B shows that treatment with CdM significantly increases the difference in left ventricle anterior wall thickness between diastole and systole compared to treatment with vehicle alone (alpha Minimum Essential Medium; alpha MEM) (* $p \leq 0.001$). FIG. 4C shows that treatment with CdM significantly decreases (improves) echocardiography scoring for wall motion compared to treatment with vehicle alone (alpha Minimum Essential Medium; alpha MEM) (** $p \leq 0.01$). (scale: ECHO score 13=Full wall motion; ECHO score 39=total akinesis). Sham operated mice underwent all procedures except that the suture was passed under the LAD and not tied; CdM or alpha MEM (vehicle control) was administered intra-arterially at the time of reperfusion after 4 hours of ischemia (Sham, n=2; CdM, n=8; alpha MEM, n=6).

FIG. 5A shows that treatment with CdM significantly decreases (improves) percent of myocardial infarction in the anterior wall of the left ventricle (LV) compared to treatment with vehicle alone (alpha Minimum Essential Medium; alpha MEM) (* $p \leq 0.001$). FIG. 5B shows that treatment with CdM significantly decreases (improves) total percentage of left ventricle with infarction compared to treatment with vehicle alone (alpha Minimum Essential Medium; alpha MEM) ( $p \leq 0.01$). Sham operated mice underwent all procedures except that the suture was passed under the LAD and not tied; CdM or alpha MEM (vehicle control) was administered intra-arterially at the time of reperfusion after 4 hours of ischemia (Sham, n=2; CdM, n=8; Alpha MEM, n=7).

FIG. 7A shows that treatment with CdM significantly increases (improves) percent fractional shortening after MI compared to treatment with vehicle alone (alpha Minimum Essential Medium; alpha MEM) ( $p \leq 0.01$). FIG. 7B shows that treatment with CdM significantly increases the difference in left ventricle anterior wall thickness between diastole and systole compared to treatment with vehicle alone (alpha Minimum Essential Medium; alpha MEM) ( $p \leq 0.01$). FIG. 7C shows that treatment with CdM significantly decreases (improves) echocardiography scoring for wall motion compared to treatment with vehicle alone (alpha Minimum Essential Medium; alpha MEM) (*** $p \leq 0.001$) (scale: ECHO score 13=Full wall motion; ECHO score 39=total akinesis). Sham operated mice underwent all procedures except that the suture was passed under the LAD and not tied; CdM or alpha MEM (vehicle control) was administered intra-arterially at the time of reperfusion after 4 hours of ischemia (Sham, n=2; CdM, n=7; Alpha MEM, n=7).

FIG. 8A shows that treatment with CdM significantly decreases end left ventricular diameter during systole (LVESD) compared to treatment with vehicle alone (alpha Minimum Essential Medium; alpha MEM) (** $p \leq 0.01$). FIG. 8B shows that treatment with CdM significantly decreases end left ventricular diameter during diastole (LVEDD) compared to treatment with vehicle alone (alpha Minimum Essential Medium; alpha MEM) (* $p \leq 0.05$). Sham operated mice underwent all procedures except that the suture was passed under the LAD and not tied; CdM or alpha MEM (vehicle control) was administered intra-arterially at the time of reperfusion after 4 hours of ischemia (Sham, n=2; CdM, n=7; Alpha MEM, n=7).

FIG. 3A depicts Gomori trichrome stains of representative histological sections from Alpha MEM-treated (left) and EPI CdM-treated (right) immunocompetent mice with MI. Arrowheads delineate extent of infarct. Scale bar=100 µM. FIG. 10B shows that treatment with CdM significantly decreases (improves) percent of myocardial infarction in the anterior wall of the left ventricle compared to treatment with vehicle alone (alpha Minimum Essential Medium; alpha MEM) (* p≤0.001). FIG. 10C shows that treatment with CdM significantly decreases (improves) total percentage of left ventricle with infarction compared to treatment with vehicle alone (alpha Minimum Essential Medium; alpha MEM) ( p≤0.01). Sham operated mice underwent all procedures except that the suture was passed under the LAD and not tied; CdM or alpha MEM (vehicle control) was administered intra-arterially at the time of reperfusion after 4 hours of ischemia. (Sham, n=2; CdM, n=5; Alpha MEM, n=7). FIG. 10D is a graph depicting percent fractional shortening in EPI CdM-treated compared with Alpha MEM (vehicle)-treated mice. FIG. 10E is a graph depicting echocardiography scoring for wall motion. Note: Full wall motion would score a 13; total akinesis would score a 39. FIG. 10F is a graph depicting end left ventricular diameter in systole (LVESD). FIG. 10G is a graph depicting cardiac output calculated from pulmonary arterial flow (Doppler measurement). EPI CdM or Alpha MEM (vehicle, MEM) was administered intra-arterially at the time of reperfusion after 4 hours of ischemia. Sham, n=2; EPI CdM, n=3; Alpha MEM, n=5. Note that for (d), Alpha MEM, n=4. * P≤0.05,  P≤0.01, * P≤0.001; compared with Alpha MEM. Error bars, SD.

FIG. 11 provides exemplary sequences of human epicardin (SEQ ID NO: 35), Nkx 2.5 (SEQ ID NO: 36), Isl-1 (SEQ ID NO: 42), GATA 5 (SEQ ID NO: 38), WT1 (SEQ ID NO: 41), Tbx18 (SEQ ID NO: 39), Tbx5 (SEQ ID NO: 40), GATA 4 (SEQ ID NO: 37), Mef2c (isoform 1 disclosed as SEQ ID NO: 43, isoform 2 disclosed as SEQ ID NO: 44), and myocardin (SEQ ID NO: 45) polypeptides.

FIGS. 12A 12F are micrographs. FIG. 12A shows immunohistochemical detection of single-stranded DNA (ssDNA) to detect apoptotic cells in positive control thymus tissue. Widespread apoptosis is present in the thymus of the dexamethasone (Dex)-treated mouse. FIG. 12B shows that apoptosis is minimal in hearts within the region of infarction at 24 hrs after MI with reperfusion. Arrow: Single apoptotic cell (ssDNA-positive). FIGS. 12C and 12D show representative TUNEL staining indicating widespread necrosis within regions of infarction for control Alpha MEM-treated mice at 24 hours after reperfusion. TUNEL-positive cells are green (FITC). FIGS. 12E and 12F show representative TUNEL staining demonstrating a significant reduction in the numbers of necrotic cells in mouse hearts treated with EPI CdM at the time of reperfusion compared with controls. FIG. 12G is a graph showing a quantification of TUNEL positive cells at 24 hours after MI with reperfusion. Alpha MEM, N=4; EPI CdM, N=3. Serial sections were cut to span the region of infarction. Six different sections spanning the region of infarction were quantified for each mouse heart.

FIG. 13A quantitates ELISA data showing the amount of HGF in unconcentrated 1× EPI CdMs of 5 human donors that range in age (52-80 yrs). FIG. 13B shows that regardless of donor age, 1× EPI CdM protects primary human aortic endothelial cells during simulated ischemia (1% oxygen for 24 hrs). GM: endothelial cell growth medium. Alpha MEM: low glucose base medium (CdM vehicle). FIGS. 13C-F show that antibody neutralization of HGF in 10× EPI CdM significantly reduced long-term (48 hr) protection of simulated ischemia for both primary aortic endothelial cells (FIGS. 13C and 13D) and primary human coronary artery endothelial cells (FIGS. 13E and 13F). IgG controls and HGF were both added to EPI CdM at 10 micrograms/ml. MTS assay measures cell metabolism. Cell numbers were determined by CyQuant assay (dye binding of nuclei acids). FIGS. 13G-13L are graphs showing that HGF pulldown from EPI CdM significantly reduced the benefits EPI CdM conferred on cardiac function at 1 wk after MI and reperfusion as determined by percent fractional shortening (FS, FIG. 13G), ECHO wall motion score (E score, h), and left ventricular end diameter in systole (LVESD, FIG. 13I). FIG. 13J is a graph showing that cardiac output measured from the pulmonary artery did not differ between mice with MI treated with HGF-PD compared with those that received IgG-PD. FIGS. 13K and 13L are graphs showing HGF pulldown from EPI CdM significantly reduced the amount of myocardial tissue preserved at 1 wk after MI and reperfusion. FIG. 13K is a graph depicting CK assay of anterior left ventricle wall (CK AW). FIG. 13K is a graph depicting CK assay of total left ventricle (CK total LV). Animal numbers (g-j): Sham, n=2; Alpha MEM, n=7; EPI CdM IgG-PD, n=8-9; EPI CdM HGF-PD, n=10. Animal numbers (k,l): Sham, n=2; Alpha MEM, n=8; EPI CdM IgG-PD, n=9; EPI CdM HGF-PD, n=10. * P≤0.05,  P≤0.01, * P≤0.001, NS=no significant difference. Error bars, SD.

FIG. 16A shows representative 1 cm slices from control and EPI CdM-treated hearts stained by TTC at 24 hrs after 1 hr of ischemia with reperfusion. Note that the non-viable (white) area in the control heart extends through the 3rd (bottom) section in both the LV and RV, while the infarct in the EPI CdM-treated heart does not. FIG. 16B shows that EPI CdM treatment significantly reduced infarct size at 24 hrs after MI (P=0.024, control vs. EPI CdM-treated, n=5 each). FIG. 16C shows islands of viable myocardium rescued in the apex of a heart treated with 25× EPI CdM (arrows). Error bars, SD of mean.

FIGS. 17A-17D are images depicting vascular integrity at 24 hrs after MI and reperfusion using extravasation of FITC-conjugated albumin (FITC-Alb) as an indicator. Note that areas of TUNEL staining for cardiac necrosis (FIG. 17B) correlate with areas containing FITC-Alb (see merge, FIG. 17D). Yellow arrows indicate TUNEL-positive cells (FIGS. 17B-17D). FIGS. 17E-17F show that at 24 hrs after reperfusion, hearts from Alpha MEM-treated control mice contained extensive extravasated FITC-Alb that was significantly decreased by EPI CdM treatment (EPI CdM IgG-PD). In contrast, simultaneous pulldown of HGF, VEGFA, and SDF-1 alpha (EPI CdM 3 GF PD) abrogated the ability of EPI CdM treatment to prevent vascular rhexis and associated cardiac tissue necrosis. Note that hearts from Sham-operated mice (pictured in FIG. 17E) did not contain areas of extravastated FITC-Alb and are therefore not represented in (FIG. 17F). Scale bars in FIG. 17E=50 µM. FIG. 17G is a graph depicting ELISA of serum PTX3 levels at 24 hrs after reperfusion as an independent measure of vascular rhexis. EPI CdM treatment (EPI CdM IgG-PD) significantly reduced the level of circulating PTX3, demonstrating prevention of vascular rhexis after reperfusion. In agreement with the determination of LV mural volumes containing FITC-Alb (FIG. 17F), mice treated with EPI CdM 3 GF PD have serum levels of PTX3 that did not differ from those of Alpha MEM-treated control mice. Animal numbers (FIG. 17F): Alpha MEM, n=4; EPI CdM IgG-PD, n=6; EPI CdM 3 GF PD, n=4. Animal numbers (FIG. 17G): Sham, n=3; Alpha MEM, n=5; EPI CdM IgG-PD, n=6; EPI CdM 3 GF PD, n=5. * P≤0.05, ** P≤0.01, t=no significant difference. Error bars, SD.

FIGS. 18A and 18B provide epifluorescent micrographs and Differential Interference Contrast (DIC) images that illustrate the high resolution of FITC-Alb assay. Merge in FIG. 18B demonstrates tagging of individual cardiac myocytes adjacent to FITC-negative myocytes. FIG. 18C shows extensive tissue necrosis within areas of myocardium that were positive for extravasated FITC-Alb as determined by TUNEL assays. Note that pink nuclei are positive for TUNEL staining Nuclei are shown by DAPI staining.

DETAILED DESCRIPTION OF THE INVENTION

Figure 1A:
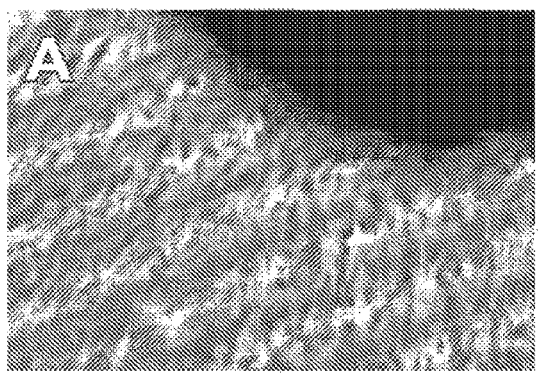
FIGS. 1A-1P depict the isolation of epicardial stem/progenitor cells.
Figure 1B:
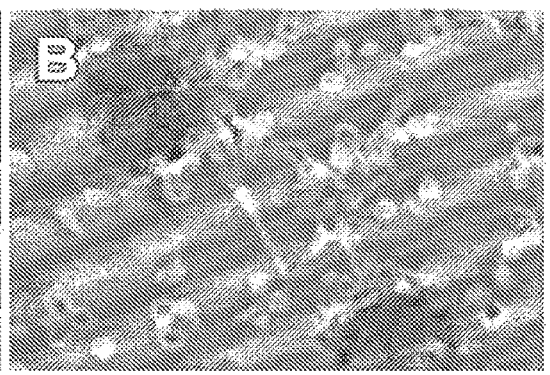
Figure 1C:
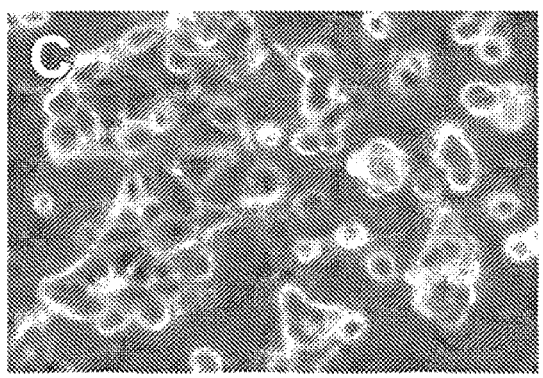

The invention features therapeutic compositions comprising agents secreted by epicardial progenitor cells and/or epicardial progenitor-derived mesenchymal stem cells and methods of using such compositions for the repair or regeneration of damaged cardiac tissue or heart.

The present invention is based, at least in part, on the discoveries that media isolated from epicardial progenitor cells or epicardial progenitor-derived mesenchymal stem (EPI CdM) preserved cardiac function, reduced cell death, reduced inflammatory responses, and promoted healing of injured tissues and prevention of vascular rhexis in the mice when administered intra-arterially to mice after prolonged myocardial ischemia (4 hours) with reperfusion. Without intending to be bound to theory, EPI CdM treatment rapidly reduces myocardial necrosis and infarct expansion after MI by preventing the progression of vascular rhexis that occurs following reperfusion. Treatment using EPI Cdm provides advantages over cell-based therapies, which involve invasive isolation procedures, lack of available autologous materials, or the requirement for MHC-matching. Unexpectedly and surprisingly, EPI CdM from patients of advanced age did not reduce the ability of EPI CdM to provide cardioprotection or vasoprotection.

Accordingly, the invention provides therapeutic and prophylactic compositions comprising agents secreted by epicardial progenitor cells and/or epicardial progenitor-derived mesenchymal stem cells (e.g., HGF VEGF SDF-1 alpha and IGF-1) and methods of using such compositions to reduce cardiac cell death, preserve cardiac function after an ischemic event, and to generally prevent cardiac damage and promote cardiac healing or regeneration.

Epicardial Progenitor Cells

The epicardium is a specialized epithelial cell layer that covers the heart and is important in maintaining cardiac structure and function (Gittenberger-de Groot et al., Circ Res. 2000; 87:969-971; Eralp et al., Circ Res. 2005; 96:526-534). During cardiac development, a subset of epicardial cells undergo epithelial to mesenchymal transformation, invade the underlying subepicardium and myocardium, and contribute to the interstitial fibroblasts and the subepicardial and coronary vasculature (Dettman et al., Dev Biol. 1998; 193:169-181; Vrancken Peeters et al., Anat Embryol (Berl). 1999; 199:367-378; Perez-Pomares et al., Int J Dev Biol. 2002; 46:1005-1013; Reese et al., Circ Res. 2002; 91:761-768). Recent genetic lineage tracing studies have demonstrated that epicardial progenitor cells also contribute extensively to the cardiac myocyte pool (Cai et al., Nature. 2008; 454:104-108). The dramatic cardiac regeneration that occurs in adult zebrafish after ventricular injury depends upon on epicardial cell proliferation, epithelial-to-mesenchymal transition, invasion and subsequent neovascularization of myocardium (Lepilina et al., Cell. 2006; 127:607-619). Because of their ability to respond to injury and to differentiate into multiple cardiac cell types (Limana et al., Circ Res. 2007; 101:1255-1265), epicardial cells and their derivatives can be considered as a potential source of post-natal cardiac stem/progenitor cells for regenerative medicine (Wessels et al., Anat Rec A Discov Mol Cell Evol Biol. 2004 January; 276(1):43-57; Winter et al., Circulation. 2007; 116:917-927).

Isolation of Cells

While the results reported herein provide specific examples of the isolation of epicardial progenitor cells from right atrial appendages, the invention is not so limited. The unpurified source of cells for use in the methods of the invention may be any cells or tissue capable of giving rise to epicardial progenitor cells, embryonic stem cells, and induced pluripotent cells (Wernig et al. Nature 19; 448 (7151):318-24, 2007). Preferably, cells of the invention are epicardial progenitor cells selected for expression of epicardin, Nkx 2.5, Isl-1, GATA 5, WT1, Tbx18, and Tbx5 transcription factors. In various embodiments, the epicardial progenitor cells are selected for expression of one or more of a cell surface marker (e.g., $CD105^+$, $CD90^+$, $CD73^+$, $CD44^+$, $CD29^+$, and Stro-1) prior to selection for expression of an internal marker (e.g., epicardin, Nkx 2.5, Isl-1, GATA 5, WT1, Tbx18, Tbx5, GATA 4, Mef2c, and/or myocardin). Various techniques can be employed to separate or enrich for the desired cells. Such methods include a positive selection for cells expressing these markers. Monoclonal antibodies are particularly useful for identifying markers associated with the desired cells. If desired, negative selection methods can be used in conjunction with the methods of the invention to reduce the number of irrelevant cells present in a population of cells selected for epicardin, Nkx 2.5, Isl-1, GATA 5, WT1, Tbx18, and Tbx5 expression. For example, epicardial progenitor cells may be negatively selected for hematopoietic cell surface markers such as CD34, CD45, c-kit, and the vascular pericyte marker NG2.

In one approach, epicardial progenitor cells are isolated by the selective culture of cells obtained from cardiac tissue (e.g., right atrial appendage) in medium favoring stem/progenitor cell growth (e.g., DMEM/F12 (Invitrogen) with 3% FCS (Atlanta Biologicals) and 20 ng/ml epidermal growth factor (EGF), 10 ng/ml basic fibroblast growth factor (bFGF), 10 ng/ml leukocyte migration inhibitory factor (LIF) (all growth factors from Sigma, Saint Louis, Mo.), 1×1× insulin, transferrin, selenium (ITS plus) (BD Biosciences, San Jose, Calif.), 100 units/ml penicillin, 100 µg/ml streptomycin, and 2 mM L-glutamine (Mediatech Inc.). In mixed cell cultures, epicardial progenitor cells are distinguishable by their morphology and pattern of growth (e.g., epicardial progenitor cells do not readily mix with other cells in culture; epicardial progenitor cells form spheroids or clusters of spheriods that proliferate upwards into the medium rather than horizontally). Epicardial progenitor cells can be collected from mixed cultures by shaking the culture to release the loosely adherent aggregates and spheroids of stem/progenitor cells.

Other procedures that may be used for selection of cells of interest include, but are not limited to, density gradient centrifugation, flow cytometry, magnetic separation with antibody-coated magnetic beads, affinity chromatography, cytotoxic agents joined to or used in conjunction with a mAb, including, but not limited to, complement and cytotoxins; and panning with antibody attached to a solid matrix or any other convenient technique. The cells can be selected against dead cells, by employing dyes associated with dead cells such as propidium iodide (PI). Preferably, the cells are collected in a medium comprising (alpha MEM), fetal calf serum (FCS), or bovine serum albumin (BSA) or any other suitable, preferably sterile, isotonic medium. Selected cells of the invention may be employed for the isolation of secreted cellular factors as described herein.

In one embodiment, selected cells of the invention comprise a purified population of epicardial progenitor cells selected for expression of epicardin, Nkx 2.5, Isl-1, GATA 5, WT1, Tbx18, and Tbx5. Those skilled in the art can readily determine the percentage of cells in a population using various well-known methods, such as fluorescence activated cell sorting (FACS). Preferable ranges of purity in populations comprising selected cells are about 50 to about 55%, about 55 to about 60%, and about 65 to about 70%. More preferably the purity is at least about 70%, 75%, or 80% pure, more preferably at least about 85%, 90%, or 95% pure. In some embodiments, the population is at least about 95% to about 100% selected cells.

The selected cells may be grown in culture for hours, days, or even weeks during which time their culture medium becomes enriched in one or more secreted cellular factors that support cardiac progenitor cell proliferation, reduce cardiac cell death, preserve cardiac function after an ischemic event, prevent or reduce cardiac damage, increase cardiac function, increase cardiac healing or increase cardiac regeneration. Media enriched for such biologically active agents is termed "conditioned media."

Media and reagents for tissue culture are well known in the art (see, for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Examples of suitable media for incubating mesenchymal stem cells or multipotent stromal cells samples include, but are not limited to, Dulbecco's Modified Eagle Medium (DMEM), RPMI media, Hanks' Balanced Salt Solution (HBSS) phosphate buffered saline (PBS) and other media known in the art. Examples of appropriate media for culturing cells of the invention include, but are not limited to, Dulbecco's Modified Eagle Medium (DMEM), RPMI media. The media may be supplemented with fetal calf serum (FCS) or fetal bovine serum (FBS) as well as antibiotics, growth factors, amino acids, inhibitors or the like, which is well within the general knowledge of the skilled artisan.

If desired, the epicardial progenitor cells or their progeny is cultured under conditions that maintain the cells in a proliferative state. In one embodiment, the cells are immortalized to enhance their proliferation. Methods for immortalizing a cell are known in the art and include, but are not limited to, expressing in the cell one or more of dominant negative p53, telomerase, beta catenin, notch and/or a transcription factor or other polypeptide that promotes cell proliferation (e.g., stem cell proliferation). The aforementioned polypeptides may be expressed using any vector suitable for expression in an epicardial progenitor cell (e.g., a viral vector).

Formulations

In one embodiment, a composition of the invention comprises or consists essentially of one or more cellular factors isolated from selected epicardial progenitor cells or their progeny. In particular embodiments, the cellular factor is secreted by an epicardial progenitor cell selected for expression of epicardin, Nkx 2.5, GATA 4, Mef2c, and myocardin polypeptides, polynucleotides, or the cellular progeny of a selected cell. Such cells are cultured according to any method known in the art. In another embodiment, a composition of the invention comprises conditioned media obtained during the culture of such cells that contains one or more biologically active agents secreted by a cell of the invention. If desired, the secreted cellular factors are at least partially purified (e.g., at least about 10%, 25%, 30%, 50%, 75%, 80%, 90%, or 95%) to remove undesired agents present in the culture media. In one embodiment, one or more identified cellular factors (e.g., HGF, VEGF, SDF-1 alpha, and/or IGF-1) is expressed recombinantly and used to supplement a composition of the invention. The biologically active agents present in the condition media, the cells, or a combination thereof, can be conveniently provided to a subject as sterile liquid preparations, e.g., isotonic aqueous solutions, suspensions, emulsions, dispersions, or viscous compositions, which may be buffered to a selected pH. Cells and agents of the invention may be provided as liquid or viscous formulations. For some applications, liquid formations are desirable because they are convenient to administer, especially by injection. Where prolonged contact with a tissue is desired, a viscous composition may be preferred. Such compositions are formulated within the appropriate viscosity range. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions are prepared by compositions comprising a secreted cellular factor isolated from cultures of epicardial progenitor cells in the required amount of the appropriate solvent with various amounts of the other ingredients, as desired. Such compositions may be in admixture with a suitable carrier, diluent, or excipient, such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like.

Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells or agents present in their conditioned media.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent, such as methylcellulose. Other suitable thickening agents include, for example, xanthan gum, carboxymethyl cellulose, hydroxypropyl cellulose, carbomer, and the like. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form). Those skilled in the art will recognize that the components of the compositions should be selected to be chemically inert.

Compositions comprising secreted cellular factors present in conditioned media (e.g., from the culture of epicardial progenitor cells and/or epicardial progenitor derived mesenchymal cells) are also administered in an amount required to achieve a therapeutic or prophylactic effect. Such an amount will vary depending on the conditions of the culture. Typically, biologically active cellular factors present in the conditioned media will be purified and subsequently concentrated so that the protein content of the composition is increased by at least about 5-fold, 10-fold or 20-fold over the amount or protein originally present in the media. In other embodiments, the protein content is increased by at least about 25-fold, 30-fold, 40-fold or even by 50-fold. Preferably, the composition comprises an effective amount of a cellular factor isolated from an epicardial progenitor cell and/or an epicardial progenitor derived mesenchymal cell.

The precise determination of what would be considered an effective dose is based on factors individual to each subject, including their size, age, sex, weight, and condition of the particular subject. Dosages can be readily ascertained by those skilled in the art from this disclosure and the knowledge in the art.

Optionally, the methods of the invention provide for the administration of a composition of the invention to a suitable animal model to identify the dosage of the composition(s), concentration of components therein and timing of administering the composition(s), which elicit tissue repair, reduce cell death, or induce another desirable biological response. Such determinations do not require undue experimentation, but are routine and can be ascertained without undue experimentation.

Methods of Delivery

Compositions comprising one or more cellular factors (e.g., HGF VEGF SDF-1 alpha and IGF-1) present in conditioned media (e.g., agents isolated from a culture of epicardial progenitor cells selected for expression of epicardin, Nkx 2.5, GATA 4, Mef2c, and/or myocardin are provided systemically or directly to a desired site (e.g., a site of tissue damage or ischemic injury). Modes of administration include intramuscular, intra-cardiac, oral, rectal, topical, intraocular, buccal, intravaginal, intracisternal, intra-arterial, intracerebroventricular, intratracheal, nasal, transdermal, within/on implants, e.g., fibers such as collagen, osmotic pumps, or parenteral routes. The term "parenteral" includes subcutaneous, intravenous, intramuscular, intraperitoneal, intragonadal or infusion.

The isolated cellular factors can be administered via localized injection, including catheter administration, systemic injection, localized injection, intravenous injection, or parenteral administration. When administering a therapeutic composition of the present invention, it will generally be formulated in a unit dosage injectable form (solution, suspension, emulsion). Dosages can be readily adjusted by those skilled in the art (e.g., a decrease in purity may require an increase in dosage). Compositions of the invention can be introduced by injection, catheter, or the like. Compositions of the invention include pharmaceutical compositions comprising cellular factors of the invention and a pharmaceutically acceptable carrier. Administration can be autologous or heterologous. For example, epicardial progenitor cells selected for expression of epicardin, Nkx 2.5, Isl-1, GATA 5, WT1, Tbx18, and Tbx5 can be obtained from one subject, and the CdM from the culture of such cells administered to the same subject or a different, compatible subject.

If desired, biologically active agents present in conditioned media are incorporated into a polymer scaffold to promote tissue repair, cell survival, proliferation in a tissue in need thereof. Polymer scaffolds can comprise, for example, a porous, non-woven array of fibers. The polymer scaffold can be shaped to maximize surface area, to allow adequate diffusion of nutrients and growth factors to a cell of the invention. Polymer scaffolds can comprise a fibrillar structure. The fibers can be round, scalloped, flattened, star-shaped, solitary or entwined with other fibers. Branching fibers can be used, increasing surface area proportionately to volume.

Unless otherwise specified, the term "polymer" includes polymers and monomers that can be polymerized or adhered to form an integral unit. The polymer can be non-biodegradable or biodegradable, typically via hydrolysis or enzymatic cleavage. The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo(ε-caprolactone)diol as switching segment/oligo(p-dioxyanone)diol as physical crosslink. Other suitable polymers can be obtained by reference to The Polymer Handbook, 3rd edition (Wiley, N.Y., 1989).

Screening Assays

The invention provides methods for identifying cellular factors present in the conditioned media of a cell of the invention (e.g., an epicardial progenitor cell selected for expression of epicardin, Nkx 2.5, Isl-1, GATA 5, WT1, Tbx18, and Tbx5). Such agents include proteins, peptides, polynucleotides, small molecules or other agents that enhance tissue repair or increase cardiac function. Agents thus identified can be used to enhance tissue repair by modulating, for example, the proliferation, survival, or differentiation of cells of the tissue of interest. In one embodiment, agents identified according to a method of the invention reduce apoptosis.

The test agents of the present invention can be obtained singly or using any of numerous approaches. Such methods will typically involve contacting a population of cells at risk of cell death with a test agent isolated from conditioned media and measuring an increase in survival or a reduction in cell death as a result of the contact. Comparison to an untreated control can be concurrently assessed. Where an increase in the number of surviving cells or a reduction in cell death is detected relative to the control, the test agent is determined to have the desired activity.

Fractionation of the conditioned media will be necessary to isolate one or more cellular factors having a desired biological activity. Thus, the goal of the extraction, fractionation, and purification process is the careful characterization and identification of a chemical entity within the conditioned media having the desired biological activity. Methods of fractionation and purification of heterogenous extracts are known in the art. If desired, peptides, polynucleic acids, or small compounds shown to be useful agents for enhancing tissue repair are chemically modified according to methods known in the art. Such agents may be characterized for biological activity in using methods known in the art, including animal models of tissue injury and disease (e.g., myocardial infarction, hind limb ischemia, and stroke).

Once identified, agents having a desired biological activity (e.g., cardioprotective activity) may be recombinantly expressed and used to supplement a therapeutic or prophylactic composition described herein (e.g., conditioned media).

Methods for Evaluating Therapeutic Efficacy

In one approach, the efficacy of the treatment is evaluated by measuring, for example, the biological function of the treated organ (e.g., cardiac cell function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is cardiac tissue and, preferably, the organ is heart.

In another approach, the therapeutic efficacy of the methods of the invention is assayed by measuring an increase in cell number in the treated or transplanted tissue or organ as compared to a corresponding control tissue or organ (e.g., a tissue or organ that did not receive treatment). Preferably, cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif.). For example, assays for cell proliferation may involve the measurement of DNA synthesis during cell replication. In one embodiment, DNA synthesis is detected using labeled DNA precursors, such as [$^3$H]-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302(5650):1581-4, 2003; Gu et al., Science 302 (5644):445-9, 2003).

In another approach, efficacy is measured by detecting an increase in the number of viable cells present in a tissue or organ relative to the number present in an untreated control tissue or organ, or the number present prior to treatment. Assays for measuring cell viability are known in the art, and are described, for example, by Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 0.1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo Luminescent Cell Viability Assay, which is a lactate dehyrodgenase (LDH) cytotoxicity assay (Promega).

Alternatively, or in addition, therapeutic efficacy is assessed by measuring a reduction in apoptosis. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Methods for Evaluating Cardiac Function

Compositions of the invention may be used to enhance cardiac function in a subject having reduced cardiac function. Methods for measuring the biological function of the heart (e.g., contractile function) are standard in the art and are described, for example, in the Textbook of Medical Physiology, Tenth edition, (Guyton et al., W.B. Saunders Co., 2000). In the invention, cardiac function is increased by at least 5%, 10%, 15%, 20%, 30%, 40%, 50%, 60%, 70%, 80%, 90%, or even 100% relative to the cardiac function present in a naturally-occurring, corresponding tissue or organ. Most advantageously, cardiac function is enhanced or damage is reversed, such that the function is substantially normal (e.g., 85%, 90%, 95%, or 100% of the cardiac function of a healthy control subject). Reduced cardiac function may result from conditions such as cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy (e.g., hypertrophic cardiomyopathy originating from a genetic or a secondary cause), post ischemic and post-infarction cardiac remodeling and cardiac failure.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular end-systolic volume) by an imaging method such echocardiography, nuclear or radiocontrast ventriculography, or magnetic resonance imaging, and systolic tissue velocity as measured by tissue Doppler imaging. Systolic contractility can also be measured non-invasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echoDoppler measurements). Other measures of cardiac function include myocardial contractility, resting stroke volume, resting heart rate, resting cardiac index (cardiac output per unit of time [L/minute], measured while seated and divided by body surface area [$m^2$])) total aerobic capacity, cardiovascular performance during exercise, peak exercise capacity, peak oxygen ($O_2$) consumption, or by any other method known in the art or described herein. Measures of vascular function include determination of total ventricular afterload, which depends on a number of factors, including peripheral vascular resistance, aortic impedance, arterial compliance, wave reflections, and aortic pulse wave velocity, Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X ray contrast ventriculography, nuclear imaging ventriculography, computed tomography imaging, rapid spiral computerized tomographic imaging, 3-D echocardiography, invasive cardiac pressures, invasive cardiac flows, invasive cardiac pressure-volume loops (conductance catheter), non-invasive cardiac pressure-volume loops.

Kits

Compositions comprising a cell of the invention (e.g., an epicardial progenitor cell selected for expression of epicardin, Nkx 2.5, Isl-1, GATA 5, WT1, Tbx18, and Tbx5) or a composition comprising biologically active agents (e.g., HGF VEGF SDF-1 alpha and IGF-1) present in conditioned media of such cells is supplied along with additional reagents in a kit. The kits can include instructions for the treatment regime, reagents, equipment (test tubes, reaction vessels, needles, syringes, etc.) and standards for calibrating or conducting the treatment. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Isolated Cardiac Progenitor Cells are Capable of Epithelial to Mesenchymal Transformation when Expanded in Conditioned Media Adult human atrial stem/progenitor cells were isolated from right atrial biopsies. The right atrial appendage, commonly removed to install a cardiopulmonary pump during bypass surgery, provided ample material to isolate atrial stem/progenitor cells from 11 out of 12 donors. Adult human atrial stem/progenitor cells were successfully isolated from 12 out of 13 donors (Table 1).

TABLE 1

Patient Data for Epicardial Progenitor Cell Isolations.

| Sex | Age | HTN | DM | CAD | MR | AS | LVEF |
|-----|-----|-----|----|----|----|----|------|
| M | 47 | + | + | + | − | − | 0.45 |
| M | 59 | + | − | + | − | − | NI |
| M | 57 | − | − | + | − | − | NI |
| M | 52 | − | − | − | + | − | NI |
| M | 57 | − | − | + | − | − | NI |
| F | 53 | + | − | + | − | − | NI |
| M | 80 | + | − | − | − | + | NI |
| F | 72 | + | − | − | + | − | 0.45 |
| M | 53 | + | + | + | − | − | NI |
| M | 78 | − | − | + | − | − | NI |
| F | 72 | + | − | + | − | − | NI |
| F | 60 | + | − | + | − | − | NI |

Abbreviations:
HTN, hypertension;
DM, diabetes mellitus;
CAD, coronary artery disease;
MR, mitral regurgitation;
AS, aortic stenosis;
LVEF, left ventricular ejection fraction.

Right atrial appendages were obtained from consenting cardiac bypass patients according to an Institutional Review Board (IRB) protocol that was approved by the University of Vermont (UVM). The appendages were transferred from the hospital to the UVM Stem Cell Core on ice in 50 ml conical tubes containing explant medium: alpha MEM (Invitrogen, Carlsbad, Calif.), 10% fetal calf serum (FCS) (lot selected for rapid growth of hMSCs, Atlanta Biologicals, Lawrenceville, Ga.), 100 units/ml penicillin, 100 μg/ml streptomycin, and 2 mM L-glutamine (Mediatech Inc., Hendron, Va.). In the cell culture hood, the tissue was immediately rinsed in phosphate buffered saline (1×PBS) and any extracardiac fat was manually removed with fine scissors. The remaining tissue was transferred to a 100 cm$^2$ dish (Nunc, Thermo Fisher Scientific, Rochester, N.Y.) containing phosphate buffered saline (1×PBS) supplemented with 1 mg/mL collagenase/dispase (Roche Applied Science, Indianapolis, Ind.). The tissue was minced into approximately 1 mm$^3$ pieces using sterile scalpel blades (#23, World Precision Instruments, Sarasota, Fla.). The dish was placed into a sterile 37° C. humidified cell culture incubator (Thermo Forma, 5% $CO_2$) for 1.5 hours, with shaking every 10 minutes. The resulting tissue digest was collected and centrifuged at 600×g for 5 minutes. The pellet was resuspended and washed in 25 mls of explant medium and centrifuged again. The final pellet was resuspended in 20 ml of explant medium and the digested fragments were split between 2 uncoated 100 cm$^2$ dishes. After 2-3 days, the dishes were supplemented by the addition of 5 ml of explant medium and then left undisturbed to allow for the adherence of tissue fragments. Following 5-7 days, when fibroblast/endothelial outgrowth from the explants had almost reached confluence, the dishes were washed once with phosphate buffered saline (1×PBS) and the explant medium was changed to a medium that favored stem/progenitor cell growth: DMEM/F12 (Invitrogen) with 3% FCS (Atlanta Biologicals) and 20 ng/ml epidermal growth factor (EGF), 10 ng/ml basic fibroblast growth factor (bFGF), 10 ng/ml leukocyte migration inhibitory factor (LIF) (all growth factors from Sigma, Saint Louis, Mo.), 1× insulin, transferrin, selenium (ITS plus) (BD Biosciences, San Jose, Calif.), 100 units/ml penicillin, 100 μg/ml streptomycin, and 2 mM L-glutamine (Mediatech Inc.). After 2-3 days, areas of stem/progenitor cells were observed proliferating in between the fibroblasts/endothelial cells.

The stem/progenitor cells were distinguishable by morphology. They did not mix with the other cells in the dishes, and formed spheroids and "bunches of grapes" as they divided upwards into the medium rather than horizontally. By shaking the dishes and washing once with calcium- and magnesium-free PBS, the loose aggregates and spheroids of stem/progenitor cells were collected, centrifuged at 600×g for 5 minutes, resuspended in Claycomb expansion medium (SAFC Biosciences, Sigma) with 10% fetal calf serum (FCS), 100 units/ml penicillin, 100 μg/ml streptomycin, and 2 mM L-glutamine, and transferred to new dishes. Following adherence to culture plastic, the majority of the atrial stem/progenitor cells underwent epithelial to mesenchymal transformation (EMT) into mesodermal progenitors and precursor cells as they expanded in the high serum medium.

Figure 1D:
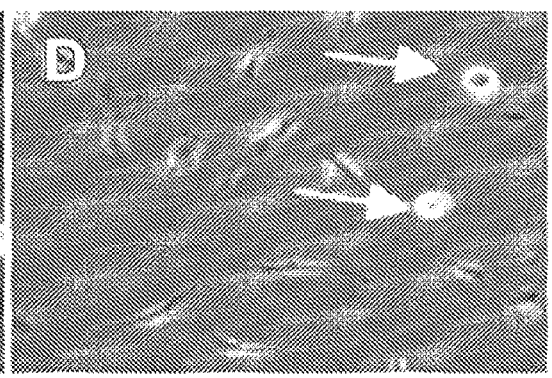
Figure 1E:
Figure 1F:
Figure 1G:
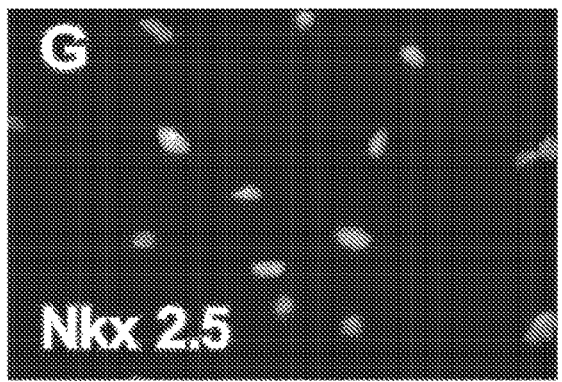
Figure 1H:
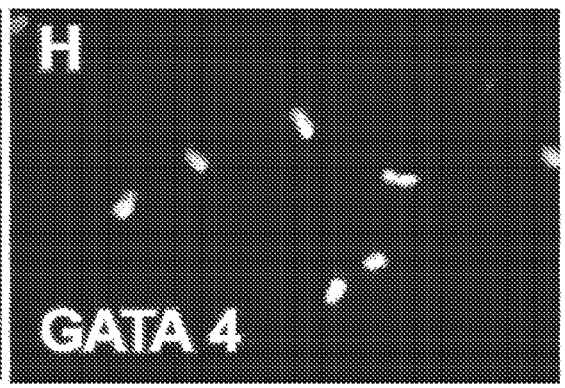
Figure 1I:
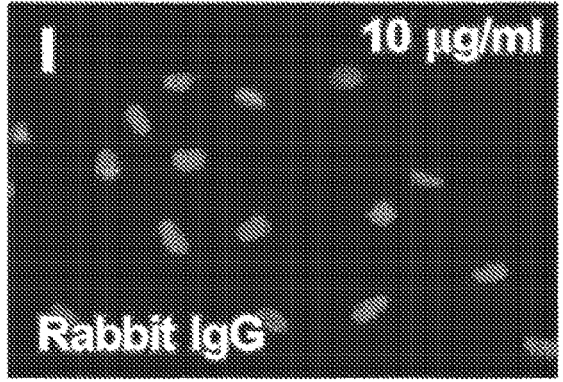
FIGS. 1I and 1J depict non-specific Rabbit IgG and non-specific Mouse IgG staining controls, respectively, for immunocytochemistry experiments.
Figure 1J:
Figure 1L:
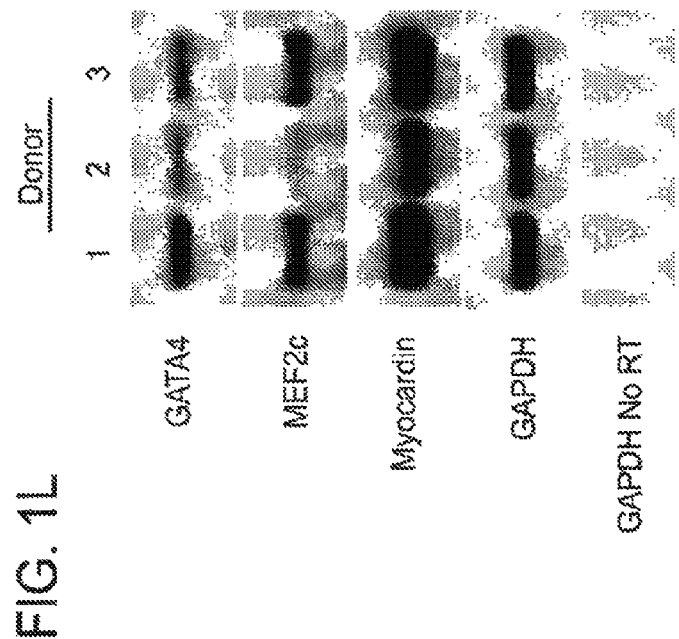
FIG. 1L shows an analysis of mRNA expression in epicardially-derived precursor cells derived from 3 human donors (passage 0) using reverse transcriptase polymerase chain reaction (RT-PCR) for cardiac transcription factors (GATA 4, MEF2c, and myocardin).
Figure 1K:
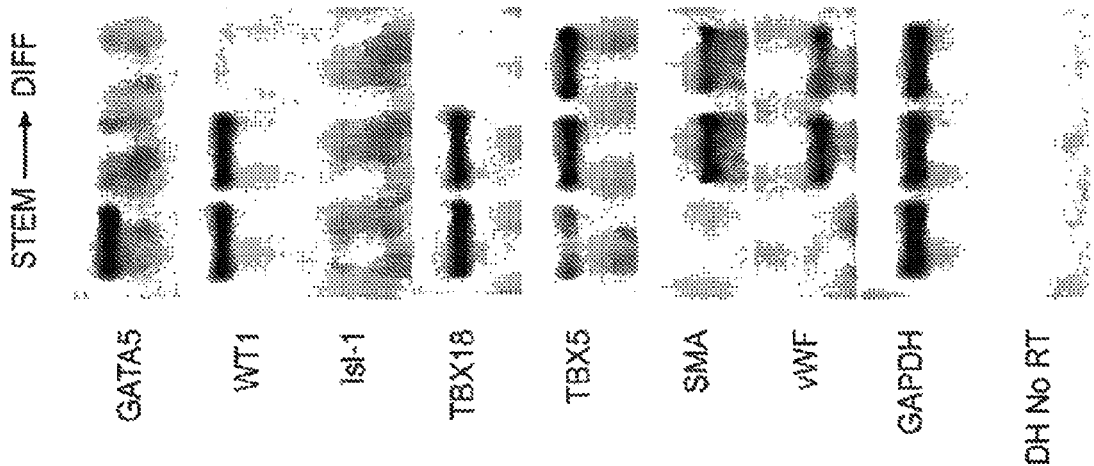
FIG. 1K shows an analysis of mRNA expression using reverse transcriptase polymerase chain reaction (RT-PCR). Several transcription factors associated with cardiac development are downregulated during differentiation while others such as smooth muscle actin (SMA) and von Willebrand Factor (vWF) are upregulated. Left lane shows amplification from RNA of cells from stem cells (e.g., as shown in FIG. 1C). Center and right lanes show amplification of RNA from cells after 1 and 2 weeks of culture on coated cellware. Note: the lower diffuse bands in the gel data for GATA5, Isl-1, and Tbx5 are primer dimers.
Figure 1M:
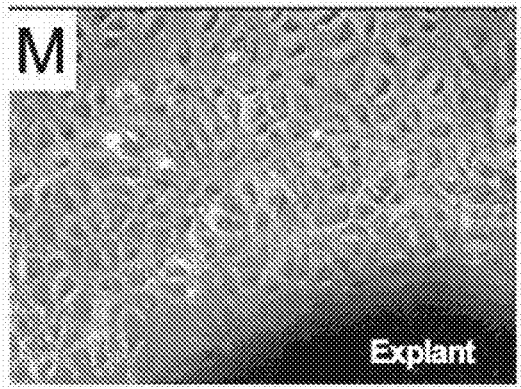
FIG. 1M depicts epicardial cell outgrowth from epicardial explant generated by dissecting surface epicardial cell layer from right atrial appendage removed during bypass surgery. Outgrowth occured over 7 d. Note epithelial morphology of cell monolayer.
Figure 1N:
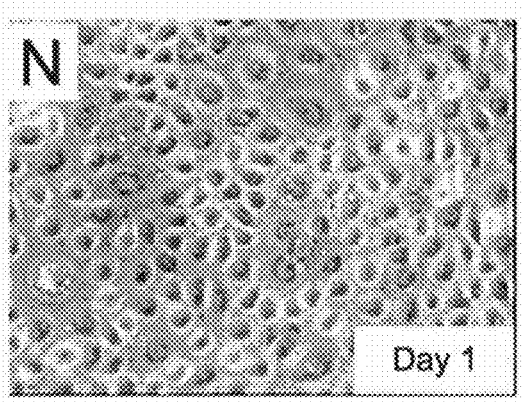
FIG. 1N depicts epicardial cell monolayer 1 d after switching medium to adult stem/progenitor expansion medium (see Methods).
Figure 1O:
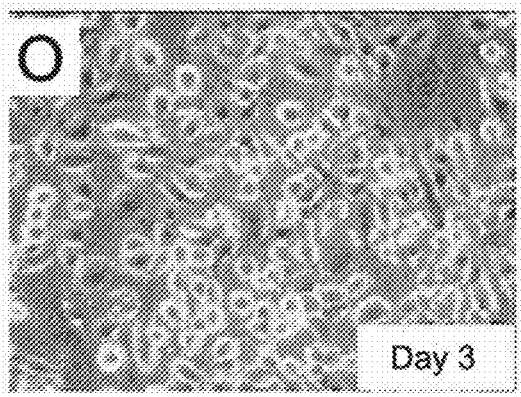
FIG. 1O depicts epicardial cell monolayer 3 d after switching medium to adult stem/progenitor expansion medium. Note refractile cells beginning to round up.
Figure 1P:
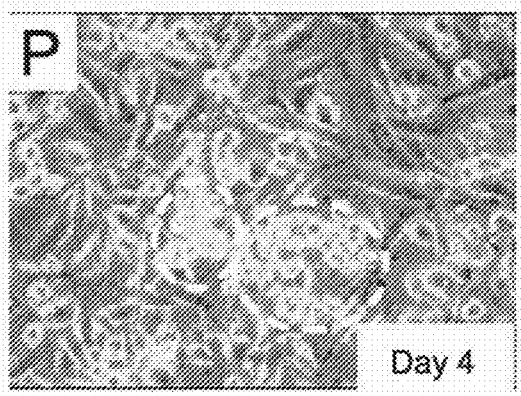
Figure 2A:
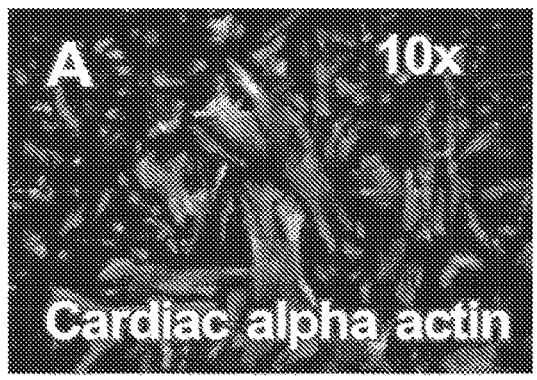
Figure 2B:
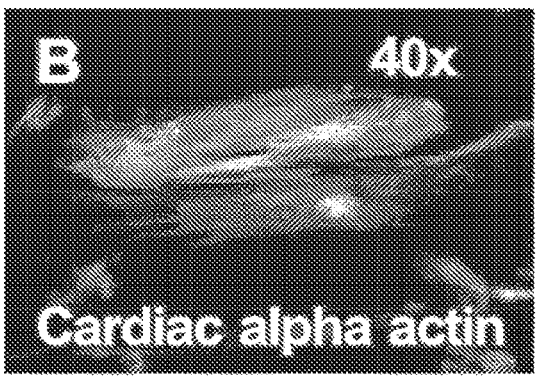
Figure 2C:
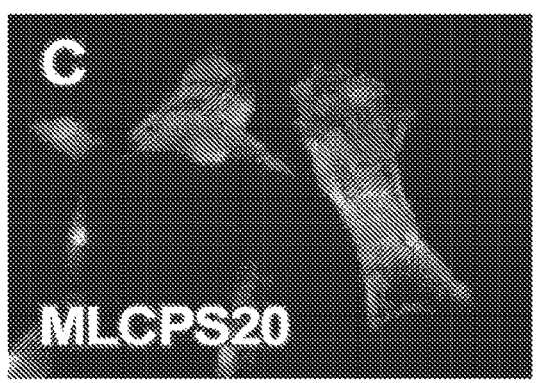
Figure 2D:
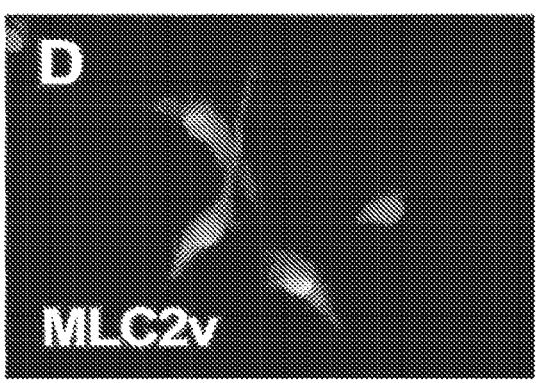
Figure 2E:
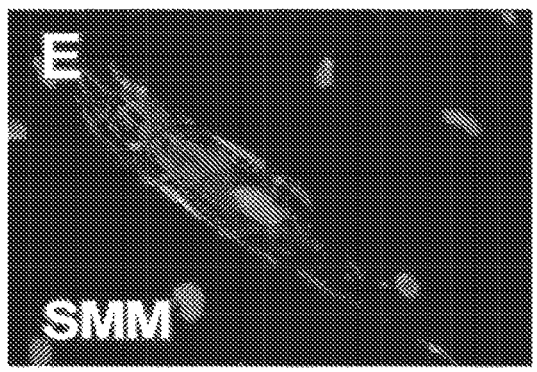
Figure 1F:
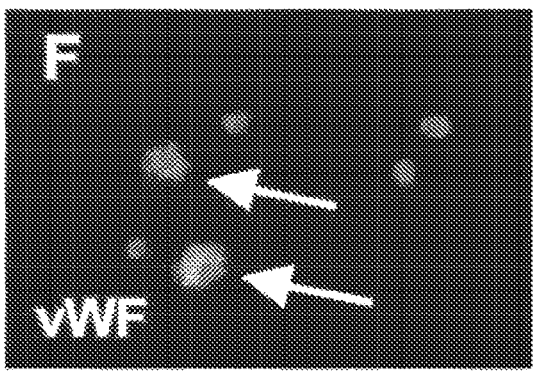
Figure 2G:
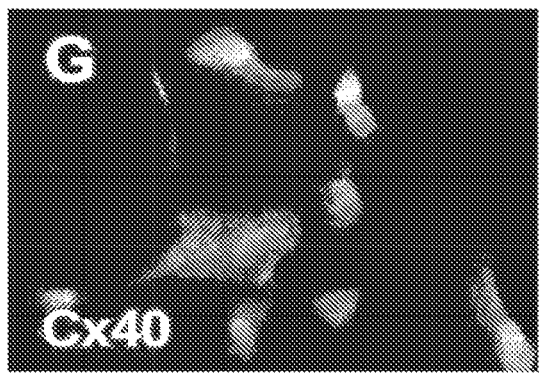
Figure 2H:
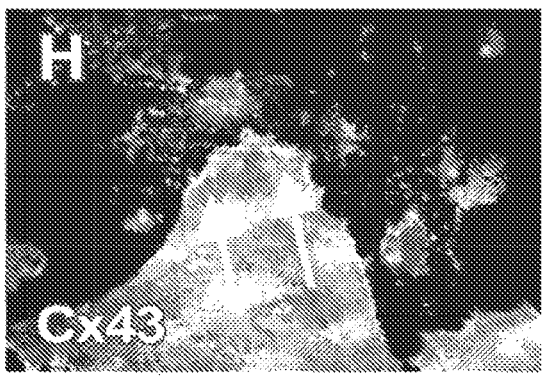
Figure 2I:
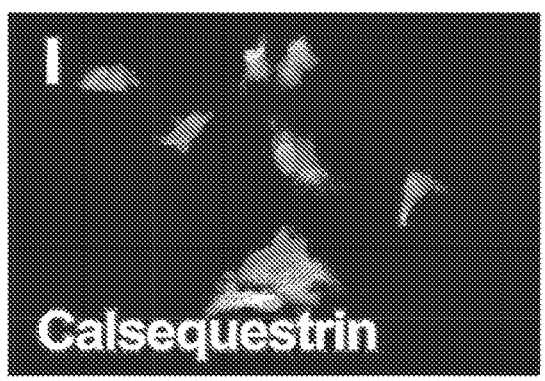
Figure 2J:
Figure 2K:
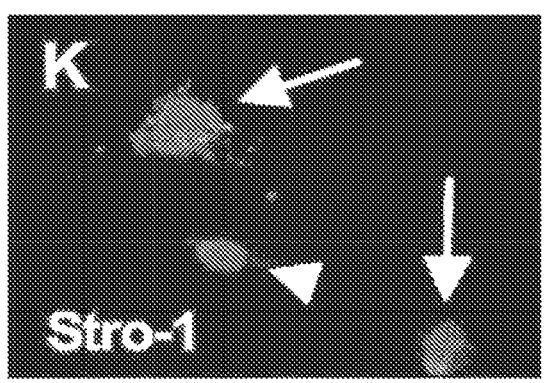
Figure 2L:
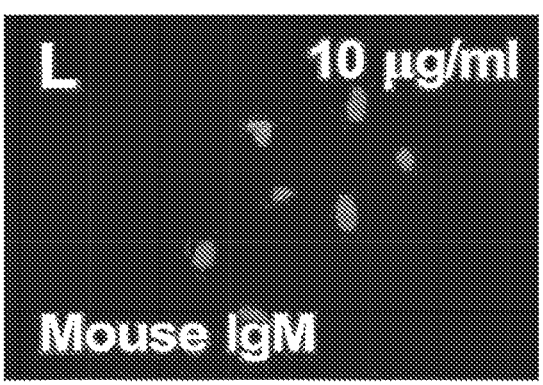
Figure 2M:
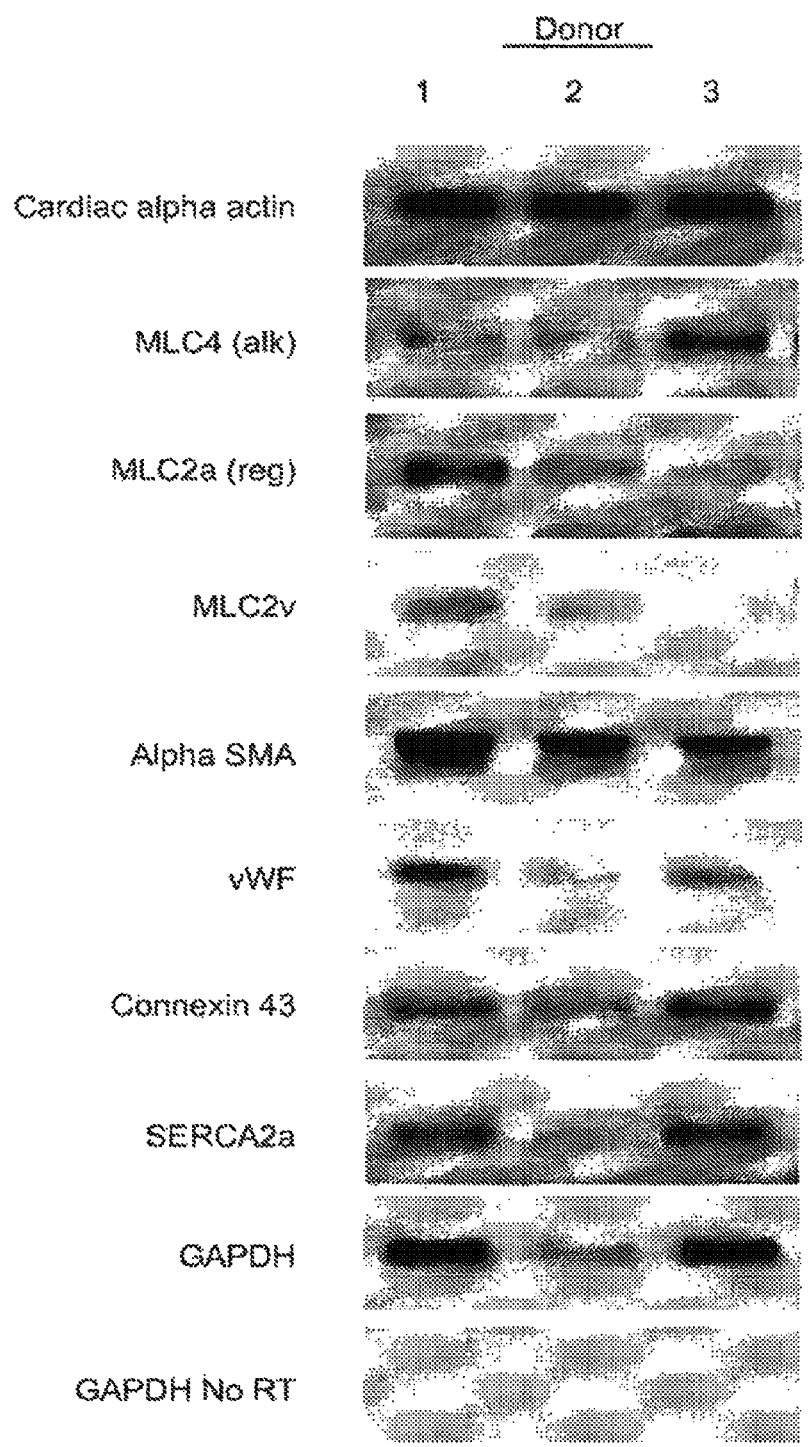

The isolation method yielded relatively pure cultures of proliferating epicardial progenitor cells that expressed markers of epicardial and cardiac stem/progenitor cells such as epicardin, Nkx 2.5, Isl-1, GATA 5, WT1, Tbx18, and Tbx5 (FIGS. 1A-1L). The epicardial stem/progenitor cells could be maintained as undifferentiated epithelial cultures on uncoated polystyrene dishes in stem/progenitor cell medium (FIG. 1C) or could be made to undergo EMT into mixtures of transit-amplifying precursor cells after plating onto charged or coated cell ware in medium containing 10% fetal calf serum (FIG. 1D). The expression levels of mRNAs for several transcription factors decreased as the cells differentiated (see GATA5, WT1, Isl-1, and Tbx18; FIG. 1K). In contrast, the expression levels of mRNAs for smooth muscle actin and von Willebrand Factor (vWF) increased from low or undetectable levels in undifferentiated epicardial stem/progenitor cells to readily detectable levels as the cells differentiated into precursor cells (FIG. 1K). In addition, the precursor cells expressed the mRNAs of upstream transcription factors such as GATA4, Mef2c, and Myocardin (FIG. 1L).

An alternative method was also developed (method#2) by direct culture of human epicardium dissected from the surface of right atrial appendages, which produced proliferating epicardial progenitor-like cells like those obtained using the method above (method#1).

The epicardial progenitor cells were maintained as epithelial cultures in stem/progenitor cell medium or were induced to undergo epithelial to mesenchymal transformation into mixtures of transit-amplifying precursor cells following adherence to culture plastic. After plating onto charged or coated cell ware in medium containing 10% fetal calf serum (FCS), the majority of the atrial stem/progenitor cells underwent epithelial to mesenchymal transformation into mesodermal progenitors and precursor cells as they expanded in the high serum medium. Some of the precursor cells expressed contractile proteins characteristic of myocytes, while others expressed markers of smooth muscle cells or endothelial cells (FIGS. 2A-2M). The gap junction proteins Cx40 and Cx43 were expressed by the atrial precursor cells, as well as the calcium handling protein Calsequestrin and the SERCA2a ATPase (FIGS. 2E-2H).

Figure 3B:
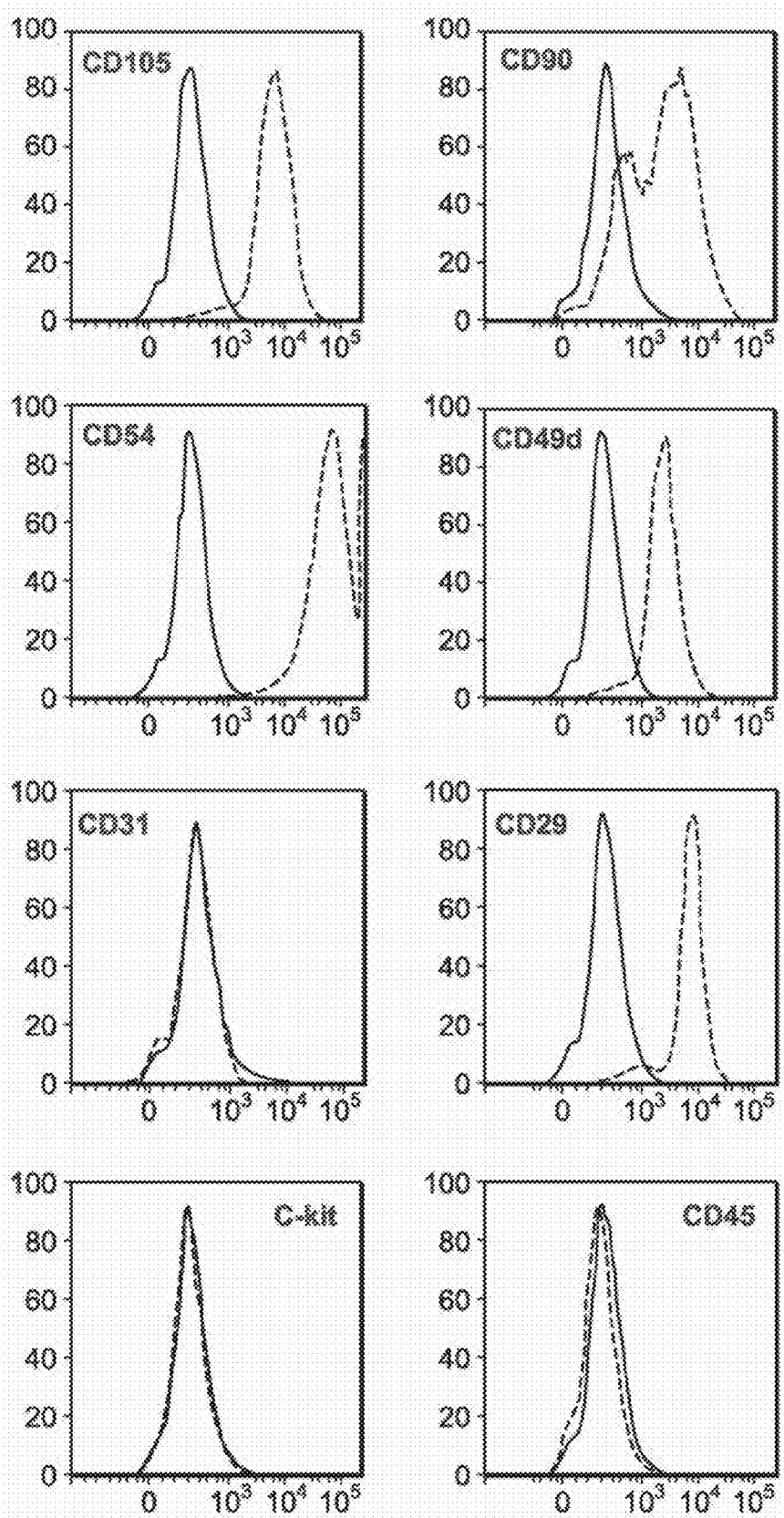

Cell surface phenotyping demonstrated that multiple cell surface antigens typical of bone marrow MSCs such as CD105, CD90, CD73, CD54, CD49d, CD44, and CD29 were expressed by the EDPCs (FIGS. 3A and 3B). However, the precursor cells were negative for endothelial and hematopoietic cell surface markers such as CD31, CD34, CD45, and c-kit, and also the vascular pericyte marker NG2. Many of the precursor cells expressed cell surface antigens typical of mesenchymal stem cells (MSCs), such as CD105, CD90, CD73, CD44, CD29 and Stro-1 (FIG. 3A). Cell surface phenotyping showed that EDPCs generated by methods #1 and #2 expressed identical antigen profiles (FIGS. 3A and 3B).

In an attempt to replace cardiac cells after myocardial infarction, epicardial precursor cells cultured for 2 passages were administered to 3 different strains of immunodeficient mice (NOD/SCID, NOD/SCID/beta 2 m$^{-/-}$, NOD/SCID/IL2rγ$^{-/-}$) by either intramuscular injection into border zone areas or by intra-arterial (left ventricle lumen) administration 1 day after myocardial infarction. The intramuscular cell injections were associated with a persistent but low level of human cell engraftment in the left ventricle (LV) wall 1 week after injection. The intra-arterial infusion of cells after myocardial infarction (MI) led to micro vascular emboli and sudden cardiac death.

Example 2: Conditioned Media Produced from Epicardial Progenitor Cells Preserved Cardiac Function after Myocardial Infarction In cardiac development epicardial cells provide supportive and multifaceted roles. To determine whether agents present in conditioned media secreted by expanded epicardial precursor cells could provide cardioprotection or promote cardiac regeneration after myocardial infarction, a mouse model of myocardial infarction (MI) was used. Due to the human origin of the epicardial progenitor cells, immunodeficient (NOD/SCID) mice were used for treatment with CdM.

To prepare conditioned media from human atrial progenitor cells, atrial progenitor cells cultured for 3 passages were grown in Claycomb expansion medium on 150 cm$^2$ dishes (Nunc). When the cells reached 70-90% confluence, the plates were washed twice with PBS and serum-free alpha minimal essential media (MEM) was placed on the cells (20 mls per plate). After 48 hours of incubation, the conditioned media was collected, filtered (0.2 µm PES membrane, Nalgene MF75, Rochester, N.Y.), and concentrated 30-fold with a commercially available diafiltration system (Labscale™ TFF diafiltration system) using filters with a 5 kD cut-off (Millipore, Bedford, Mass.). Medium components above 5 kD were concentrated (base medium components and salts remained at 1×). One ml vials of conditioned media were frozen and stored at −80° C.

Groups of immunodeficient (NOD-SCID) and immunocompetent (C57 Bl6/J) mice underwent coronary ligation surgery during which the ligature remained in place for 4 hours. Following recovery of the animal after initial suture placement, the mouse was again anesthetized, intubated, and surgically opened at 4 hours post-ligation. Once the intact suture and area of blanching were confirmed and reperfusion was accomplished, Human EPI CdM (30×, 200 µl) warmed to 37° C. was delivered to the entire cardiovascular arterial tree by injecting the solution into the lumen of the left ventricle (LV). This method was designed to deliver a maximum amount of conditioned media to the injured myocardium by employing the naturally existing arterial network of the heart, which is supplied by the immediate portion of the aorta. Using a 30.5 gauge needle inserted below the great cardiac vein (LV apex) at an angle 45° to the myocardium, 200 µl of 30× conditioned media warmed to 37° C. was slowly injected over a period of 1 minute. Control animals received Alpha Minimum Essential Medium (vehicle control, 200 µl) in the same manner. All animals were randomized to treatment at the end of the first surgery (after ligation) and prior to revascularization. Following treatment with either conditioned media or vehicle, the needle was removed and the intercostals were rejoined using 6.0 chromic gut suture (Ethicon, Johnson and Johnson, Inc., Livingston, UK). The lungs reinflated, and the overlying dermis was rejoined with 6.0 nylon suture. Sham mice underwent all procedures except that the suture was passed under the left anterior descending coronary artery (LAD) and not tied. All mice were then recovered to an ambulatory state and transferred to the vivarium for the remaining duration of the experiment.

Figure 4A:
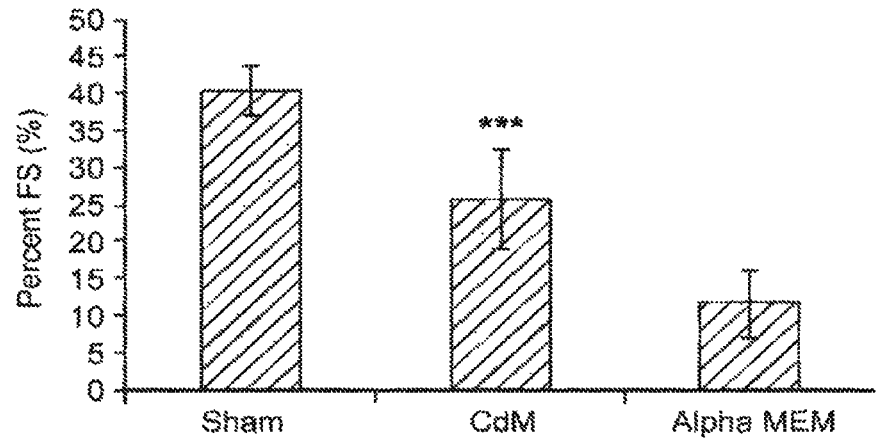
FIGS. 4A-4C are graphs showing the results of intra-arterial administration of concentrated conditioned medium (CdM) from human atrial progenitor cells on cardiac function in immunodeficient mice 1 week after myocardial infarction (MI) with reperfusion. CdM from human atrial progenitor cells improves cardiac function in immunodeficient mice after myocardial infarction with reperfusion.
Figure 4B:
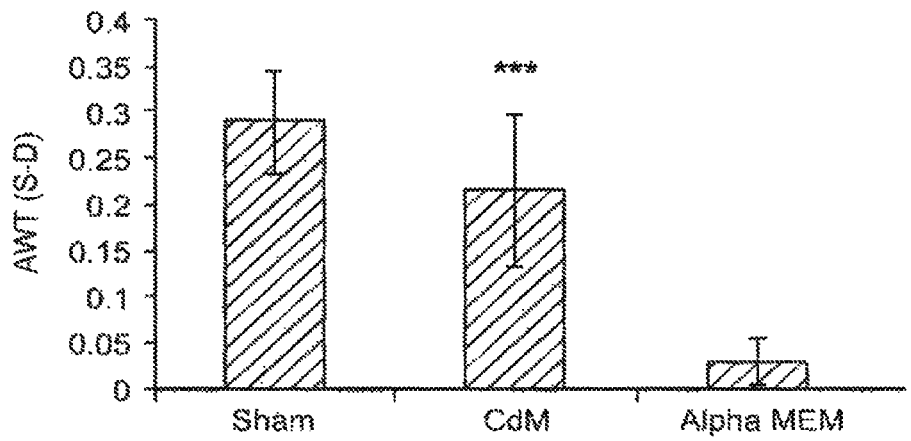
Figure 4C:
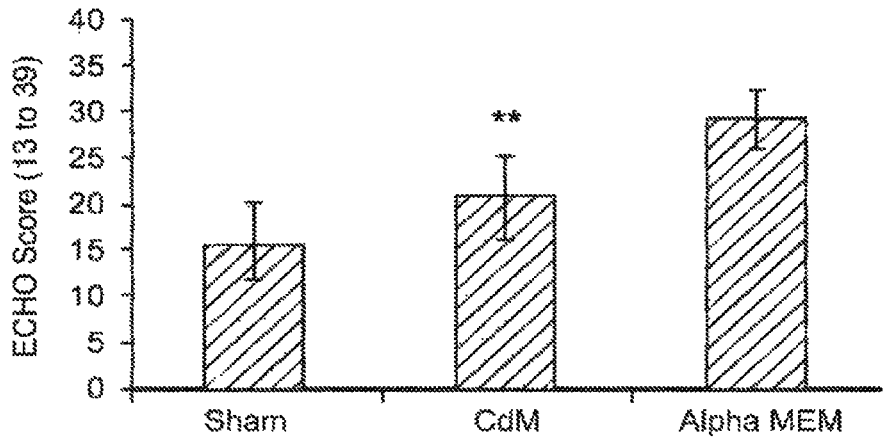

At 1 week after myocardial infarction, dramatic improvements in cardiac function were observed by echocardiography (ECHO) in conditioned media-treated mice compared with controls that received vehicle infusion. There was a highly significant difference in both the percentage of fractional shortening and anterior wall thickness during systole and diastole for immunodeficient mice treated with conditioned media compared with controls (percent fractional shortening (FS), p≤0.001; AWT (S-D), p≤0.001; FIGS. 4A-4C). ECHO scores were determined by a blinded observer using a 13 segment model similar to the American Society of Echocardiography's 17 segment model. ECHO scores demonstrated preservation of wall motion in conditioned media-treated mice compared with controls (p≤0.01, FIG. 4C). Conditioned media from human atrial progenitor cells improved cardiac function in immunodeficient mice after myocardial infarction with reperfusion.

Figure 5A:
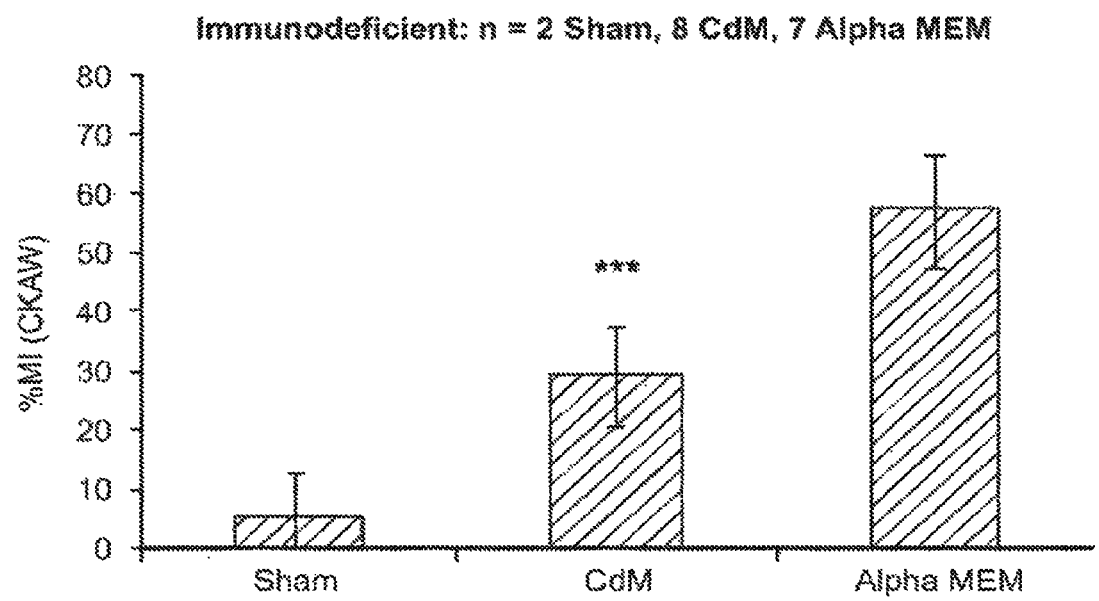
FIGS. 5A and 5B are graphs showing myocardial infarct (MI) size for immunodeficient mice as determined by creatine kinase (CK) activity.
Figure 5B:
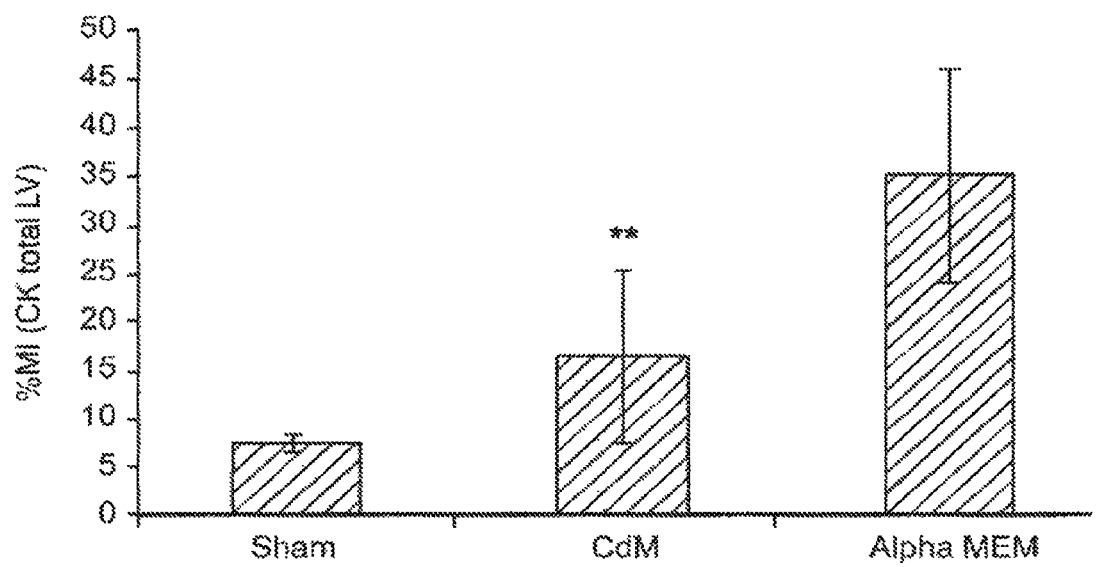

Assessment of surviving ventricular myocardium after myocardial infarction by creatine kinase (CK) activity assays demonstrated a profound rescue of cardiac tissue and a highly significant decrease in the percentage of myocardial infarction in the CdM treatment group (FIGS. 5A and 5B). According to an algorithm that correlated the level of creatine kinase activity with the percentage of myocardium with infarction, the conditioned media treatment reduced the myocardial infarction in the left ventricle walls of immunodeficient mice by about 50% (FIGS. 5A and 5B).

Figure 6A:
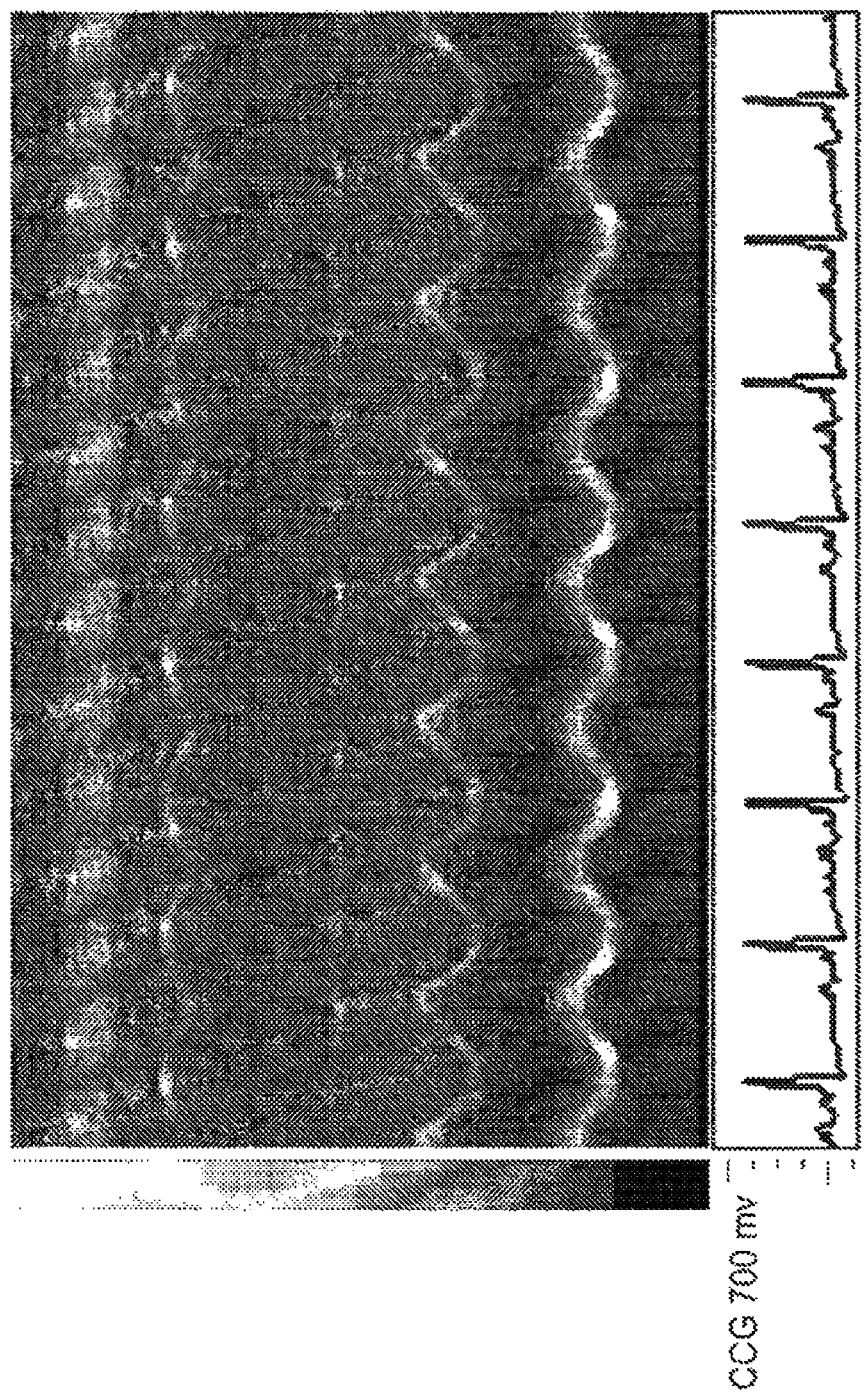
FIGS. 6A-6C are representative M Mode images and electrocardiograms (ECG) of Sham (FIG. 6A), CdM-treated (FIG. 6B), or Alpha MEM-treated (FIG. 6C) immunocompetent mice 1 week after myocardial infarction (MI).
Figure 6B:
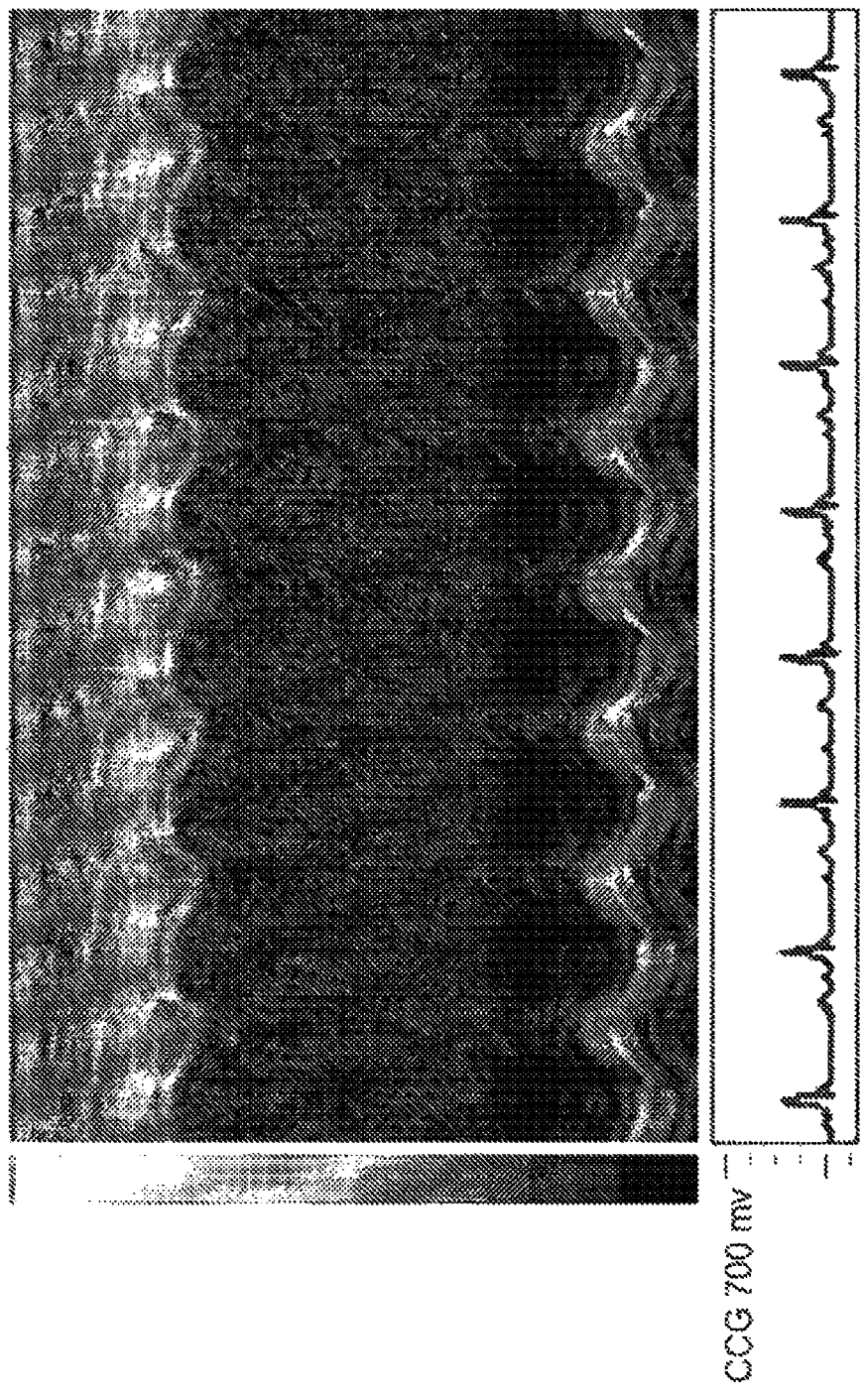
Figure 6C:
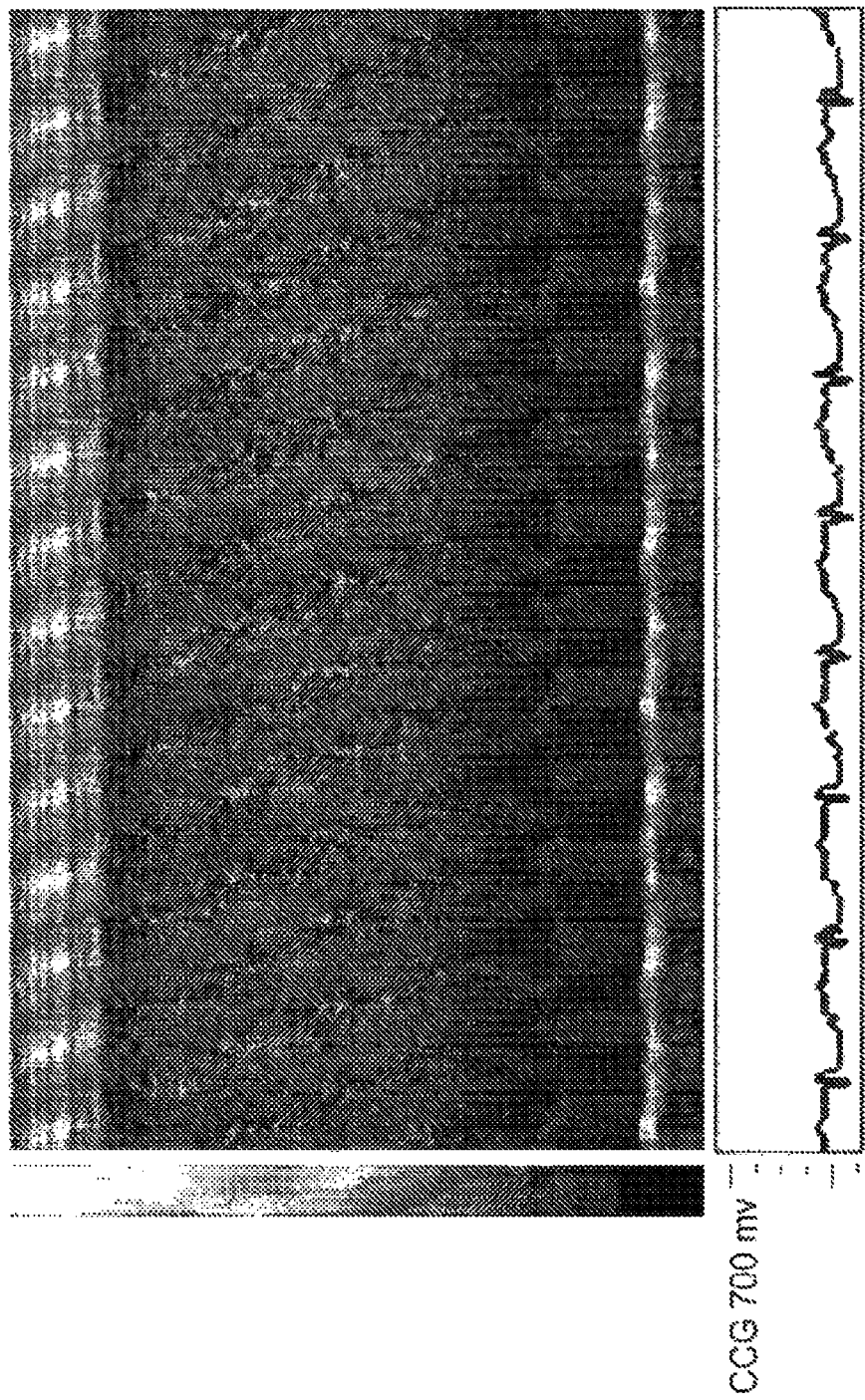
Figure 7A:
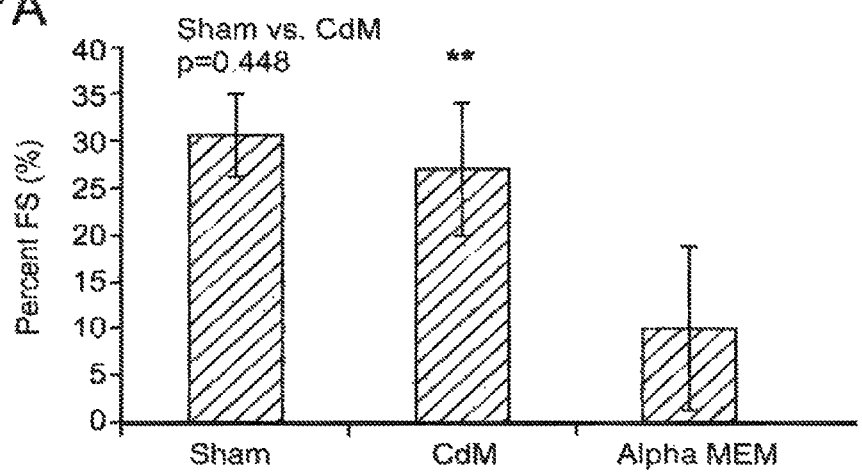
FIGS. 7A-7C are graphs showing the results of intra-arterial administration of concentrated conditioned medium (CdM) from human atrial progenitor cells on cardiac function in immunodeficient mice 1 week after myocardial infarction (MI) with reperfusion. CdM from human atrial progenitor cells improves cardiac function in immunocompetent mice after myocardial infarction with reperfusion.
Figure 7B:
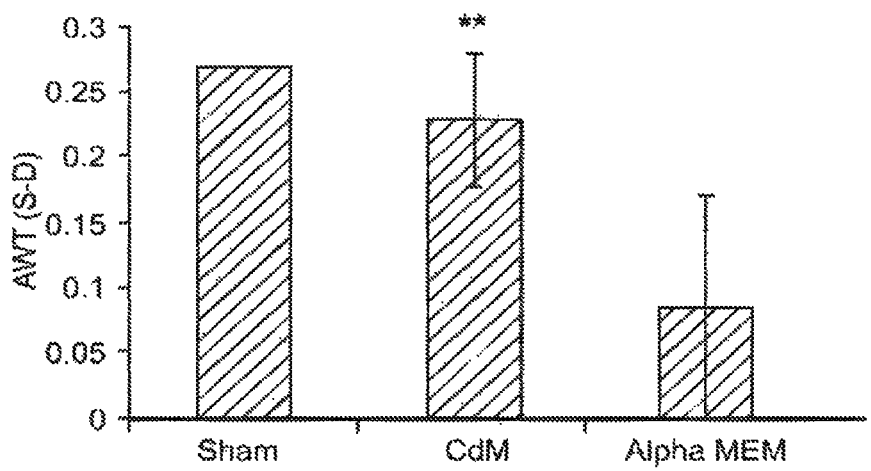
Figure 7C:
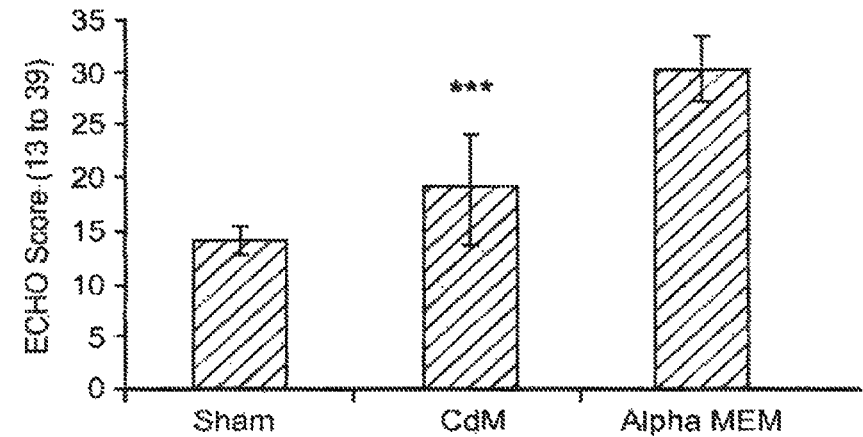
Figure 8A:
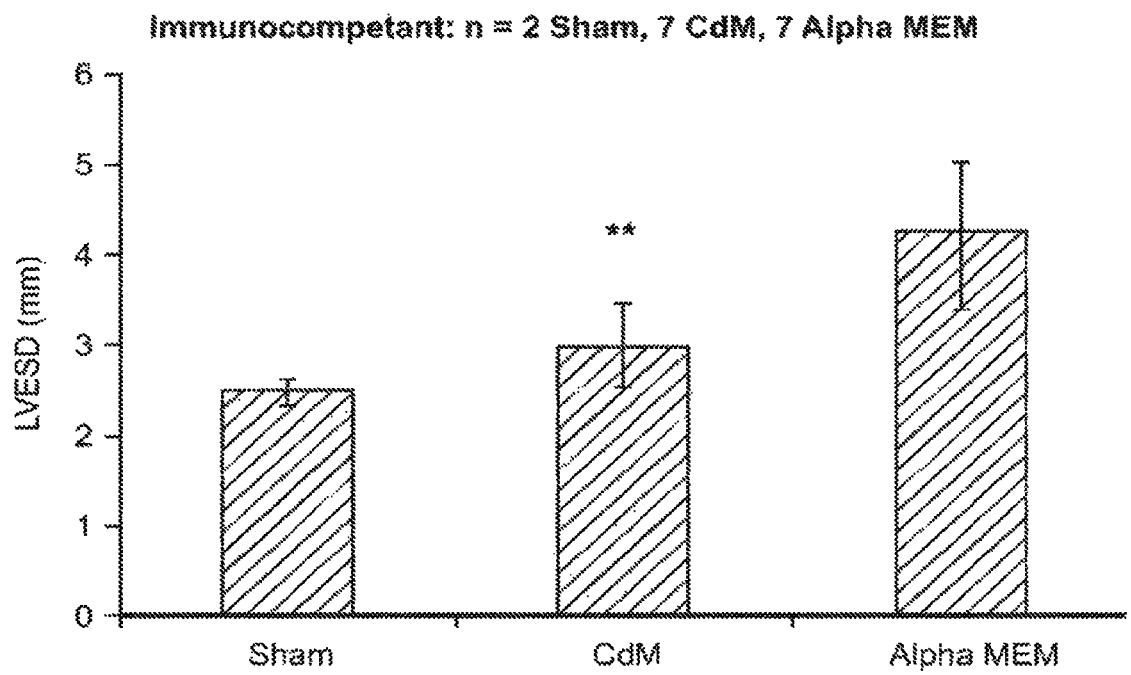
FIGS. 8A and 8B are graphs showing end left ventricular diameter during systole (LVESD) and end left ventricular diameter during diastole (LVEDD) in immunocompetent mice. Improvement in left ventricular dimensions during systole and diastole in CdM-treated immunocompetent mice.
Figure 8B:
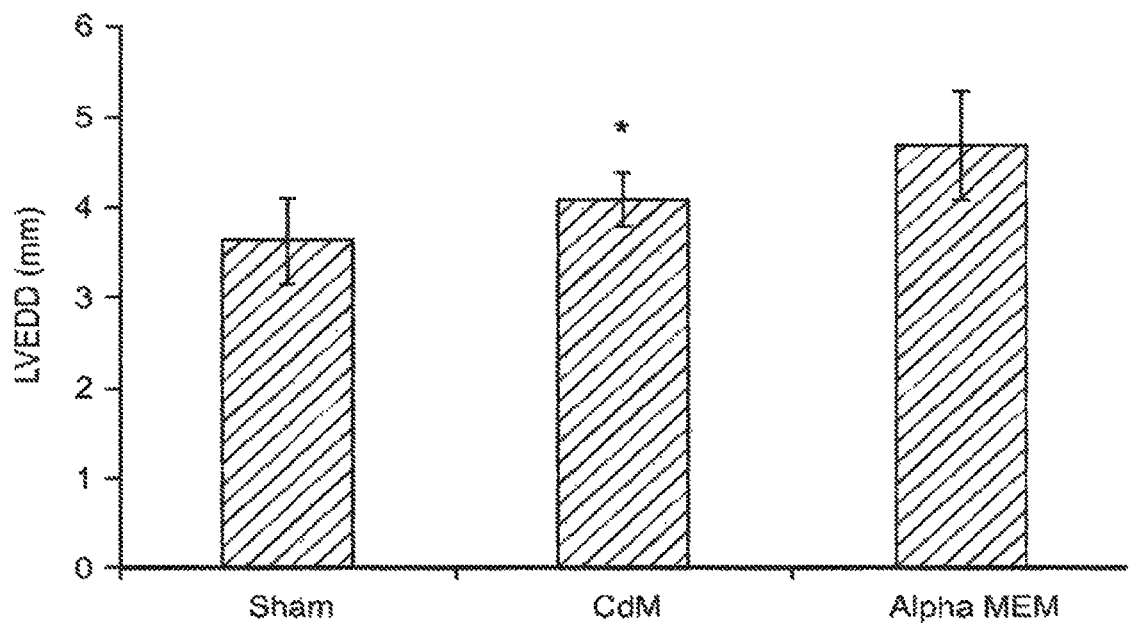
Figure 9:
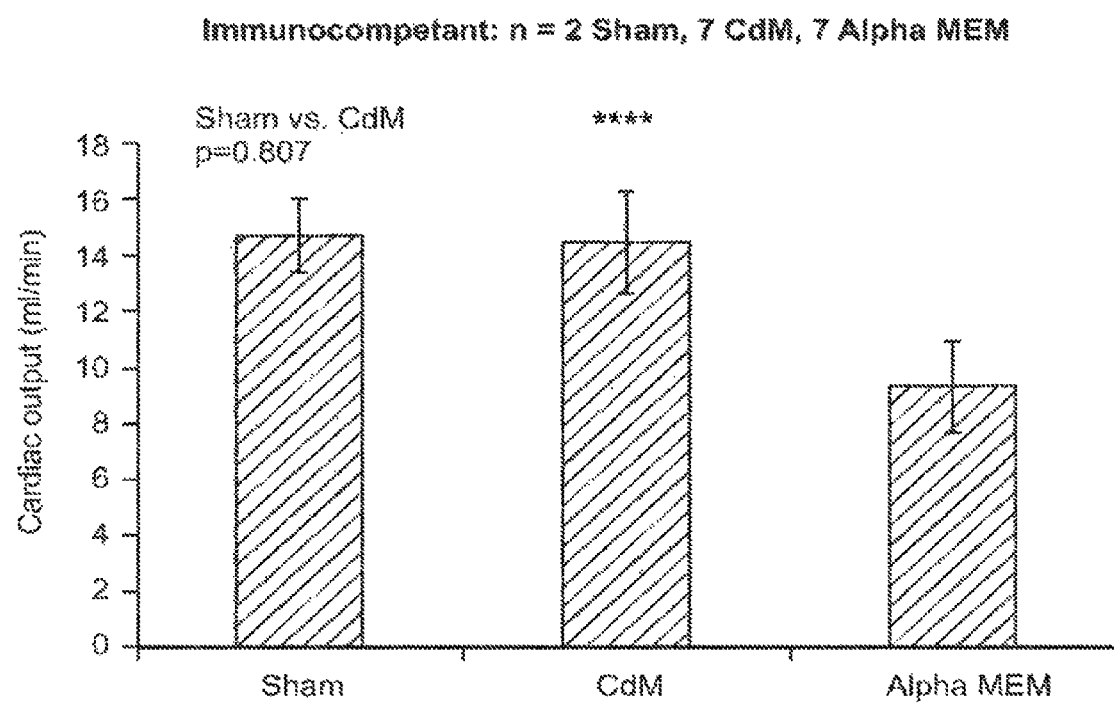
FIG. 9 is a graph showing cardiac output in immunocompetent mice. CdM treatment significantly improves cardiac output after MI in immunocompetent mice compared to treatment with vehicle alone (alpha Minimum Essential Medium; alpha MEM) (**** $p \leq 0.0001$). Cardiac output was calculated from pulmonary arterial Doppler. Sham operated mice underwent all procedures except that the suture was passed under the LAD and not tied; CdM or alpha MEM (vehicle control) was administered intra-arterially at the time of reperfusion after 4 hours of ischemia (Sham, n=2; CdM, n=7; Alpha MEM, n=7).
Figure 10A:
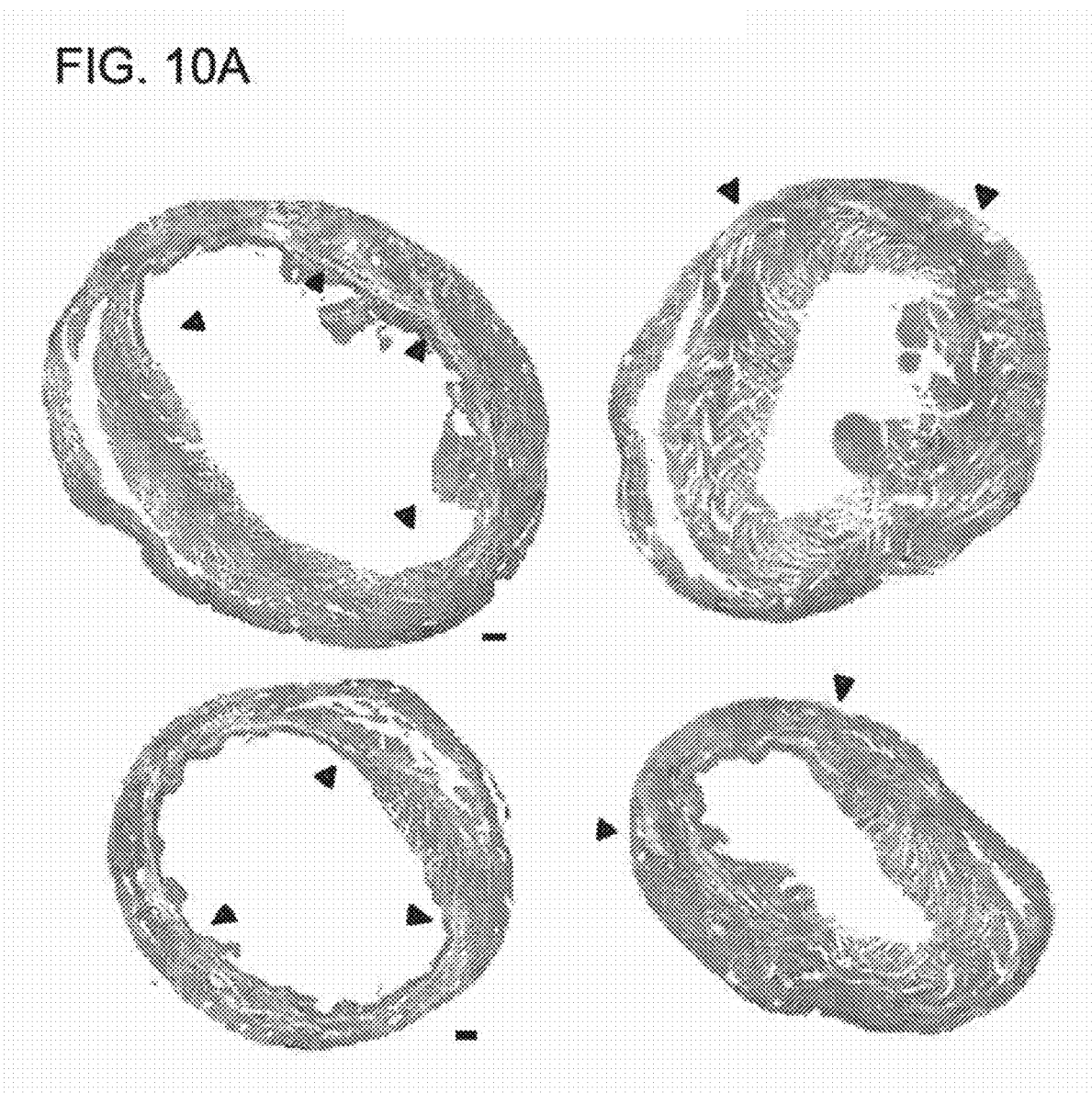
FIGS. 10A-10G show that EPI CdM treatment reduced infarct size at 1 wk after MI and reperfusion and improved cardiac function of immunocomeptent (C57bl6/J) mice at 1 month after MI and reperfusion.
Figure 10B:
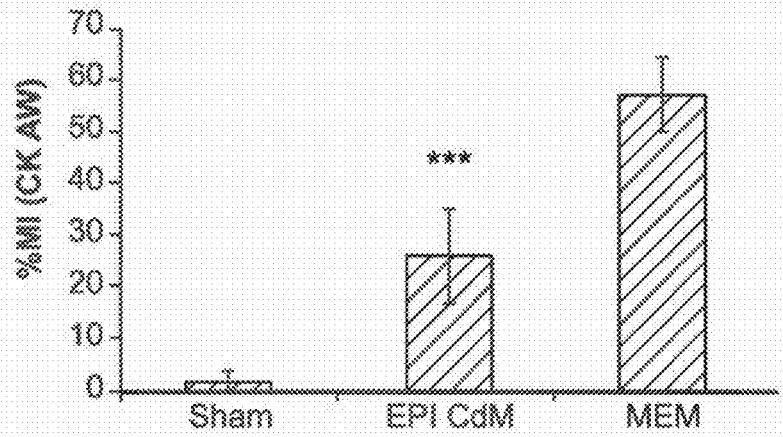
Figure 10C:
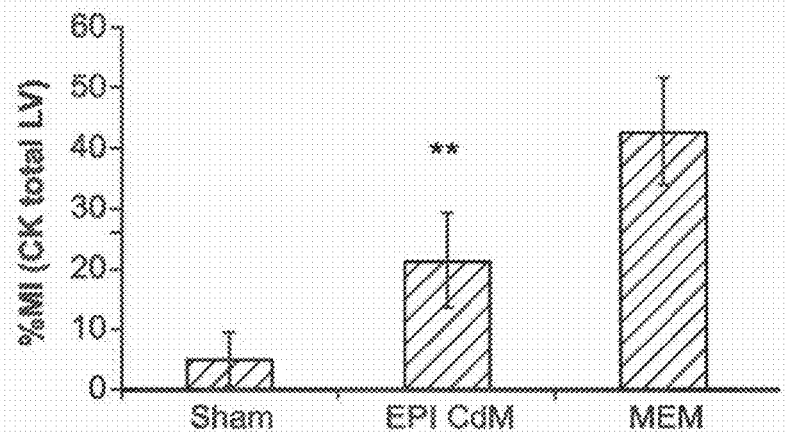
Figure 10D:
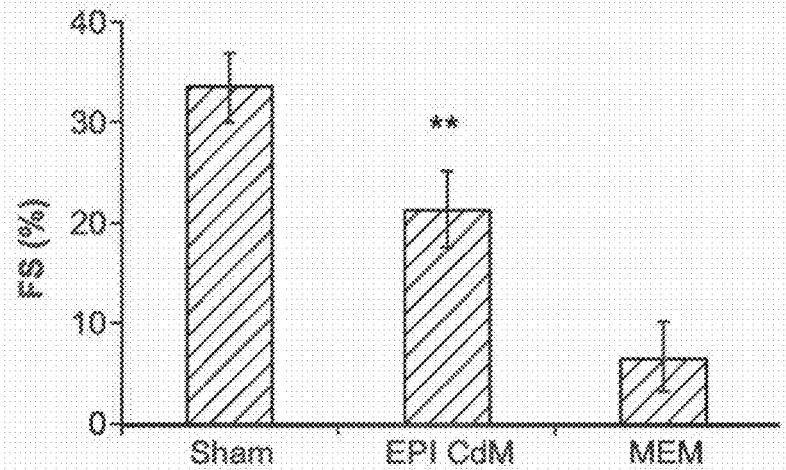
Figure 10E:
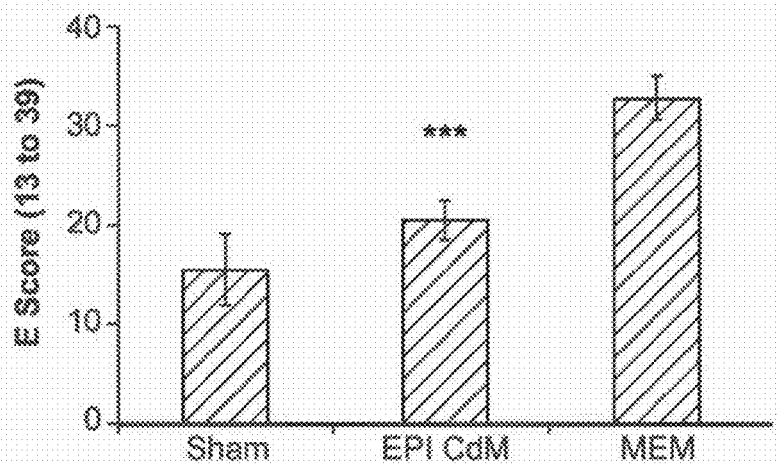
Figure 10F:
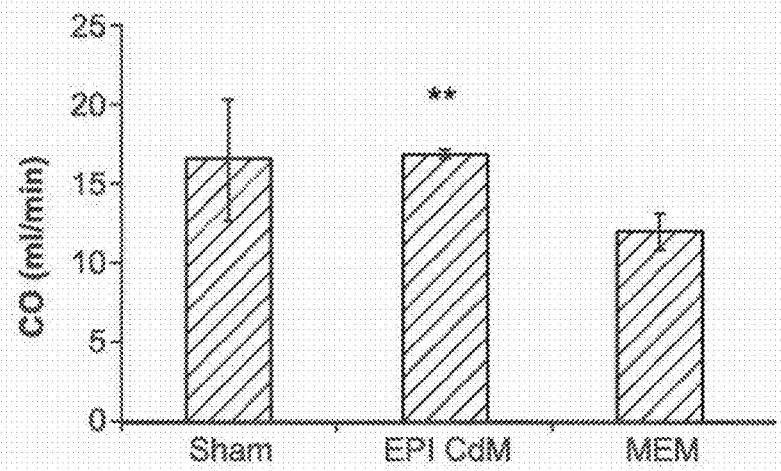
Figure 10G:
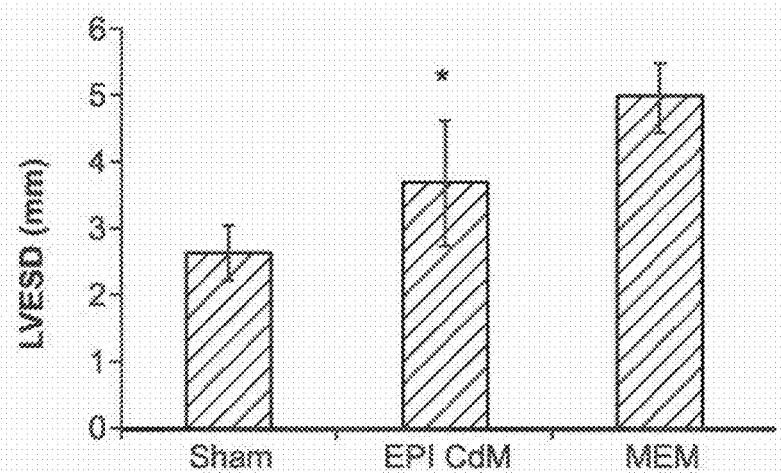

The conditioned media from the human epicardial progenitor cells also rescued left ventricular myocardium in immunocompetent mice. Representative M Mode images and electrocardiograms (ECG) for sham-operated, conditioned media-treated, and alpha MEM-treated (control) mice are shown in FIGS. 6A-6C. There was a significant increase in the percentage of fractional shortening in conditioned media-treated immunocompetent mice compared with controls, in anterior wall thickness between systole and diastole, and in wall motion as determined again by ECHO scoring (percent FS, p≤0.01; AWT (S-D), p≤0.01; ECHO score, p≤0.001; FIGS. 7A-7C). The percent FS for sham-operated and CdM-treated mice was not significantly different (p=0.448). There were significant improvements in left ventricular dimensions during both systole and diastole in conditioned media-treated versus control animals (LVESD, p≤0.01, LVEDD, p≤0.05; FIGS. 8A and 8B). For immunocompetent mice with myocardial infarction, there was a highly significant increase in cardiac output as measured from the pulmonary artery in the conditioned media-treated group compared with controls (p≤0.0001, FIG. 9). In fact, cardiac output after myocardial infarction for conditioned media-treated mice did not differ from that of sham-operated mice (p=0.807). Similar to the case in NODSCID mice, the EPI CdM treatment reduced the extent of infarction in C57bl6/J mice by over 50% (FIGS. 10A-10C). Gomori trichrome staining of serial sections from control and EPI CdM-treated mice at 7 days after MI demonstrated that EPI CdM treatment decreased the area of tissue injury (FIG. 10A). By creatine kinase assays the epicardial progenitor cell conditioned media reduced the percentage of left ventricle with myocardial infarction in immunocompetent mice by over 50% (FIGS. 10B and 10C). To determine whether EPI CdM treatment could provide long-term benefit, groups of C57bl6/J mice were observed for 1 month after MI, reperfusion and treatment to evaluate their cardiac function. Significant differences in cardiac function between EPI CdM-treated mice and controls were still evident at 1 month after treatment (FIGS. 10D-10F).

Figure 12A:
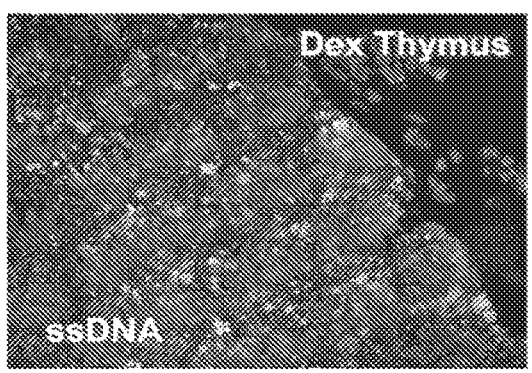
FIGS. 12A-12G show that EPI CdM treatment significantly reduced cardiac necrosis at 24 hours after myocardial infarction with reperfusion.
Figure 12B:
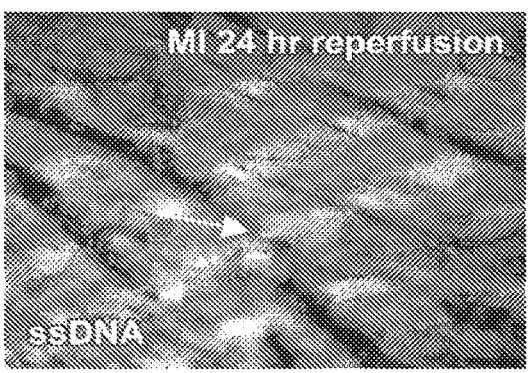
Figure 12C:
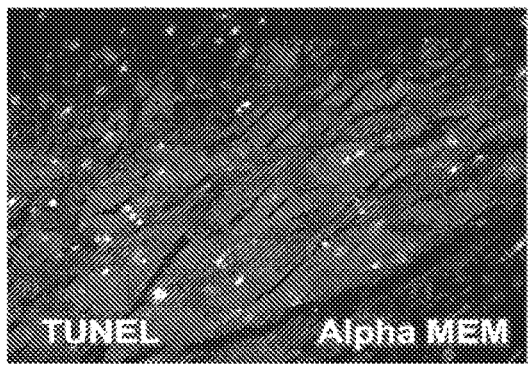
Figure 12D:
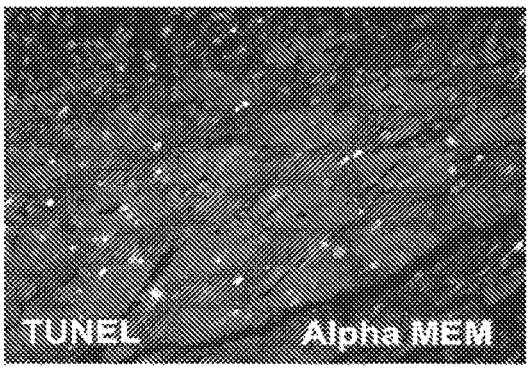
Figure 12E:
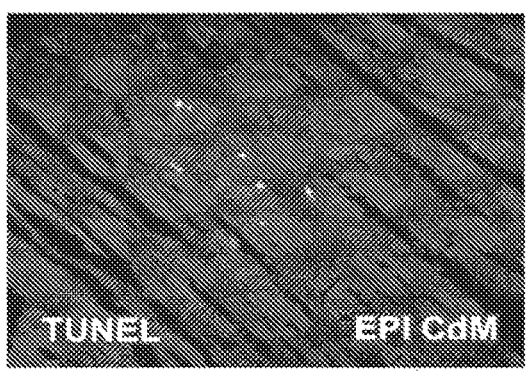
Figure 12F:
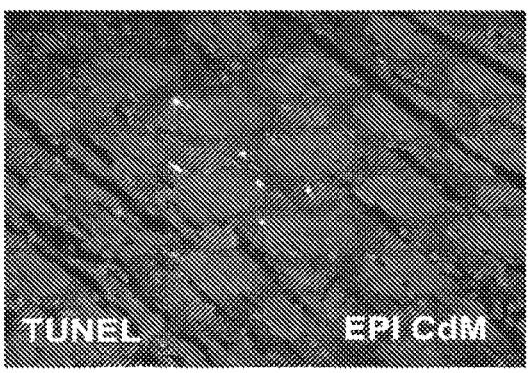
Figure 12G:
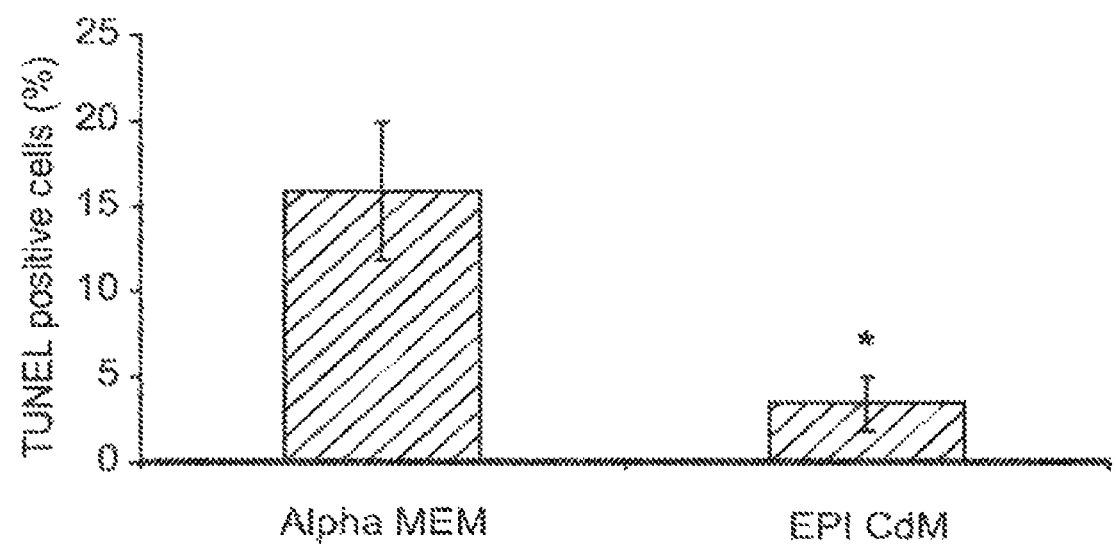

Example 3: Conditioned Media from the Human Epicardial Progenitor Cells Contains Growth Factors that Reduce Cardiac Necrosis Following Myocardial Infarction To examine the timing and nature of cardioprotection provided by conditioned media from the human epicardial progenitor cells (EPI CdM), groups of immunocompetent mice were subjected to the 4 hour ischemia/reperfusion myocardial infarction (MI) model, treated with EPI CdM at the time of reperfusion, and euthanized after 24 hours to determine the numbers of cardiac cells undergoing apoptosis or necrosis. Similar to the results reported above, immunohistochemical assays specific for apoptotic cells (single-stranded DNA, ssDNA) minimal numbers of apoptotic cells were observed in either control hearts or those treated with EPI CdM at 24 hours after ischemia and reperfusion (FIGS. 12A-12G). Because one apoptotic cell was detected (ss-DNA-positive) or less on multiple heart sections from control and EPI CdM-treated animals, apoptosis was not quantified. In contrast, TUNEL staining of control hearts that received alpha MEM infusion indicated widespread cardiac necrosis at 24 hours after MI (FIGS. 12C and D). EPI CdM treatment significantly reduced the numbers of TUNEL-positive cells within the infarct zone at 24 hrs after MI (P=0.023, FIG. 12E-G).

Figure 13A:
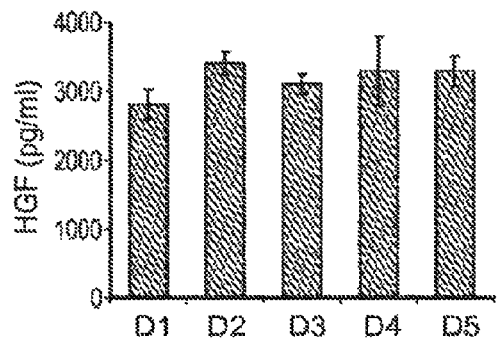
FIGS. 13A-13L are graphs showing that HGF is a cardioprotective and vasoprotective component of EPI CdM.
Figure 14A:
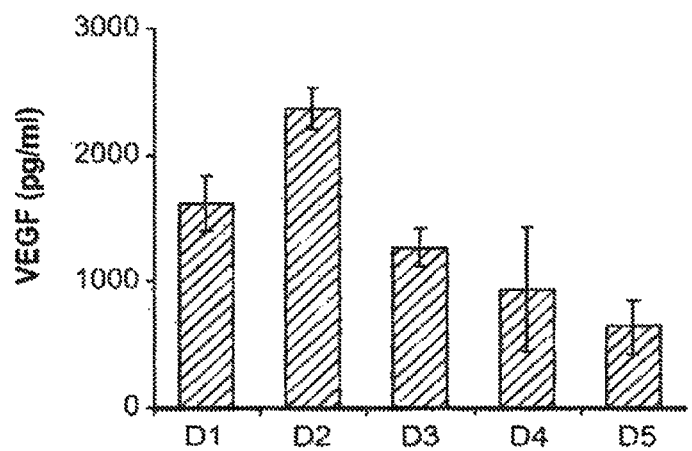
FIGS. 14A-14C provide graphs showing quantification of secreted proteins present in 1× EPI CdM: VEGF, IGF-1, and SDF-1, respectively. Data are shown for 5 different human donors. All ELISA data are in triplicate.
Figure 14B:
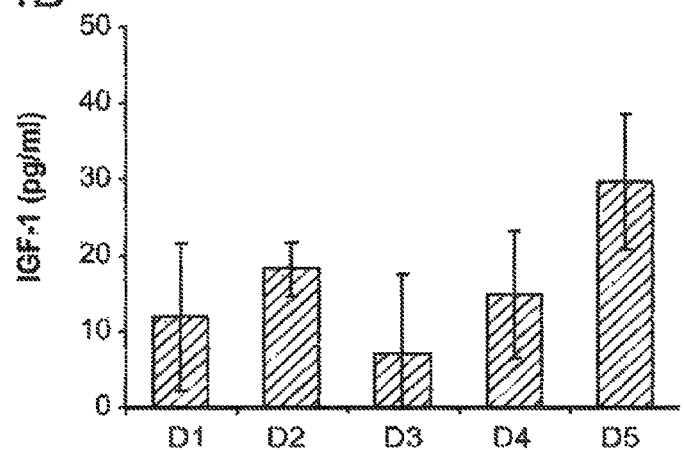
Figure 14C:
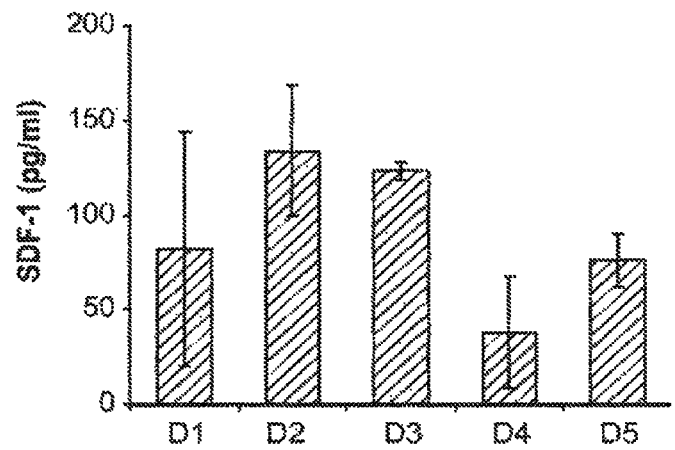

To characterize the cardioprotective factors contained in EPI CdM, ELISAs for Hepatocyte Growth Factor (HGF), Vascular Endothelial Growth Factor (VEGF), Insulin-like Growth Factor (IGF-1), and Stromal-Derived Factor 1 (SDF-1 alpha) were performed on EPI CdM (FIGS. 13A and 14). EPI CdM examined from several different human donors contained relatively high levels of HGF (about 3 ng/ml in 1× EPI CdM, FIG. 13A), variable levels of VEGF (between 500 pg/ml and 2.5 ng/ml, FIG. 14), and low levels of SDF-1 alpha (<150 pg/ml, FIG. 14) and IGF-1 (<30 pg/ml, FIG. 14).

Figure 13B:
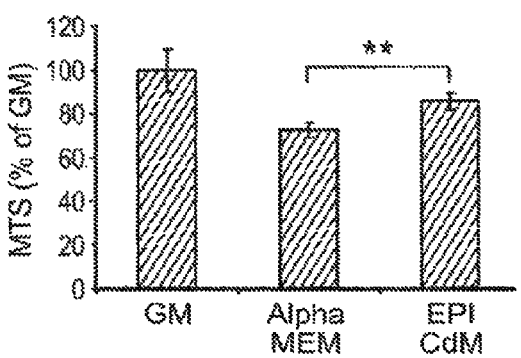
Figure 13C:
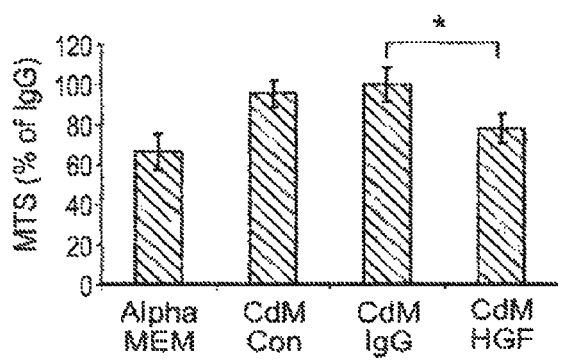
Figure 13D:
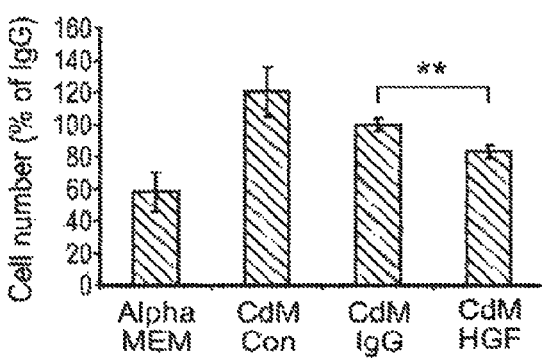
Figure 13E:
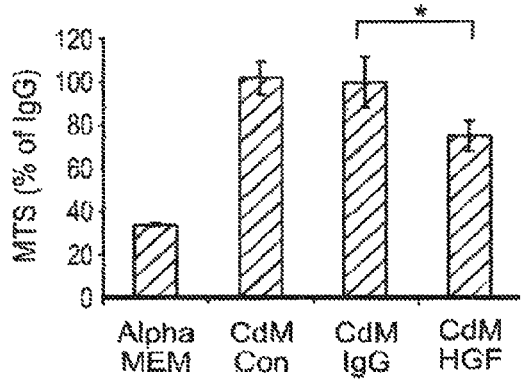
Figure 13F:
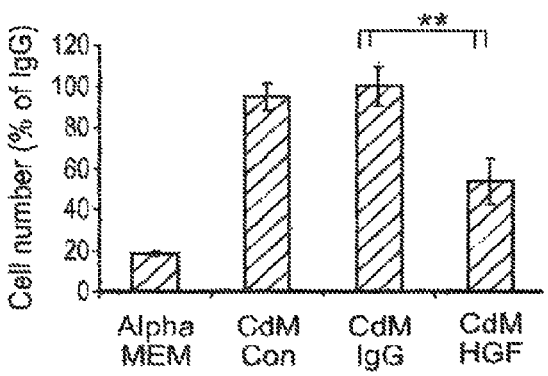
Figure 13G:
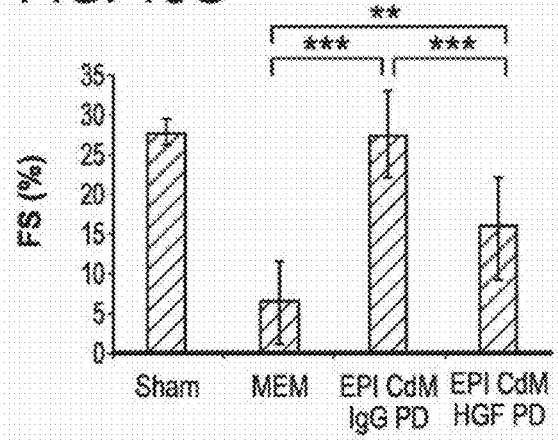
Figure 13H:
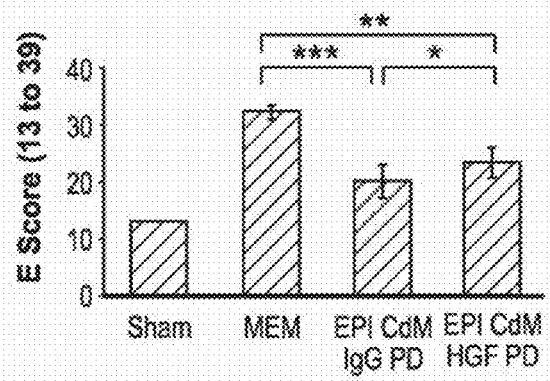
Figure 13I:
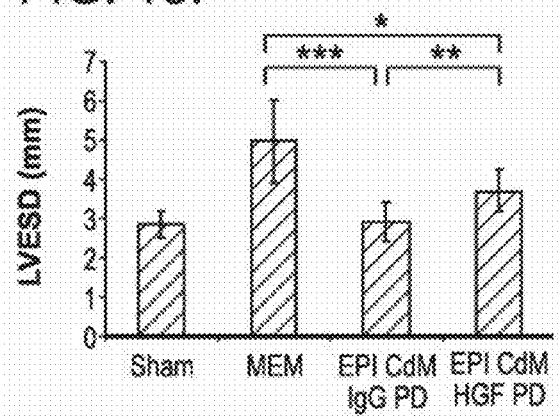

To examine whether EPI CdM from donors of varying ages would provide cardioprotection, cell protection assays were performed under conditions of simulated ischemia (low glucose medium, 1% oxygen, for 24 or 48 hrs). Compared with incubation in alpha MEM (vehicle), unconcentrated EPI CdMs generated from precursor cells of donors from 52 to 80 years of age all significantly protected primary human cardiac endothelial cells from simulated ischemic injury for 24 hours (FIG. 13B). EPI CdMs concentrated to 10× provided a greater level of cell protection than did unconcentrated 1× EPI CdMs and significantly protected both human aortic and coronary artery endothelial cells for 48 hours (FIGS. 13C-13F). Neutralizing antibodies to human HGF, but not VEGF, significantly reduced EPI CdM-mediated protection of primary human aortic and coronary artery endothelial cells (FIG. 13C-13F). Notably, advanced patient age did not diminish the ability of EPI CdM to provide vaso- or cardioprotection. EPI CdM generated from EDPCs of an 80 yr old patient protected cardiac endothelial cells as well as EPI CdM from a 50 yr old patient and preserved myocardial tissue in multiple mouse strains after MI. Relevant to clinical application, the human EPI CdM we used was produced, sterile filtered, and stored frozen, consistent with a long shelf life.

Figure 13J:
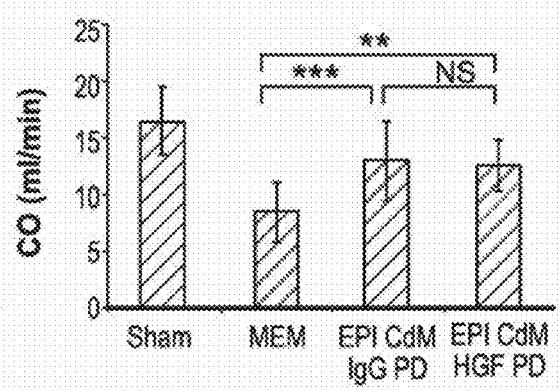
Figure 13K:
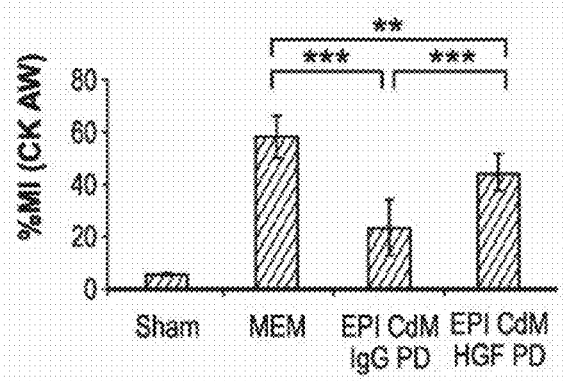
Figure 13L:
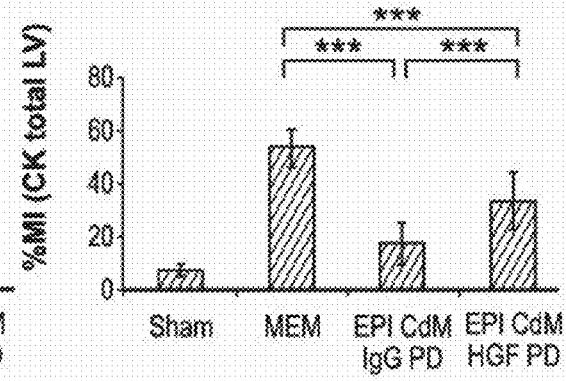
Figure 15A:
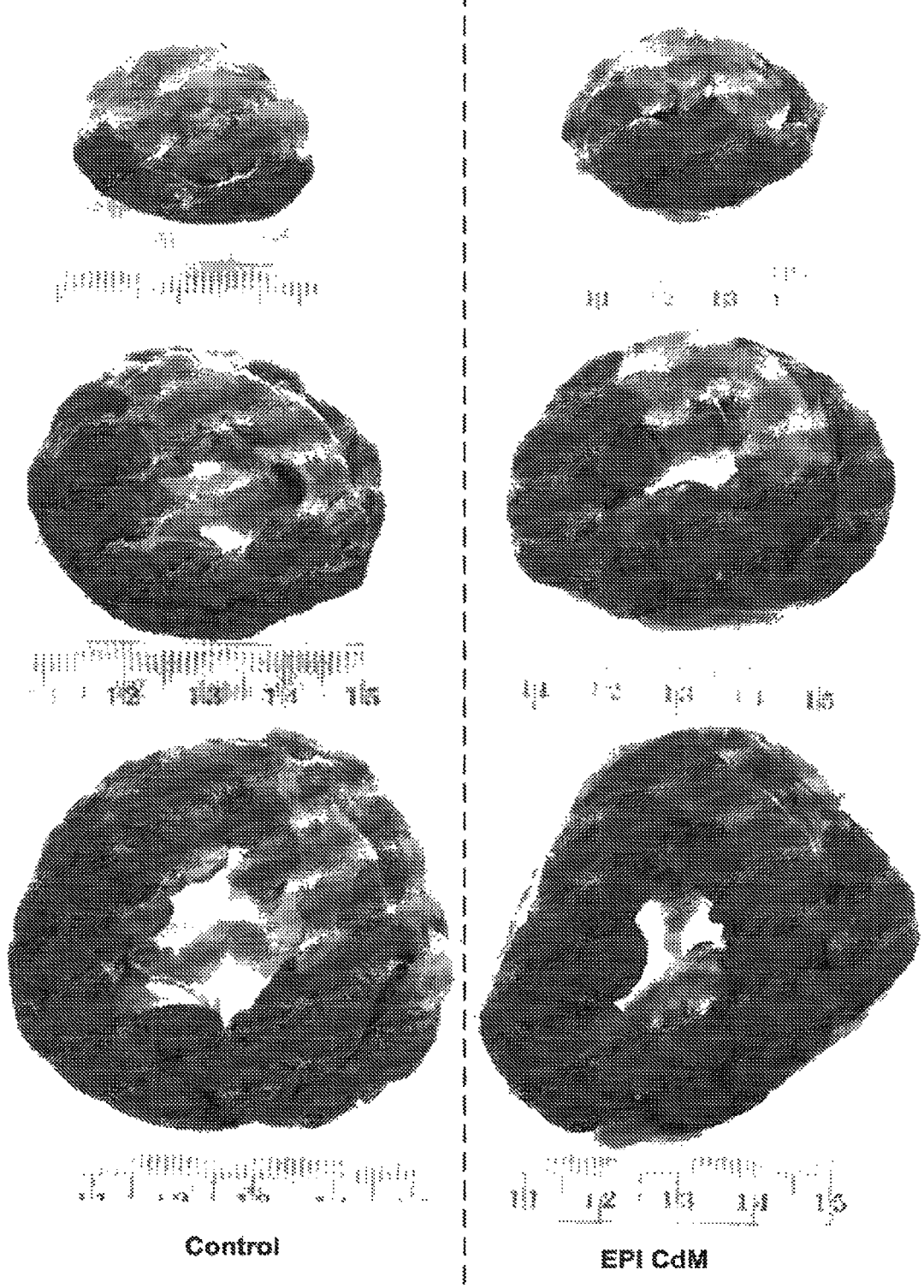
FIG. 15 is a graph showing that a pulldown (PD) method depleted growth factors from 30× EPI CdM. HGF PD using biotinylated primary antisera specific to HGF removes all detectable HGF from EPI CdM. HGF ELISA shows that incubation of EPI CdM in biotinylated non-specific IgG from the same host species does not affect HGF concentration compared with original EPI CdM. Samples were incubated in strepavidin conjugated agarose to remove antibody complexes during centrifugation. ELISA data are shown in triplicate.
Figure 15B:
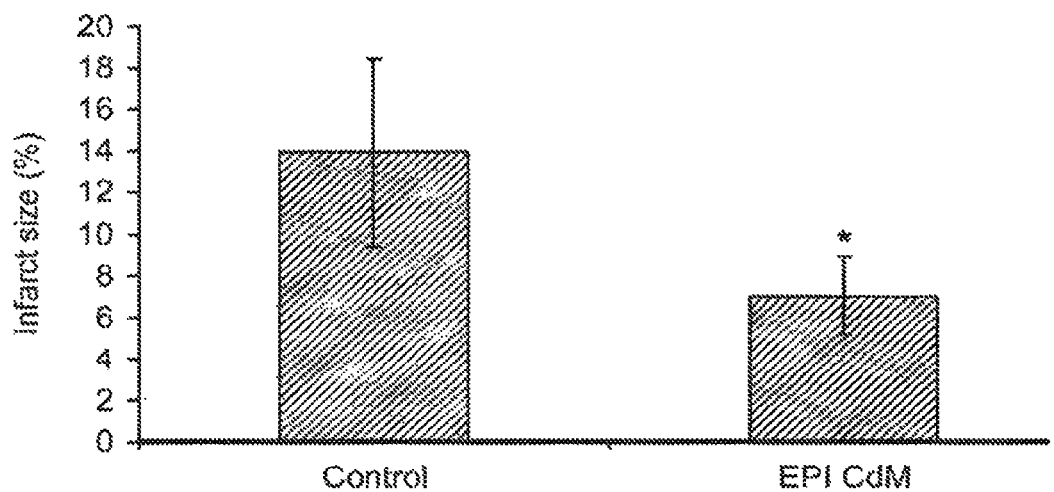
Figure 15C:
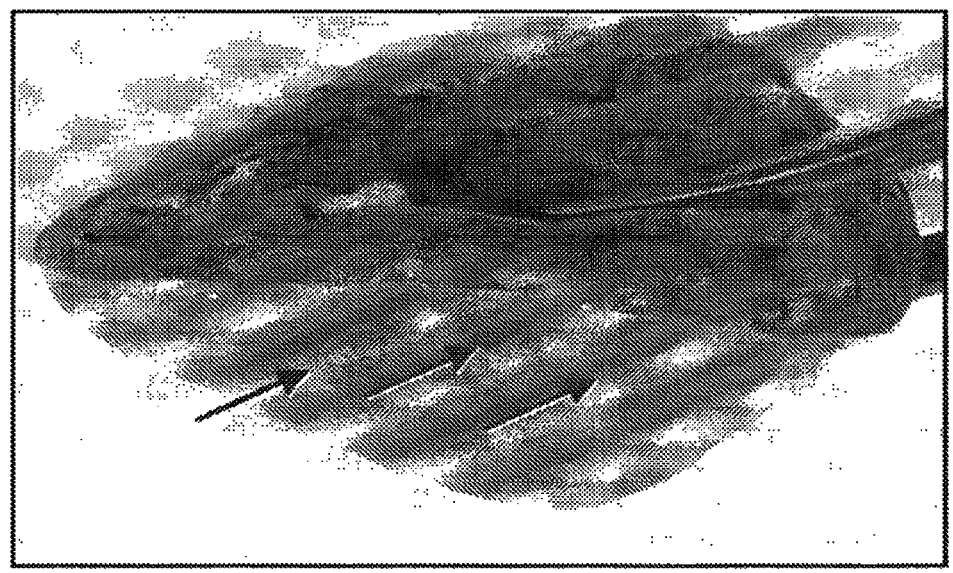

To determine the relative importance of HGF in the cardioprotection conferred by EPI CdM in vivo, pulldowns (PD) were performed with biotinylated antisera specific to HGF or biotinylated non¬ specific IgG (control). By ELISA, incubation in strepavidin-agarose and centrifugation removed 100% of HGF from EPI CdM (FIG. 15). Groups of C57bl6/J mice were subjected to the 4 hr ischemia/reperfusion MI model, and were treated with Alpha MEM, non-specific IgG-PD EPI CdM (IgG-PD), or HGF-PD EPI CdM (HGF-PD). Removal of HGF from EPI CdM significantly reduced its therapeutic effects as determined by several criteria used to assess cardiac function (FIGS. 13G-13I) and the degree of tissue preserved at 1 wk after MI, reperfusion and treatment (FIGS. 13K and 13L). Assay of residual LV CK showed that treatment with HGF-PD resulted in a 51% decrease in the amount of cardiac muscle rescued by IgG-PD treatment. Notably, however, the removal of HGF only partially reduced the beneficial effects of EPI CdM. Treatment with HGF-PD still provided significant improvement in cardiac function compared with Alpha MEM-infused controls (FIGS. 13A-13L). In addition, the cardiac output of mice that received HGF-PD did not differ from that of IgG-PD treated mice (FIG. 13J).

Example 4: EPI CdM Preserves Cardiac Tissue after MI in a Large Animal Model (Swine)

Figure 16A:
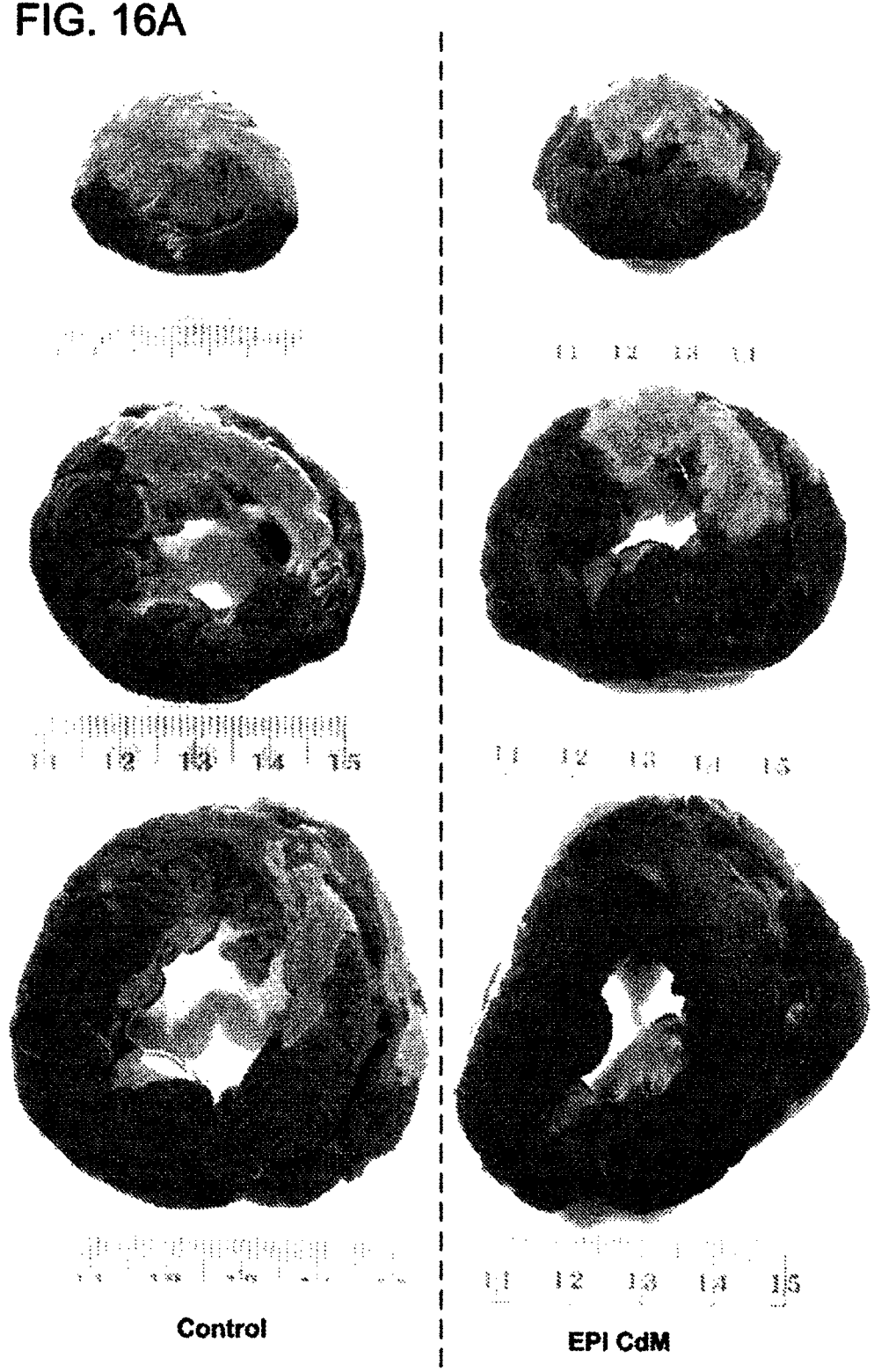
FIGS. 16A-16C show Intra-coronary EPI CdM infusion at reperfusion preserves cardiac tissue in adult swine after MI.
Figure 16B:
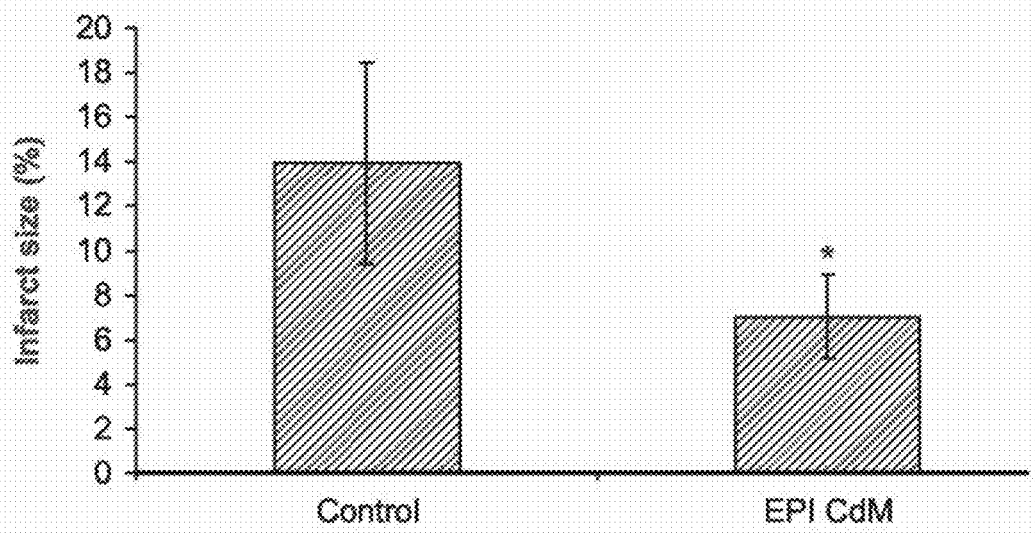
Figure 16C:
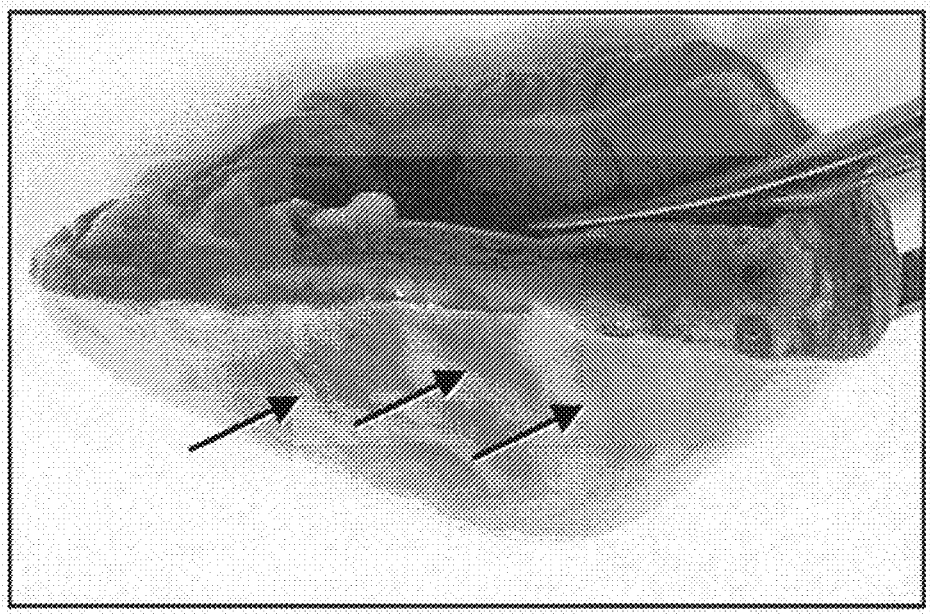

To determine whether human EPI CdM would also preserve cardiac tissue after MI in a large animal model, studies with 10 adult conventional farm swine were carried out (~65 kgs). Under anesthesia and with fluoroscopic guidance, a balloon catheter was advanced and inflated to completely occlude the LAD for 1 hour prior to revascularization. At the time of reperfusion, pigs in the control group received additional contrast dye to confirm re-flow (n=5). Alternatively, pigs in the treatment groups received 16 mls of 20× EPI CdM and contrast (n=3) or 16 mls of 25× EPI CdM and contrast (n=2), by infusing 8 mls of EPI CdM directly into the LCAD at the location of the deflated balloon, and an additional 8 mls into the left main coronary artery from the guide catheter. The EPI CdM was infused over 3-5 minutes. No anti-arrhythmic drugs were used and there were no adverse events following any of the treatments. All pigs were euthanized at 24 hours after treatment. The hearts were removed and cut transversely from apex to base (1 cm slices), stained by 2,3,5-Triphenyltetrazolium chloride (TTC), and digitally photographed (FIG. 16A). The weights of right and left ventricular tissue from each 1 cm slice were recorded. The areas of viable and scarred cardiac tissue were quantified with Scion Image software, averaged between slices, and multiplied by the tissue weights to estimate infarct size. As the effects of 20× and 25× EPI CdM on infarct size were similar (both P=0.03 compared with control infarct size), the treatment data was grouped together (FIGS. 16A-16C). The combined data indicated a 51% reduction in infarct size at 24 hours after MI compared with infarct size in controls that received contrast alone (P=0.024, FIG. 16B). However, by gross inspection hearts treated with 25× EPI CdM appeared better than those treated with 20× EPI CdM, with islands of spared (viable) myocardium at the apex (FIG. 16C).

Example 5: EPI CdM Provides Vasoprotection and Prevents Vascular Rhexis after MI and Reperfusion To determine whether EPI CdM treatment was vasoprotective in the context of MI and reperfusion, assays of vascular integrity were performed at 24 hrs after MI, reperfusion and treatment. As HGF depletion only partially reduced the benefit of EPI CdM treatment, multiple factors present in EPI CdM could work in concert to preserve vascular integrity after MI and reperfusion. Using the same biotinylated antibody PD strategy to remove multiple growth factors simultaneously, HGF, VEGFA, and SDF-1 alpha were depleted from 30× EPI CdM (3 GF PD). Non-specific IgG-PD control EPI CdM was formulated to match the concentrations of IgG used for specific PD.

To assess microvascular rhexis, FITC-albumin (FITC-Alb) was injected by tail vein 2 hrs before euthanization. Serial sections were cut from each heart from apex to base and used to determine the mural volume containing extravasated FITC-Alb. TUNEL assays performed on the same sections demonstrated that FITC-positive areas of the LV correlated with areas of cellular necrosis (FIGS. 17A-17D and 18; Table 2).

TABLE 2

Correlation of TUNEL positive cells in left ventricle with areas containing FITC-Alb at 24 hr after MI and reperfusion

|  | Outside (%) | Border (%) | Inside (%) |
|---|---|---|---|
| Alpha MEM | | | |
| A | 0 | 0 | 100 |
| B | 0 | 0 | 100 |
| C | 0 | 0 | 100 |
| D | 25 | 0 | 100 |
| IgG-PD | | | |
| A | 16.7 | 40 | 100 |
| B | 0 | 50 | 100 |
| C | 0 | 0 | 100 |
| D | 0 | 0 | 100 |
| E | 0 | 25 | 100 |
| F | 0 | 33.3 | 100 |
| 3 GF PD | | | |
| A | 33.3 | 33.3 | 100 |
| B | 0 | 20 | 100 |
| C | 0 | 0 | 100 |
| D | 0 | 25 | 100 |
| E | 0 | 0 | 100 |

Serial sections spanning the infarct zone were scored for presence or absence of TUNEL positive cells outside the FITC-positive area, in border regions of FITC staining, and inside the FITC-positive area. Border regions were defined by taking photomicrographs that contained 50% of FITC-positive myocytes and 50% FITC-negative myocytes. Data indicate the percentage of sections that contained at least a single TUNEL-positive cell in a particular area for a given animal. For each animal, 4 to 5 sections were scored that spanned the region of infarction.

Figure 17A:
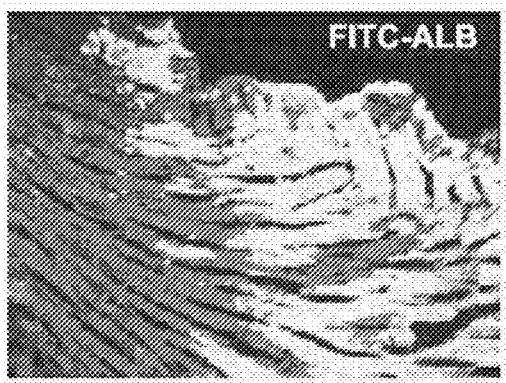
FIGS. 17A-17G show that multiple vasoprotective factors in EPI CdM acted in concert to prevent vascular rhexis after MI and reperfusion
Figure 17B:
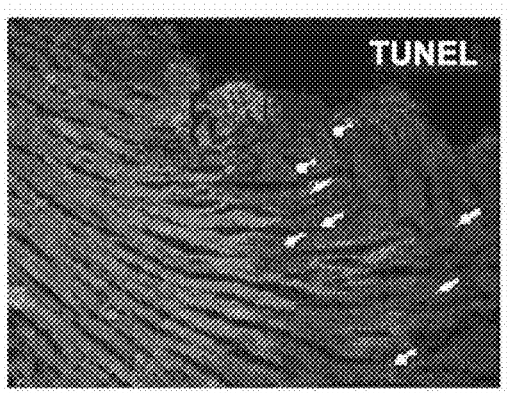
Figure 17C:
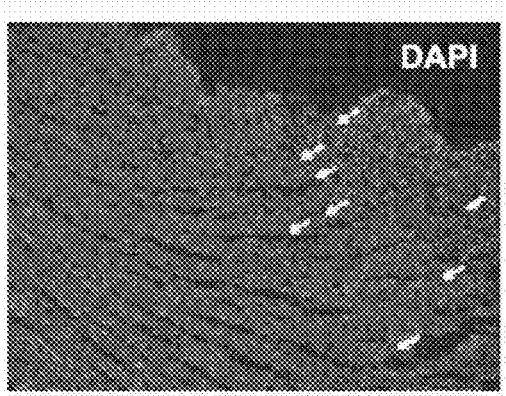
Figure 17D:
Figure 17E:
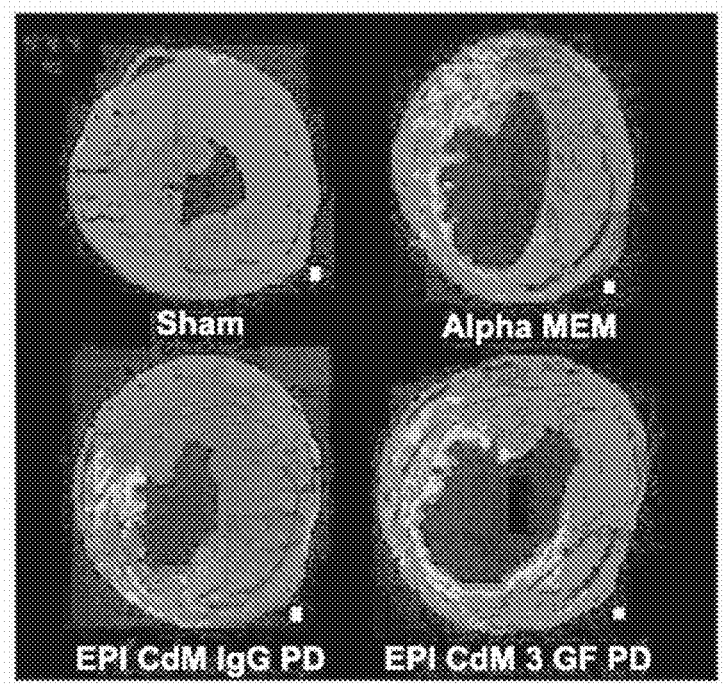
Figure 17F:
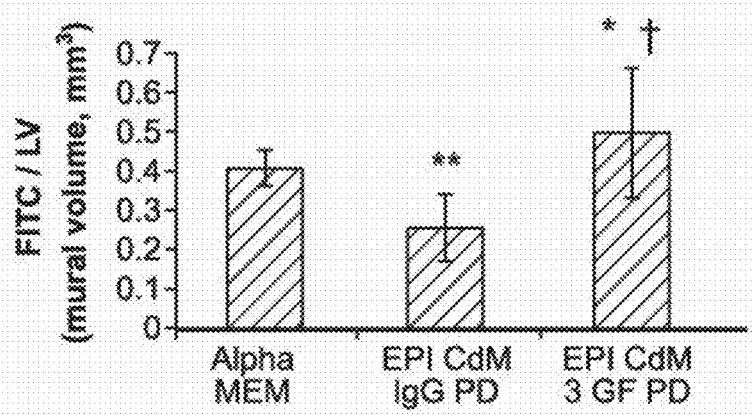
Figure 17G:
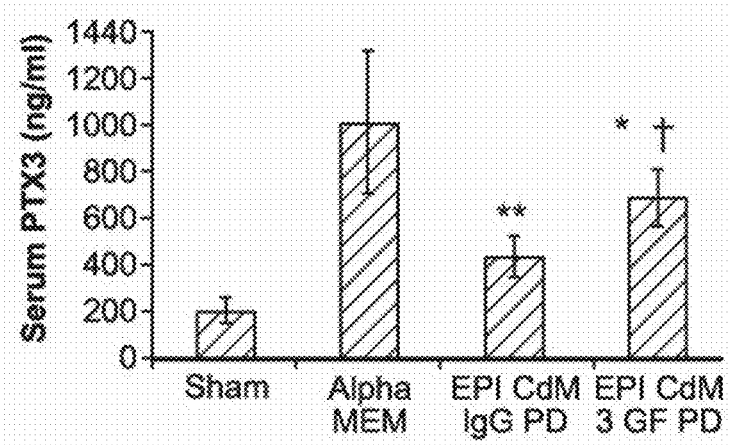
Figure 18A:
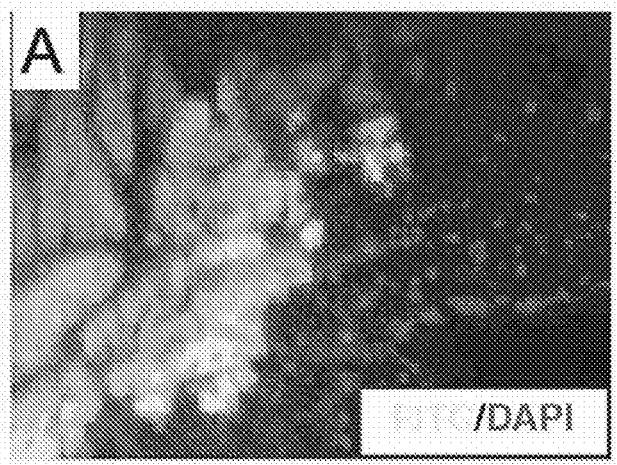
FIGS. 18A-18C depict images of a FITC-Alb extravasation assay for vascular integrity after MI and reperfusion.
Figure 18B:
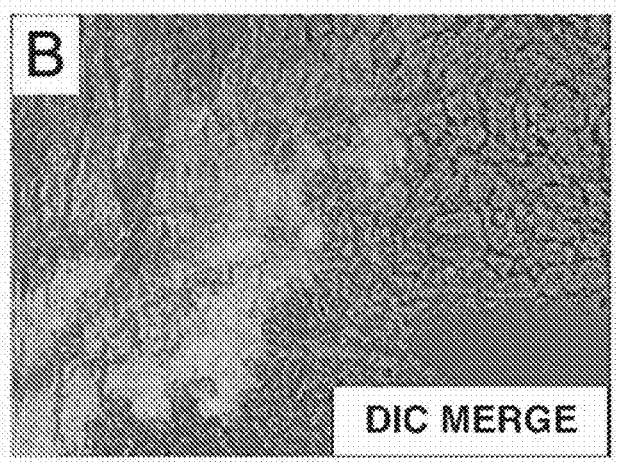
Figure 18C:
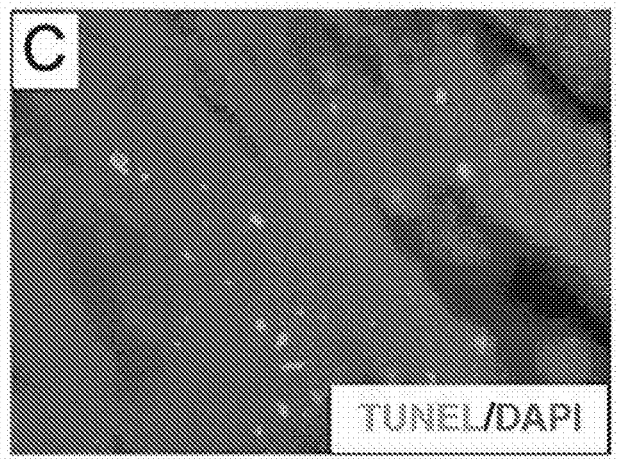

Compared with Alpha MEM treatment, IgG-PD treatment significantly reduced the LV mural volume of FITC-Alb, indicating that EPI CdM treatment protects against vascular rhexis that occurs after reperfusion (FIGS. 17E and 17F). By contrast, 3 GF PD treatment did not protect against vascular rhexis. In fact, the LV volume containing FITC-Alb in mice that received 3 GF PD did not differ from that of Alpha MEM-treated controls (FIGS. 17E and 17F).

For an independent measure of vascular rhexis, blood serum samples obtained from the same mice at 24 hrs after reperfusion were assayed for the long pentraxin, PTX3, a marker of inflammation and vasculopathy after MI[29]. PTX3 expression increases in neutrophils, macrophages and endothelial cells after MI and is released by damaged/dying endothelial cells within hours of reperfusion following myocardial ischemia[29].

By ELISA, serum PTX3 levels increased markedly at 24 hrs after reperfusion in Alpha MEM control animals compared with sham-operated mice that had suture passed under the LAD but were not ligated (FIG. 17F). In agreement with the FITC-Alb data, serum PTX3 was significantly reduced in mice that had been treated with IgG-PD. Similarly, concentrations of PTX3 in serum of mice treated with 3 GF PD did not differ from those in Alpha MEM controls (FIG. 17F). Taken together, these data indicate that multiple factors present in EPI CdM act rapidly and in synergy to reduce cardiac necrosis and infarct expansion by preventing the progression of vascular rhexis[30] after reperfusion.

In patients with acute MI, concentrations of PTX3 in blood predict mortality[31]. Therefore, the results with PTX3 are consistent with a novel and clinically relevant approach of putative value for treatment after MI based on human EPI CdM or its ligands. Without intending to be bound to theory, EPI CdM treatment after MI prevents vascular rhexis, and permits reperfusion to salvage damaged cardiomyocytes through microvasculature.

Most studies that treat animal models of acute MI with adult stem/progenitor cells[6,32,33] or conditioned medium[9,10,24] employ a persistent coronary ligation[6,9,10,24,32,33], treat by intramuscular injection[6,9,10,24,32,33], and treat very early after MI (e.g. immediately[6,24,32], 30 min[9] or 1 hr[10,33] after ligation). The studies described herein, were performed under clinical circumstance, in which a period of myocardial ischemia is followed by revascularization. Despite a relatively long 4 hr interval of ischemia, intra-arterial administration of EPI CdM at the time of reperfusion was sufficient to provide substantial preservation of cardiac tissue and function. Because of the small size of the murine heart, EPI CdM was injected into the left ventriclular lumen for delivery into the coronary arterial blood after reperfusion. Without intending to be bound to theory, one may deliver EPI CdM or a defined combination of its ligands (with stabilizing carriers such as albumin) directly into coronary arteries at the time of percutaneous coronary intervention to obtain benefits in patients. Recently, CdM from porcine bone marrow MSCs was delivered through an intracoronary infusion catheter after 60 min of myocardial ischemia in pigs[34].

Without intending to be bound to theory, EPI CdM treatment has the potential to reduce the "no re-flow" phenomenon commonly observed after reperfusion in animal models[35,36] and in patients with MI[37]. No re-flow refers to compromised distal myocardial perfusion despite restoration of patency in macroscopic vessels. After MI and recanalization of an infarct-related artery, myocardial perfusion can become progressively impaired, despite relief of the coronary occlusion[38]. The extent of no re-flow is known to predict infarct expansion[36] and the results herein indicate that EPI CdM treatment rapidly reduces myocardial necrosis and infarct expansion after MI by preventing the progression of vascular rhexis that occurs following reperfusion.

The results described in the Examples above were obtained using the following methods and materials.
Isolation of Adult Human Epicardial Progenitor-Like Cells and EMT into Precursor Cells Right atrial appendages were obtained from consenting cardiac bypass patients in a protocol that was approved by the IRB of the University of Vermont. The appendages were transferred from the hospital to the UVM Stem Cell Core on ice in 50 ml conical tubes containing explant medium: Alpha MEM (Invitrogen, Carlsbad, Calif.), 10% FCS (lot selected for rapid growth of hMSCs, Atlanta Biologicals, Lawrenceville, Ga.), 100 units/ml penicillin, 100 µg/ml streptomycin, and 2 mM L-glutamine (Mediatech Inc., Hendron, Va.).
Method #1

In a cell culture hood, appendages were immediately rinsed in 1×PBS and any extracardiac fat was manually removed with fine scissors. The remaining tissue was transferred to a 100 cm² dish (Nunc, Thermo Fisher Scientific, Rochester, N.Y.) containing 1×PBS supplemented with 1 mg/mL collagenase/dispase (Roche Applied Science, Indianapolis, Ind.) in which it was minced into approximately 1 mm³ pieces with sterile scalpel blades (#23, World Precision Instruments, Sarasota, Fla.). The dish was placed into a sterile 37° C. humidified cell culture incubator (Thermo Forma, 5% $CO_2$) for 1.5 hours, with shaking every 10 minutes. The resulting tissue digest was collected and centrifuged at 600×g for 5 min. The pellet was resuspended and washed in 25 mls of explant medium and centrifuged again. The final pellet was resuspended in 20 mls of explant medium and the digested fragments were split between 2 uncoated 100 cm² dishes. After 2-3 days, the dishes were supplemented by the addition of 5 mls of explant medium and then left undisturbed to allow for the adherence of tissue fragments.

After 5-7 days, when fibroblast outgrowth from the explants had nearly reached confluence, the dishes were washed once by PBS and the explant medium was changed to a medium that favored stem/progenitor cell growth: DMEM/F12 (Invitrogen) with 3% FCS (Atlanta Biologicals) and 20 ng/ml EGF, 10 ng/ml bFGF, 10 ng/ml LIF (all growth factors from Sigma, Saint Louis, Mo.), 1×ITS plus (BD Biosciences, San Jose, Calif.), 100 units/ml penicillin, 100 µg/ml streptomycin, and 2 mM L-glutamine (Mediatech Inc.).

After 2-3 days, areas of epicardial progenitor cells were observed proliferating in between the fibroblasts. The progenitor cells were morphologically distinguishable from surrounding cell types, did not mix with surrounding cells, and formed floating spheroids and cell aggregates that resembled bunches of grapes as they divided upwards into the medium rather than horizontally. By shaking the dishes and washing once with calcium- and magnesium-free PBS, the floating progenitor cells were collected. The resulting cells (epicardial progenitor-like cells) were cultured in petri dishes (uncharged) in stem/progenitor growth medium for up to several weeks (in some cases up to 2 months).

The epicardial nature of the cells was clear as all of the cells were epithelial and expressed Keratin proteins. Under these conditions, the epithelial cells continued to produce floating cells. To induce EMT, the epicardial cells were collected, centrifuged at 600×g for 5 min, resuspended in Claycomb medium (SAFC Biosciences, Sigma) with 10% FCS, 100 units/ml penicillin, 100 µg/ml streptomycin, and 2 mM L-glutamine, and transferred to new dishes. Following adherence to culture plastic, the majority of the progenitor-like cells underwent EMT within 3 days into precursor cells and expanded rapidly in the Claycomb medium with 10% FCS.

Whether long-term growth in the stem/progenitor cell medium (low serum with growth factors) and in uncoated petri dishes were important to generate the precursor cells at the next stage of culture was examined. This was not the case as primary floating epithelial progenitor cells obtained directly from initial the feeder layer cultures could also undergo EMT when plated onto typical positively-charged cell culture dishes and incubated in the Claycomb medium with 10% FCS. Furthermore, immunocytochemistry, cell surface phenotyping, and ELISA data indicated that the precursor cells derived from EMT did not differ whether the cells were rapidly induced to undergo EMT or were maintained for several weeks as epithelial progenitor cells and then induced to undergo EMT.

Method #2

A faster method was developed involving isolating EDPCs by direct culture of human epicardium dissected from the surface of right atrial appendages (FIGS. 1M-1P). Epicardial explants were cultured for up to 7 days in explant medium to allow outgrowth of epithelial cells. Upon switching to the adult stem/progenitor medium as above, the epithelial cells similarly became refractile and formed spheres and "bunches of grapes". These progenitor-like cells also expressed Keratins and could be induced to undergo EMT into EDPCs in Claycomb medium containing 10% FCS (as above). Cell surface phenotyping showed that EDPCs generated by method#1 or method#2 expressed identical antigen profiles (for comparison see, e.g., FIGS. 3A and 3B).

Immunocytochemistry and Immunohistochemistry

Atrial precursor cells were cultured for 2 days in Claycomb expansion medium in Labtek chamber slides (Nunc). They were washed once with PBS and fixed by a 10 minute incubation in 4% paraformaldehyde in phosphate buffered saline (PBS). Following several PBS washes, the chamber slides were blocked for 1 hour with 5% goat serum with 0.4% Triton-X 100 in PBS. Primary antibodies were diluted into blocking solution, placed on the cells, and incubated overnight at 4° C. (see below, antibody list and dilutions). Following 3× PBS washes, secondary antisera was applied in blocking buffer and incubated for 1 hour at room temperature. After 3 more washes, slides were mounted and coverslipped (Vectashield with DAPI, Vector laboratories, Burlingame, Calif.) and viewed with an epifluorescence microscope (Leica DM6000B with DFC350 FX camera). Double immunohistochemistry was performed as in Spees et al. 2008 (FASEB J. April; 22(4):1226-36).

Primary Antisera:

| | |
|---|---|
| Smooth muscle myosin heavy chain, SMMS-1, Dako, Carpinteria, CA | 1:100 |
| Von Willebrand Factor, F8/86, Dako | 1:50 |
| Human STRO-1, MAB1038, R and D Systems, Minneapolis, MN | 5 µg/mL |
| GATA 4, G-4, Santa Cruz Biotechnology, Santa Cruz, CA | 1:100 |
| Nkx 2.5, H-114, Santa Cruz | 1:50 |
| Cytokeratin (mixture), C2562, Sigma | 1:100 |
| Alpha smooth muscle actin, clone 1A4, A2547, Sigma | 1:800 |
| Sarcomeric actin, A2172, Sigma | 1:500 |
| SERCa2 ATPase, clone IID8, S1439, Sigma | 1:400 |
| Cardiac calsequestrin, C2491, Sigma | 10 µg/mL |
| Connexin 43, C6219, Sigma | 1:400 |
| Connexin 40, 36-4900, Zymed Laboratories (Invitrogen) | 2 µg/ml |
| Epicardin (TCF21), ab32981, Abcam | 1:100 |
| Myosin light chain phospho S20, ab2480, Abcam | 1:100 |
| Vimentin, E2944, Spring Bioscience, Freemont, CA | 1:200 |

Secondary Antisera:

| | |
|---|---|
| Goat anti-mouse IgG ALEXA 594, Molecular Probes, Invitrogen | 1:800 |
| Goat anti-mouse IgG ALEXA 488, Molecular Probes, Invitrogen | 1:500 |
| Goat anti-mouse IgM ALEXA 594, Molecular Probes, Invitrogen | 1:800 |
| Goat anti-rabbit IgG ALEXA 594, Molecular Probes, Invitrogen | 1:800 |
| Goat anti-rabbit IgG ALEXA 488, Molecular Probes, Invitrogen | 1:500 |
| Donkey anti-goat IgG ALEXA 594, Molecular Probes, Invitrogen | 1:800 |

Reverse Transcriptase Polymerase Chain Reaction (RT-PCR)

Total RNA was isolated from cell pellets using a commercial kit (RNAqueous, Ambion, Austin, Tex.). To avoid the possibility of contaminating DNA, the total RNA samples were treated with DNase prior to reverse transcription (TURBO DNase, Ambion). Reverse transcription was performed with Superscript III (Invitrogen) in the presence of RNase inhibitor (RNaseOUT, Invitrogen). PCR was carried out using an Eppendorf Master Cycler EP thermal cycler. Control RT-PCR reactions included template samples in which the reverse transcriptase was omitted from the single strand synthesis reaction. Primer sequences and annealing temperatures are listed below. Target sequences were denatured at 94° C. (2 minutes) followed by 30 amplification cycles of 94° C. (30 seconds), anneal temp (30 seconds), and 72° C. (45 seconds). The last PCR step extended the products at 72 C for 1 minute. RT-PCR products were analyzed on 1% agarose gels.

PCR Primers:

| | | Tm ° C. |
|---|---|---|
| Cardiac alpha actin | | |
| Forward | 5' TGC TGA TCG TAT GCA GAA GG 3' (SEQ ID NO: 1) | 54.8 |
| Reverse | 5' GCT GGA AGG TGG ACA GAG AG 3' (SEQ ID NO: 2) | 57.3 |
| MLC4 | | |
| Forward | 5' AAG ATC ACC TAC GGC CAG TG 3' (SEQ ID NO: 3) | 56.8 |
| Reverse | 5' CCC TCC ACG AAG TCC TCA TA 3' (SEQ ID NO: 4) | 55.8 |
| SERCA2a | | |
| Forward | 5' GGT GCT GAA AAT CTC CTT GC 3' (SEQ ID NO: 5) | 54.3 |
| Reverse | 5'ATC AGT CAT GCA CAG GGT TG 3' (SEQ ID NO: 6) | 55.3 |
| MLC2a | | |
| Forward | 5' GTC TTC CTC ACG CTC TTT GG 3' (SEQ ID NO: 7) | 55.7 |
| Reverse | 5' CCA CCT CAG CTG GAG AGA AC 3' (SEQ ID NO: 8) | 57.3 |
| MLC2v | | |
| Forward | 5' GGT GCT GAA GGC TGA TTA CGT T 3' (SEQ ID NO: 9) | 56.7 |
| Reverse | 5' TAT TGG AAC ATG GCC TCT GGA T 3' (SEQ ID NO: 10) | 56.1 |
| GAPDH | | |
| Forward | 5' GCT GAG TAC GTC GTG GAG T 3' (SEQ ID NO: 11) | 56.6 |
| Reverse | 5' CAC CAC TGA CAC GTT GGC A 3' (SEQ ID NO: 12) | 58.3 |
| Cx43 | | |
| Forward | 5' AGG CGT GAG GAA AGT ACC AA 3' (SEQ ID NO: 13) | 56.2 |
| Reverse | 5' ACA CCT TCC CTC CAG CAG TT 3' (SEQ ID NO: 14) | 58.7 |
| Myocardin | | |
| Forward | 5' GGA CTG CTC TGG CAA CCC AGT GC 3' (SEQ ID NO: 15) | 64.7 |
| Reverse | 5' CAT CTG ACT CCG GGT CAT TTG C 3' (SEQ ID NO: 16) | 61.9 |
| vWF | | |
| Forward | 5' AAG AAC CGA AGT CCC AGG AGA AAG G 3' (SEQ ID NO: 17) | 61.5 |
| Reverse | 5' AGA TTT CAG AGG CGT TCT AAA ACT CA 3' (SEQ ID NO: 18) | 58.4 |
| Smooth muscle alpha actin | | |
| Forward | 5' GAA GAG GAC AGC ACT GCC T 3' (SEQ ID NO: 19) | 57.1 |
| Reverse | 5' CTG ATA GGA CAT TGT TAG CAT A 3' (SEQ ID NO: 20) | 49.6 |

|  |  | Tm ° C. |
|---|---|---|
| GATA4 | | |
| Forward | 5' GAC GGG TCA CTA TCT GTG CAA C 3'<br>(SEQ ID NO: 21) | 57.8 |
| Reverse | 5' AGA CAT CGC ACT GAC TGA GAA C 3'<br>(SEQ ID NO: 22) | 56.8 |
| GATA5 | | |
| Forward | 5' CAC AAG ATG AAT GGC GTC AA 3'<br>(SEQ ID NO: 23) | 53.5 |
| Reverse | 5' CTT CCG TGT CTG GAT GCT TT 3'<br>(SEQ ID NO: 24) | 55.2 |
| Tbx18 | | |
| Forward | 5' GGG GAG ACT TGG ATG AGA CA 3'<br>(SEQ ID NO: 25) | 56.1 |
| Reverse | 5' AGC AAG AGG AGC CAG ACA AA 3'<br>(SEQ ID NO: 26) | 56.5 |
| Tbx5 | | |
| Forward | 5' ACG TGC TCA GTT TTG CCT CT 3'<br>(SEQ ID NO: 27) | 57.2 |
| Reverse | 5' CAG TTT TGT GTT GGC ATT GG 3'<br>(SEQ ID NO: 28) | 53.0 |
| Wt1 | | |
| Forward | 5' CGG GGG TGA ATC TTG TCT AA 3'<br>(SEQ ID NO: 29) | 54.2 |
| Reverse | 5' CCT GGA CCA TCC CCT ATT TT 3'<br>(SEQ ID NO: 30) | 54.2 |
| Isl-1 | | |
| Forward | 5' GTA GAG ATG ACG GGC CTC AG 3'<br>(SEQ ID NO: 31) | 56.9 |
| Reverse | 5' TTT CCA AGG TGG CTG GTA AC 3'<br>(SEQ ID NO: 32) | 55.3 |
| Mef2C | | |
| Forward | 5' CTG GGA AAC CCC AAC CTA TT 3'<br>(SEQ ID NO: 33) | 54.7 |
| Reverse | 5' GCT GCC TGG TGG AAT AAG AA 3'<br>(SEQ ID NO: 34) | 55.1 |

Characterization of Cell Surface Epitopes

Pellets of $0.5 \times 10^6$ to $1 \times 10^6$ cells were suspended in 0.5 ml PBS and were incubated for 30 minutes at 4° C. with monoclonal mouse anti-human antibodies that were pre-titered for flow cytometry. All antibodies except those against CD133 (Miltenyi Biotech) and CD105 and NG2 (Beckman Coulter, Miami, Fla.) were purchased from BD Biosciences Pharmingen (San Diego, Calif.). After labeling, the cells were washed twice with PBS and analyzed by closed-stream flow cytometry (LSR II, Becton Dickinson, Franklin Lakes, N.J.).

Pulldown (PD) of Growth Factors from EPI CdM

For pulldown (PD) of HGF from EPI CdM, 2 μg of biotinylated human HGF antisera in 100 ul of PBS was added to 1 ml of 30× EPI CdM and incubated at 4° C. overnight. Separate incubations were performed with 2 μg of biotinylated non-specific IgG to produce control 30× EPI CdM. For simultaneous PD of 3 growth factors from EPI CdM, 2 μg each of biotinylated anti-HGF, anti-VEGF, anti-SDF, or biotinylated IgG (for control) in 100 ul of PBS were added (in combination) to 1 ml of 30× EPI CdM and incubated at 4° C. overnight. The following day 0.1 ml of 50% suspension Streptavidin Agarose resin (Pierce, Thermo Scientific) in PBS was added to each sample and incubated for 2 h at 4° C. with slow rotation. Supernatants were removed after a centrifugation to remove agarose, filtered through 0.22 um syringe filters (Acrodisk) and stored frozen until use. Biotinylated antisera were obtained from R and D Systems.

Myocardial Infarction

Male mice at 8 weeks of age underwent ischemia-reperfusion myocardial infarction (MI-IR) surgery (immunodeficient mice: NOD-SCID, NOD-SCID IL2Rγ$^{-/-}$, and NOD-SCID β2$^{-/-}$, Jackson Labs, Bar Harbor, Me.; immunocompetant mice, C57 bl6/J, Taconic, Hudson, N.Y.). Immunodeficient mice were maintained on a Sulfa-Trim diet and were housed in a standard barrier facility environment. Any mice with abnormalities in weight, general health, or cardiac health were not included in the study. Mice were also not included in the study if they did not survive the initial myocardial infarction surgery, did not achieve a successful myocardial infarction (as determined by blanching observed at time of treatment), or died during treatment application. Following all procedures, mice were given analgesia (buprenorphine, 0.05-0.1 mg/kg i.p.) and monitored for signs of distress until termination of the study. All procedures were done in accordance with the University of Vermont IACUC (protocol 08-016).

For the MI-IR surgery, mice were anesthetized using 2-4% IsoFlurane, shaved, weighed, intubated, and then maintained for the duration of the procedure on a sterile surgical field using a mechanical ventilation system (Mini-Vent, Harvard Apparatus, Holliston, Mass.). Throughout the surgery and during the recovery period, body temperatures were maintained with a heated water pad system (Gaymar T-Pump TP-500, Gaymar Industries, Orchard Park, N.Y.). Viewing the chest through a dissecting microscope (Stemi 2000-C, Carl Zeiss MicroImaging, Thornwood, N.Y.) a dermal incision was made, the underlying fascia were removed, and the thoracic musculature was retracted to expose the left ribcage. Next the intercostal muscles were retracted and the outer (parietal or visceral) pericardium was removed to expose the left coronary artery descending (LCAD). The LCAD was then ligated with 8.0 nylon suture (Henry Schein, Melville, N.Y.) and blanching within the myocardium of the left ventricle was noted. Finally, the intercostals were rejoined using a 6.0 nylon suture (Henry Schein), the lungs were reinflated, and overlying dermis rejoined with a 6.0 nylon suture. All mice were recovered to an ambulatory state prior to any subsequent treatment procedure, including reperfusion.

All surgical attempts and outcomes were extensively recorded, including the location of LCAD, suture placement (usually 2.0-3.0 mm from left atrial apex), area of blanching observed, and any complications noted. A surgery was considered successful if the mouse survived the initial myocardial infarction procedure, the suture remained in place for the appropriate time (4 hours), and tissue blanching below the suture was observed from initial ligation until reperfusion and/or treatment administration. Reperfusion was considered accomplished with a return of color to the previously blanched myocardium. The survival rate for the 4 hr MI-FR surgery was 90%.

Treatment Regimens

Following recovery of animals after initial suture placement, mice were again anesthetized, intubated, and the chest opened as described previously at 4 hrs after coronary ligation. Once the intact suture and area of blanching were confirmed and reperfusion was accomplished, 30× EPI CdM (200 uL) warmed to 37° C. was delivered to the entire cardiovascular arterial tree by injecting the solution into the lumen of the left ventricle (LV). This method was designed to deliver a maximum amount of EPI CdM to the injured myocardium by employing the naturally existing arterial network of the heart, which is supplied by the immediate portion of the aorta. With a 30.5 gauge needle inserted below the great cardiac vein (LV apex) at an angle 45° to the myocardium, 200 uL of 30× EPI CdM warmed to 37° C. was slowly injected over a period of 1 minute. Control animals received 200 ul of Alpha MEM (vehicle) in the same manner. All animals were randomized to treatment at the end of the first surgery (after ligation). Following treatment with either EPI CdM or vehicle, the needle was removed and the intercostals were rejoined using 6.0 chromic gut suture (Ethicon, Johnson and Johnson, Inc., Livingston, UK), lungs then reinflated, and overlying dermis rejoined with 6.0 nylon suture. All mice were then recovered to an ambulatory state and transferred to the vivarium for the remaining duration of the experiment. The survival rate for treated immunodeficient mice was: Alpha MEM, 71%; EPI CdM, 75%. The survival rate for treated immunocompetent mice was: Alpha MEM, 43%; EPI CdM, 86%.

Echocardiography

Two dimensional, Doppler, and M-Mode echocardiography was performed with a Vevo 770 High-Resolution Imaging System (VisualSonics, Toronto, ON, Canada). Data was recorded from sham-operated mice, control mice with myocardial infarction, and treated mice with myocardial infarction while under isoflurane anesthesia. All left ventricular dimensions in systole and diastole were measured from M-mode images obtained at the mid-papillary muscle level. Echocardiographic data were coded for unbiased measurements and determination of ECHO wall motion scores. ECHO scores were determined from functional assessment of 13 segments using a model based on the American Society of Echocardiography 17 segment model. Systolic wall motion scores were assigned to 4 quadrants each of 3 short axis segments taken at apical, mid papillary, and basal levels, with an additional segment at the apex (13 total). Scores were assigned as: 1=normal, >25% motion; 2=hypokinetic, 10-25% motion; 3=akinetic, <10% motion. Pulmonary arterial Doppler flow velocities and volumes were quantified as in Baumann et al., 2008 Echocardiography. 25: 739-748.

Following ECHO, the mice were killed humanely by exsanguination and the hearts were removed and rinsed in PBS. For creatine kinase assays, left ventricular tissue was dissected away from the atria and the aorta, further separated into anterior left ventricle and posterior left ventricle/septum, and immediately snap frozen by submersion of cryovials in liquid $N_2$. The LV tissues were maintained at $-80°$ C. until the day of the creatine kinase assay. For histology, the ventricles were dissected and rinsed in PBS. They were fixed for 2 days in 4% paraformaldehyde in PBS at 4° C. After fixation, the ventricles were cut transversely across the mid portion of the infarct zone, and placed into 70% ethanol prior to paraffin imbedding. Serial sections were cut from each of the two halves to section the entire heart from apex to base.

Creatine Kinase Assay

The remaining creatine kinase (CK) activity in left ventricular tissues was assessed to determine the extent of infarction (Zaman et al. 2009 Exp Biol Med (Maywood). 234: 246-254). The loss of creatine kinase activity directly reflects the loss of viable myocardium after myocardial infarction (Kjekshus and Sobel. 1970 Circ Res 27:403-414; Roberts et al. 1975 Circulation 52: 743-754; Shell et al. 1973. J Clin Invest 52: 2579-2590). The percentage of left ventricle with infarction was calculated based on observed total left ventricular creatine kinase activity (IU/mg protein) in left ventricles of normal hearts without infarction. The percent of myocardial infarction=100×[NL CK−LV CK]/Δ, where NL CK normal left ventricle creatine kinase activity is the amount of CK in tissue from normal left ventricle (IU/mg of soluble protein), left ventricle creatine kinase is total remaining creatine kinase activity in the left ventricle after myocardial infarction (IU/mg soluble protein), and Δ is the difference between the amount of creatine kinase in normal zones of myocardium and in zones of myocardium with infarction.

Statistical Analysis.

All values are expressed as mean±SEM unless otherwise indicated. Comparisons of parameters among the three groups were made using one-way analysis of variance (ANOVA) followed by Scheffé's multiple comparison test.

Comparisons of parameters between two groups were made by unpaired Student's t-test. P<0.05 was considered significant.

The results described in Examples 3-5 were carried out using the following methods and materials.

Epicardial Precursor Cell Conditioned Medium (EPI CdM).

After EMT, passage 3 epicardial precursor cells were seeded and grown in Claycomb expansion medium on 150 cm$^2$ dishes (Nunc). When the cells reached 90% confluence, the plates were washed twice with PBS and serum-free alpha MEM was placed on the cells (20 mls per plate). After 48 hours of incubation, the CdM was collected, filtered (0.2 μm PES membrane, Nalgene MF75, Rochester, N.Y.), and concentrated 30-fold with a Labscale™ TFF diafiltration system with the use of filters with a 5 kD cut-off (Millipore, Bedford, Mass.). Medium components above 5 kD were concentrated (base medium components and salts remained at 1×). One ml vials of CdM were frozen and stored at −80° C. Some of the EPI CdM was kept at 1× (unconcentrated) for ELISAs and cell protection assays with primary human cardiac endothelial cells. ELISAs for human growth factors were performed with commercially available kits (R and D systems).

Cell Protection Assays with EPI CdM

Primary human aortic and coronary artery endothelial cells were purchased and cultured in EGM-2MV (Cambrex, Lonza). For cell protection assays under simulated ischemia, endothelial cells were seeded at 10,000 cells/cm$^2$ into 24 well plates (Nunc) containing growth medium and allowed to incubate for 2 days under normoxic conditions. For experiments, the cells were washed once with PBS and the medium was switched to either growth medium, alpha MEM base medium, 1× EPI CdM, or 10× EPI CdM. After changing the medium, the cells were then incubated in a dedicated incubator set to 1% oxygen for 24 or 48 hrs. For neutralization studies, monoclonal antisera against HGF or VEGF were added to EPI CdM, incubated for 30 min at RT, and spun down (HGF, H1896; VEGF, V4758; Sigma). For controls, non-specific mouse IgG (Sigma) was added to EPI CdM at the same concentration and incubated similarly. Cell viability (metabolism) was determined by MTS assay (CellTiter 96 AQueousOne Solution Cell Proliferation Assay, Promega). Cell number was quantified by dye binding of nucleic acids (CyQuant Assay, Molecular Probes, Invitrogen).

FITC-Alb Extravasation Assay for Vascular Integrity

At 22 hr after MI, reperfusion and treatment (2 hr before euthanization), 200 ul of FITC-conjugated albumin (5 mg/ml in PBS, Sigma) was injected by tail vein. Hearts were removed, fixed in 4% paraformaldehyde in PBS, processed in O.C.T. Compound (Tissue Tek), and serially sectioned from apex to base on a cryostat to 40 micron thickness. TUNEL staining was performed on all sections using a commercially available kit (In Situ Cell Death Detection Kit, tetramethyl rhodamine version, Roche Applied Science).

For each LV section, multiple photomicrographs were obtained at 5× magnification to image the entire LV and were montaged in Adobe Photoshop. Total LV areas and FITC-positive areas were determined from composite, flattened montages with Scion Image Software. LV volumes and FITC-positive volumes were estimated using measurements from 6-7 sections that were equi-distant from each other and that spanned the entire zone of infarction. The volumes between sections were estimated by averaging the section areas for total LV and FITC-positive LV and multiplying by the distance between the sections (typically 720 microns). For TUNEL scoring of FITC-Alb sections, separate images were obtained outside, at border areas, and inside the FITC-positive area for each section.

Determination of PTX3 in Blood Serum

Immediately before removing hearts for fixation and sectioning for the FITC-Alb assay, blood was collected by syringe from the left ventricular lumen, allowed to clot, and then centrifuged to collect serum. Due to the relatively high concentrations of circulating PTX3 in blood of animals with MI, serum samples were diluted in buffer prior to ELISA. Murine PTX3 was measured by ELISA according to the manufacturer's instructions (R & D Systems).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

The following documents are cited herein.
1. Beltrami, A. P. et al. Adult cardiac stem cells are multipotent and support myocardial regeneration. Cell 114, 763-776 (2003).
2. Dawn, B. et al. Cardiac stem cells delivered intravascularly traverse the vessel barrier, regenerate infarcted myocardium, and improve cardiac function. Proc. Natl. Acad. Sci. USA. 102, 3766-3771 (2005).
3. Amado, L. C. et al. Cardiac repair with intramyocardial injection of allogeneic mesenchymal stem cells after myocardial infarction. Proc. Natl. Acad. Sci. USA 102, 11474-11479 (2005).
4. Kawamoto, A. et al. CD34-positive cells exhibit increased potency and safety for therapeutic neovascularization after myocardial infarction compared with total mononuclear cells. Circulation 114, 2163-2169 (2006).
5. Iso, Y. et al. Multipotent human stromal cells improve cardiac function after myocardial infarction in immunodeficient mice without long-term engraftment. Biochem. Biophys. Res. Com. 354, 700-706 (2007).
6. Winter, E. M. et al. Preservation of left ventricular function and attenuation of remodeling after transplantation of human epicardium-derived cells into the infarcted mouse heart. Circulation 116, 917-927 (2007).
7. Smith, R. R. et al. Regenerative potential of cardiosphere-derived cells expanded from percutaneous endomyocardial biopsy specimens. Circulation 115, 896-908 (2007).
8. Gnecchi, M., Zhang, Z., Ni, A., & Dzau, V. J. Paracrine mechanisms in adult stem cell signaling and therapy. Circ. Res. 103, 1204-1219 (2008). Review.
9. Gnecchi, M. et al. Paracrine action accounts for marked protection of ischemic heart by Akt-modified mesenchymal stem cells. Nat. Med. 11, 367-368 (2005).

10. Gnecchi, M. et al. Evidence supporting paracrine hypothesis for Akt-modified mesenchymal stem cell-mediated cardiac protection and functional improvement. FASEB J. 20, 661-669 (2006).
11. Lee, R. H. et al. The CD34-like protein PODXL and alpha6-integrin (CD49f) identify early progenitor MSCs with increased clonogenicity and migration to infarcted heart in mice. Blood 113, 816-826 (2009).
12. Johnston, P. V. et al. Engraftment, differentiation, and functional benefits of autologous cardiosphere-derived cells in porcine ischemic cardiomyopathy. Circulation 120, 1075-1083 (2009).
13. Gittenberger-de Groot, A. C., Vrancken Peeters, M. P., Bergwerff, M., Mentink, M. M., & Poelmann, R. E. Epicardial outgrowth inhibition leads to compensatory mesothelial outflow tract collar and abnormal cardiac septation and coronary formation. Circ. Res. 87, 969-971 (2000).
14. Eralp, I. et al. Coronary artery and orifice development is associated with proper timing of epicardial outgrowth and correlated Fas-ligand-associated apoptosis patterns. Circ. Res. 96, 526-534 (2005).
15. Dettman, R. W., Denetclaw, W. Jr., Ordahl, C. P., & Bristow, J. Common epicardial origin of coronary vascular smooth muscle, perivascular fibroblasts, and intermyocardial fibroblasts in the avian heart. Dev. Biol. 193, 169-181 (1998).
16. Vrancken Peeters, M. P., Gittenberger-de Groot, A. C., Mentink, M. M., & Poelmann, R. E. Smooth muscle cells and fibroblasts of the coronary arteries derive from epithelial¬ mesenchymal transformation of the epicardium. Anat. Embryol. (Berl). 199, 367-378 (1999).
17. Pérez-Pomares, J. M. et al. Origin of coronary endothelial cells from epicardial mesothelium in avian embryos. Int. J. Dev. Biol. 46, 1005-1013 (2002).
18. Zhou, B. et al. Epicardial progenitors contribute to the cardiomyocyte lineage in the developing heart. Nature 454, 109-113 (2008).
19. Cai, C. L. et al. A myocardial lineage derives from Tbx18 epicardial cells. Nature 454, 104-108 (2008).
20. Eralp, I. et al. Epicardium-derived cells are important for correct development of the Purkinje fibers in the avian heart. Anat. Rec. A Discov. Mol. Cell Evol. Biol. 288, 1272-1280 (2006).
21. Eid, H. et al. Role of epicardial mesothelial cells in the modification of phenotype and function of adult rat ventricular myocytes in primary coculture. Circ. Res. 71, 40-50 (1992).
22. Chen, T. H. et al. Epicardial induction of fetal cardiomyocyte proliferation via a retinoic acid-inducible trophic factor. Dev Biol. 250, 198-207 (2002).
23. Lepilina, A. et al. A dynamic epicardial injury response supports progenitor cell activity during zebrafish heart regeneration. Cell 127, 607-619 (2006).
24. Zhou, B. et al. Adult mouse epicardium modulates myocardial injury by secreting paracrine factors. J Clin Invest. 121, 1894-1904 (2011).
25. Kjekshus, J. K., & Sobel, B. E. Depressed myocardial creatine phosphokinase activity following experimental myocardial infarction in rabbit. Circ. Res. 27, 403-414 (1970).
26. Shell, W. E., Lavelle, J. F., Covell, J. W., & Sobel, B. E. Early estimation of myocardial damage in conscious dogs and patients with evolving acute myocardial infarction. J. Clin. Invest. 52, 2579-2590 (1973).
27. Roberts, R., Henry, P. D., & Sobel, B. E. An improved basis for enzymatic estimation of infarct size. Circulation 52, 743-754 (1975).
28 French, C. J., Spees, J. L., Zaman, A. K., Taatjes, D. J., & Sobel, B. E. The magnitude and temporal dependence of apoptosis early after myocardial ischemia with or without reperfusion. FASEB J. 23, 1177-1185 (2009).
29. Salio, M. et al. Cardioprotective function of the long pentraxin PTX3 in acute myocardial infarction. Circulation 117, 1055-1064 (2008).
30. Tarikuz Zaman, A. K. M., French, C. J., Spees, J. L., Binbrek, A. S., & Sobel, B. E. Vascular rhexis in mice subjected to non-sustained myocardial ischemia and its therapeutic implications. Exp. Biol. Med. (Maywood) 236, 598-603 (2011).
31. Latini, R. et al. Prognostic significance of the long pentraxin PTX3 in acute myocardial infarction. Circulation 110, 2349-2354 (2004).
32. Deuse, T. et al. Hepatocyte growth factor or vascular endothelial growth factor gene transfer maximizes mesenchymal stem cell-based myocardial salvage after acute myocardial infarction. Circulation 120, S247-S254 (2009).
33. Mangi, A. A. et al. Mesenchymal stem cells modified with Akt prevent remodeling and restore performance of infarcted hearts. Nat. Med. 9, 1195-1201 (2003).
34. Nguyen et al. Improved function and myocardial repair of infarcted heart by intracoronary injection of mesenchymal stem cell-derived growth factors. J Cardiovasc. Trans. Res. 3, 547-558 (2010).
35. Kloner, R. A., Ganote, C. E., & Jennings, R. B. The "no-reflow" phenomenon after temporary coronary occlusion in the dog. J Clin Invest. 54, 1496-1508 (1974).
36. Reffelmann, T., Hale, S. L., Dow, J. S., & Kloner, R. A. No-reflow phenomenon persists long-term after ischemia/reperfusion in the rat and predicts infarct expansion. Circulation 108, 2911-2917 (2003).
37. Ragosta, M. et al. Microvascular integrity indicates myocellular viability in patients with recent myocardial infarction. New insights using myocardial contrast echocardiography. Circulation 89, 2562-2569 (1994).
38. Ambrosio, G., Weisman, H. F., Mannisi, J. A., & Becker, L. C. Progressive impairment of regional myocardial perfusion after initial restoration of postischemic blood flow. Circulation 80, 1846-1861 (1989).

What is claimed is:

1. A pharmaceutical composition consisting of secreted cellular factors in a pharmaceutically acceptable excipient, wherein the cellular factors:
- are isolated from a cultured epicardial progenitor cell selected for expression of epicardin, IsI-I, GATA 5, WT1, Tbx1 8, and Tbx5 polypeptides;
- have a biological activity selected from the group consisting of reducing cell death in a cell population at risk thereof, increasing cell survival, reducing inflammation, increasing epicardial cell proliferation, increasing epithelial to mesenchymal transformation, and increasing cardiac function;
- have a molecular weight that is at least about 5 kD; and
- are capable of being inactivated by heat denaturation.

2. The pharmaceutical composition of claim 1, wherein the secreted cellular factors include HGF, VEGF, SDF-1 alpha, or IGF-1.

3. The pharmaceutical composition of claim 2, wherein the amount of HGF is between about 3-500 ng/ml, VEGF is between about 0.5-500 ng/ml, SDF-I alpha is between about 0.15 ng-500 ng/ml, and IGF-I is between about 0.03 ng-500 ng/ml.

4. The pharmaceutical composition of claim 1, wherein the epicardial progenitor cell is negative for c-kit and CD31.

* * * * *

SEQUENCE LISTING

<160> NUMBER OF SEQ ID NOS: 45

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tgctgatcgt atgcagaagg                                          20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctggaaggt ggacagagag                                          20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagatcacct acggccagtg                                          20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccctccacga agtcctcata                                          20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtgctgaaa atctccttgc                                          20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcagtcatg cacagggttg                                          20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 7
gtcttcctca cgctctttgg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccacctcagc tggagagaac                                              20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtgctgaag gctgattacg tt                                           22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tattggaaca tggcctctgg at                                           22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctgagtacg tcgtggagt                                               19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caccactgac acgttggca                                               19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 13
aggcgtgagg aaagtaccaa                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acaccttccc tccagcagtt                                                    20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggactgctct ggcaacccag tgc                                                23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
catctgactc cgggtcattt gc                                                 22

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagaaccgaa gtcccaggag aaagg                                              25

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agatttcaga ggcgttctaa aactca                                             26

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaagaggaca gcactgcct                                                19

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgataggac attgttagca ta                                            22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gacgggtcac tatctgtgca ac                                            22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agacatcgca ctgactgaga ac                                            22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cacaagatga atggcgtcaa                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cttccgtgtc tggatgcttt                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggggagactt ggatgagaca                                            20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agcaagagga gccagacaaa                                            20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acgtgctcag ttttgcctct                                            20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagttttgtg ttggcattgg                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29 cggggtgaa tcttgtctaa                                             20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctggaccat cccctatttt                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtagagatga cgggcctcag                                            20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tttccaaggt ggctggtaac                                            20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctgggaaacc ccaacctatt                                            20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gctgcctggt ggaataagaa                                            20

<210> SEQ ID NO 35
<211> LENGTH: 179
<212> TYPE: PRT
<213> ORGANISM: Homo sapiens

<400> SEQUENCE: 35

Met Ser Thr Gly Ser Leu Ser Asp Val Glu Asp Leu Gln Glu Val
1               5                   10                  15

Met Leu Glu Cys Asp Gly Leu Lys Met Asp Ser Asn Lys Glu Phe Val
                20                  25                  30

Thr Ser Asn Glu Ser Thr Glu Glu Ser Ser Asn Cys Glu Asn Gly Ser
            35                  40                  45

Pro Gln Lys Gly Arg Gly Gly Leu Gly Lys Arg Lys Ala Pro Thr
        50                  55                  60

Lys Lys Ser Pro Leu Ser Gly Val Ser Gln Glu Gly Lys Gln Val Gln
65                  70                  75                  80

Arg Asn Ala Ala Asn Ala Arg Glu Arg Ala Arg Met Arg Val Leu Ser
                85                  90                  95

Lys Ala Phe Ser Arg Leu Lys Thr Thr Leu Pro Trp Val Pro Pro Asp
            100                 105                 110

Thr Lys Leu Ser Lys Leu Asp Thr Leu Arg Leu Ala Ser Ser Tyr Ile
        115                 120                 125

Ala His Leu Arg Gln Ile Leu Ala Asn Asp Lys Tyr Glu Asn Gly Tyr
    130                 135                 140

Ile His Pro Val Asn Leu Thr Trp Pro Phe Met Val Ala Gly Lys Pro
145                 150                 155                 160

Glu Ser Asp Leu Lys Glu Val Val Thr Ala Ser Arg Leu Cys Gly Thr 165                 170                 175

Thr Ala Ser

<210> SEQ ID NO 36
<211> LENGTH: 324
<212> TYPE: PRT
<213> ORGANISM: Homo sapiens

<400> SEQUENCE: 36

Met Phe Pro Ser Pro Ala Leu Thr Pro Thr Pro Phe Ser Val Lys Asp
1               5                   10                  15

Ile Leu Asn Leu Glu Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Ala Pro Ala Phe Tyr Pro Arg Ala
                85                  90                  95

Tyr Ser Asp Pro Asp Pro Ala Lys Asp Pro Arg Ala Glu Lys Lys Glu
            100                 105                 110

Leu Cys Ala Leu Gln Lys Ala Val Glu Leu Glu Lys Thr Glu Ala Asp
        115                 120                 125

Asn Ala Glu Arg Pro Arg Ala Arg Arg Arg Lys Pro Arg Val Leu
    130                 135                 140

Phe Ser Gln Ala Gln Val Tyr Glu Leu Glu Arg Arg Phe Lys Gln Gln
145                 150                 155                 160

Arg Tyr Leu Ser Ala Pro Glu Arg Asp Gln Leu Ala Ser Val Leu Lys
                165                 170                 175

Leu Thr Ser Thr Gln Val Lys Ile Trp Phe Gln Asn Arg Arg Tyr Lys
            180                 185                 190

Cys Lys Arg Gln Arg Gln Asp Gln Thr Leu Glu Leu Val Gly Leu Pro
        195                 200                 205

Pro Pro Pro Pro Pro Ala Arg Arg Ile Ala Val Pro Val Leu Val
    210                 215                 220

Arg Asp Gly Lys Pro Cys Leu Gly Asp Ser Ala Pro Tyr Ala Pro Ala
225                 230                 235                 240

Tyr Gly Val Gly Leu Asn Pro Tyr Gly Tyr Asn Ala Tyr Pro Ala Tyr
                245                 250                 255

Pro Gly Tyr Gly Gly Ala Ala Cys Ser Pro Gly Tyr Ser Cys Thr Ala
            260                 265                 270

Ala Tyr Pro Ala Gly Pro Ser Pro Ala Gln Pro Ala Thr Ala Ala Ala
        275                 280                 285

Asn Asn Asn Phe Val Asn Phe Gly Val Gly Asp Leu Asn Ala Val Gln
    290                 295                 300

Ser Pro Gly Ile Pro Gln Ser Asn Ser Gly Val Ser Thr Leu His Gly
305                 310                 315                 320

Ile Arg Ala Trp

<210> SEQ ID NO 37
<211> LENGTH: 439
<212> TYPE: PRT
<213> ORGANISM: Homo sapiens

<400> SEQUENCE: 37

```
Met Tyr Gln Ser Leu Pro Trp Pro Pro Thr Thr Gly Arg Pro Pro Val
1               5                   10                  15

Pro Thr Arg Arg Ala Ala Pro Ala Pro Ser Cys Thr Ala Arg Ala Arg
                20                  25                  30

Pro Arg Gln Ser Thr Cys Pro His Arg Gly Ala Leu Leu Arg Ala Gly
            35                  40                  45

Pro Val Leu Pro Pro Gly Arg Arg Gly Leu Cys Val Arg Arg Pro
        50                  55                  60

Ser Gly Gly Ser Ser Gly Gly Ala Ala Ser Gly Ala Gly Pro Gly Thr
65                  70                  75                  80

Gln Gln Gly Ser Pro Gly Trp Ser Gln Ala Gly Ala Asp Gly Ala Ala
                85                  90                  95

Tyr Thr Pro Pro Pro Val Ser Pro Arg Phe Ser Phe Pro Gly Thr Thr
                100                 105                 110

Gly Ser Leu Ala Ala Ala Ala Ala Ala Ala Arg Glu Ala Ala Ala
            115                 120                 125

Tyr Ser Ser Gly Gly Gly Ala Ala Gly Ala Gly Leu Ala Gly Arg Glu
130                 135                 140

Gln Tyr Gly Arg Ala Ala Phe Ala Gly Ser Tyr Ser Ser Pro Tyr Pro
145                 150                 155                 160

Ala Tyr Met Ala Asp Val Gly Ala Ser Trp Ala Ala Ala Ala Ala
                165                 170                 175

Ser Ala Gly Pro Phe Asp Ser Pro Val Leu His Ser Leu Pro Gly Arg
            180                 185                 190

Ala Asn Pro Gly Ala Arg His Pro Asn Leu Asp Met Phe Asp Asp Phe
            195                 200                 205

Ser Glu Gly Arg Glu Cys Val Asn Cys Gly Ala Met Ser Thr Pro Leu
            210                 215                 220

Trp Arg Arg Asp Gly Thr Gly His Tyr Leu Cys Asn Ala Cys Gly Leu
225                 230                 235                 240

Tyr His Lys Met Asn Gly Ile Asn Arg Pro Leu Ile Lys Pro Gln Arg
                245                 250                 255

Arg Leu Ser Ala Ser Arg Arg Val Gly Leu Ser Cys Ala Asn Cys Gln
            260                 265                 270

Thr Thr Thr Thr Thr Leu Trp Arg Arg Asn Ala Glu Gly Glu Pro Val
            275                 280                 285

Cys Asn Ala Cys Gly Leu Tyr Met Lys Leu His Gly Val Pro Arg Pro
290                 295                 300

Leu Ala Met Arg Lys Glu Gly Ile Gln Thr Arg Lys Arg Lys Pro Lys
305                 310                 315                 320

Asn Leu Asn Lys Ser Lys Thr Pro Ala Ala Pro Ser Gly Ser Glu Ser
                325                 330                 335

Leu Pro Pro Ala Ser Gly Ala Ser Asn Ser Ser Asn Ala Thr Thr
            340                 345                 350

Ser Ser Ser Glu Glu Met Arg Pro Ile Lys Thr Glu Pro Gly Leu Ser
                355                 360                 365

Ser His Tyr Gly His Ser Ser Val Ser Gln Thr Phe Ser Val Ser
            370                 375                 380

Ala Met Ser Gly His Gly Pro Ser Ile His Pro Val Leu Ser Ala Leu
385                 390                 395                 400

Lys Leu Ser Pro Gln Gly Tyr Ala Ser Pro Val Ser Gln Ser Pro Gln
```

```
                    405                 410                 415
Thr Ser Ser Lys Gln Asp Ser Trp Asn Ser Leu Val Leu Ala Asp Ser
            420                 425                 430

His Gly Asp Ile Ile Thr Ala
            435

<210> SEQ ID NO 38
<211> LENGTH: 397
<212> TYPE: PRT
<213> ORGANISM: Homo sapiens

<400> SEQUENCE: 38

Met Tyr Gln Ser Leu Ala Leu Ala Ala Ser Pro Arg Gln Ala Ala Tyr
1               5                   10                  15

Ala Asp Ser Gly Ser Phe Leu His Ala Pro Gly Ala Gly Ser Pro Met
            20                  25                  30

Phe Val Pro Pro Ala Arg Val Pro Ser Met Leu Ser Tyr Leu Ser Gly
            35                  40                  45

Cys Glu Pro Ser Pro Gln Pro Pro Glu Leu Ala Ala Arg Pro Gly Trp
        50                  55                  60

Ala Gln Thr Ala Thr Ala Asp Ser Ser Ala Phe Gly Pro Gly Ser Pro
65                  70                  75                  80

His Pro Pro Ala Ala His Pro Pro Gly Ala Thr Ala Phe Pro Phe Ala
                85                  90                  95

His Ser Pro Ser Gly Pro Gly Ser Gly Gly Ser Ala Gly Gly Arg Asp
            100                 105                 110

Gly Ser Ala Tyr Gln Gly Ala Leu Leu Pro Arg Glu Gln Phe Ala Ala
            115                 120                 125

Pro Leu Gly Arg Pro Val Gly Thr Ser Tyr Ser Ala Thr Tyr Pro Ala
130                 135                 140

Tyr Val Ser Pro Asp Val Ala Gln Ser Trp Thr Ala Gly Pro Phe Asp
145                 150                 155                 160

Gly Ser Val Leu His Gly Leu Pro Gly Arg Arg Pro Thr Phe Val Ser
                165                 170                 175

Asp Phe Leu Glu Glu Phe Pro Gly Glu Gly Arg Glu Cys Val Asn Cys
            180                 185                 190

Gly Ala Leu Ser Thr Pro Leu Trp Arg Arg Asp Gly Thr Gly His Tyr
            195                 200                 205

Leu Cys Asn Ala Cys Gly Leu Tyr His Lys Met Asn Gly Val Asn Arg
        210                 215                 220

Pro Leu Val Arg Pro Gln Lys Arg Leu Ser Ser Arg Arg Ala Gly
225                 230                 235                 240

Leu Cys Cys Thr Asn Cys His Thr Thr Asn Thr Thr Leu Trp Arg Arg
                245                 250                 255

Asn Ser Glu Gly Glu Pro Val Cys Asn Ala Cys Gly Leu Tyr Met Lys
            260                 265                 270

Leu His Gly Val Pro Arg Pro Leu Ala Met Lys Lys Glu Ser Ile Gln
            275                 280                 285

Thr Arg Lys Arg Lys Pro Lys Thr Ile Ala Lys Ala Arg Gly Ser Ser
        290                 295                 300

Gly Ser Thr Arg Asn Ala Ser Ala Ser Pro Ser Ala Val Ala Ser Thr
305                 310                 315                 320

Asp Ser Ser Ala Ala Thr Ser Lys Ala Lys Pro Ser Leu Ala Ser Pro
                325                 330                 335
```

```
Val Cys Pro Gly Pro Ser Met Ala Pro Gln Ala Ser Gly Gln Glu Asp
            340                 345                 350

Asp Ser Leu Ala Pro Gly His Leu Glu Phe Lys Phe Glu Pro Glu Asp
        355                 360                 365

Phe Ala Phe Pro Ser Thr Ala Pro Ser Pro Gln Ala Gly Leu Arg Gly
    370                 375                 380

Ala Leu Arg Gln Glu Ala Trp Cys Ala Leu Ala Leu Ala
385                 390                 395

<210> SEQ ID NO 39
<211> LENGTH: 182
<212> TYPE: PRT
<213> ORGANISM: Homo sapiens

<400> SEQUENCE: 39

Leu Trp Lys Arg Phe His Glu Ile Gly Thr Glu Met Ile Ile Thr Lys
1               5                   10                  15

Ala Gly Arg Arg Met Phe Pro Ala Met Arg Val Lys Ile Ser Gly Leu
            20                  25                  30

Asp Pro His Gln Gln Tyr Tyr Ile Ala Met Asp Ile Val Pro Val Asp
        35                  40                  45

Asn Lys Arg Tyr Arg Tyr Val Tyr His Ser Ser Lys Trp Met Val Ala
    50                  55                  60

Gly Asn Ala Asp Ser Pro Val Pro Pro Arg Val Tyr Ile His Pro Asp
65                  70                  75                  80

Ser Pro Ala Ser Gly Glu Thr Trp Met Arg Gln Val Ile Ser Phe Asp
                85                  90                  95

Lys Leu Lys Leu Thr Asn Asn Glu Leu Asp Asp Gln Gly His Ile Ile
            100                 105                 110

Leu His Ser Met His Lys Tyr Gln Pro Arg Val His Val Ile Arg Lys
        115                 120                 125

Asp Cys Gly Asp Asp Leu Ser Pro Ile Lys Pro Val Pro Ser Gly Glu
    130                 135                 140

Gly Val Lys Ala Phe Ser Phe Pro Glu Thr Val Phe Thr Thr Val Thr
145                 150                 155                 160

Ala Tyr Gln Asn Gln Gln Ile Thr Arg Leu Lys Ile Asp Arg Asn Pro
                165                 170                 175

Phe Ala Lys Gly Phe Arg
            180

<210> SEQ ID NO 40
<211> LENGTH: 518
<212> TYPE: PRT
<213> ORGANISM: Homo sapiens

<400> SEQUENCE: 40

Met Ala Asp Ala Asp Glu Gly Phe Gly Leu Ala His Thr Pro Leu Glu
1               5                   10                  15

Pro Asp Ala Lys Asp Leu Pro Cys Asp Ser Lys Pro Glu Ser Ala Leu
            20                  25                  30

Gly Ala Pro Ser Lys Ser Pro Ser Pro Gln Ala Ala Phe Thr Gln
        35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80
```

-continued

```
Arg Arg Met Phe Pro Ser Tyr Lys Val Lys Val Thr Gly Leu Asn Pro
                85                  90                  95
Lys Thr Lys Tyr Ile Leu Leu Met Asp Ile Val Pro Ala Asp Asp His
            100                 105                 110
Arg Tyr Lys Phe Ala Asp Asn Lys Trp Ser Val Thr Gly Lys Ala Glu
            115                 120                 125
Pro Ala Met Pro Gly Arg Leu Tyr Val His Pro Asp Ser Pro Ala Thr
            130                 135                 140
Gly Ala His Trp Met Arg Gln Leu Val Ser Phe Gln Lys Leu Lys Leu
145                 150                 155                 160
Thr Asn Asn His Leu Asp Pro Phe Gly His Ile Ile Leu Asn Ser Met
                165                 170                 175
His Lys Tyr Gln Pro Arg Leu His Ile Val Lys Ala Asp Glu Asn Asn
            180                 185                 190
Gly Phe Gly Ser Lys Asn Thr Ala Phe Cys Thr His Val Phe Pro Glu
            195                 200                 205
Thr Ala Phe Ile Ala Val Thr Ser Tyr Gln Asn His Lys Ile Thr Gln
            210                 215                 220
Leu Lys Ile Glu Asn Asn Pro Phe Ala Lys Gly Phe Arg Gly Ser Asp
225                 230                 235                 240
Asp Met Glu Leu His Arg Met Ser Arg Met Gln Ser Lys Glu Tyr Pro
                245                 250                 255
Val Val Pro Arg Ser Thr Val Arg Gln Lys Val Ala Ser Asn His Ser
            260                 265                 270
Pro Phe Ser Ser Glu Ser Arg Ala Leu Ser Thr Ser Ser Asn Leu Gly
            275                 280                 285
Ser Gln Tyr Gln Cys Glu Asn Gly Val Ser Gly Pro Ser Gln Asp Leu
            290                 295                 300
Leu Pro Pro Pro Asn Pro Tyr Pro Leu Pro Gln Glu His Ser Gln Ile
305                 310                 315                 320
Tyr His Cys Thr Lys Arg Lys Glu Glu Glu Cys Ser Thr Thr Asp His
                325                 330                 335
Pro Tyr Lys Lys Pro Tyr Met Glu Thr Ser Pro Ser Glu Glu Asp Ser
            340                 345                 350
Phe Tyr Arg Ser Ser Tyr Pro Gln Gln Gln Gly Leu Gly Ala Ser Tyr
            355                 360                 365
Arg Thr Glu Ser Ala Gln Arg Gln Ala Cys Met Tyr Ala Ser Ser Ala
            370                 375                 380
Pro Pro Ser Glu Pro Val Pro Ser Leu Glu Asp Ile Ser Cys Asn Thr
385                 390                 395                 400
Trp Pro Ser Met Pro Ser Tyr Ser Ser Cys Thr Val Thr Thr Val Gln
                405                 410                 415
Pro Met Asp Arg Leu Pro Tyr Gln His Phe Ser Ala His Phe Thr Ser
            420                 425                 430
Gly Pro Leu Val Pro Arg Leu Ala Gly Met Ala Asn His Gly Ser Pro
            435                 440                 445
Gln Leu Gly Glu Gly Met Phe Gln His Gln Thr Ser Val Ala His Gln
            450                 455                 460
Pro Val Val Arg Gln Cys Gly Pro Gln Thr Gly Leu Gln Ser Pro Gly
465                 470                 475                 480
Thr Leu Gln Pro Pro Glu Phe Leu Tyr Ser His Gly Val Pro Arg Thr
                485                 490                 495
Leu Ser Pro His Gln Tyr His Ser Val His Gly Val Gly Met Val Pro
```

```
                        500                 505                 510
Glu Trp Ser Asp Asn Ser
            515

<210> SEQ ID NO 41
<211> LENGTH: 497
<212> TYPE: PRT
<213> ORGANISM: Homo sapiens

<400> SEQUENCE: 41

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly His Ser Thr
305                 310                 315                 320

Gly Tyr Glu Ser Asp Asn His Thr Thr Pro Ile Leu Cys Gly Ala Gln
                325                 330                 335

Tyr Arg Ile His Thr His Gly Val Phe Arg Gly Ile Gln Asp Val Arg
            340                 345                 350
```

Arg Val Pro Gly Val Ala Pro Thr Leu Val Arg Ser Ala Ser Glu Thr
            355                 360                 365

Ser Glu Lys Arg Pro Phe Met Cys Ala Tyr Pro Gly Cys Asn Lys Arg
    370                 375                 380

Tyr Phe Lys Leu Ser His Leu Gln Met His Ser Arg Lys His Thr Gly
385                 390                 395                 400

Glu Lys Pro Tyr Gln Cys Asp Phe Lys Asp Cys Glu Arg Arg Phe Ser
                405                 410                 415

Arg Ser Asp Gln Leu Lys Arg His Gln Arg Arg His Thr Gly Val Lys
                420                 425                 430

Pro Phe Gln Cys Lys Thr Cys Gln Arg Lys Phe Ser Arg Ser Asp His
            435                 440                 445

Leu Lys Thr His Thr Arg Thr His Thr Gly Glu Lys Pro Phe Ser Cys
450                 455                 460

Arg Trp Pro Ser Cys Gln Lys Lys Phe Ala Arg Ser Asp Glu Leu Val
465                 470                 475                 480

Arg His His Asn Met His Gln Arg Asn Met Thr Lys Leu Gln Leu Ala
                485                 490                 495

Leu

<210> SEQ ID NO 42
<211> LENGTH: 349
<212> TYPE: PRT
<213> ORGANISM: Homo sapiens

<400> SEQUENCE: 42

Met Gly Asp Met Gly Asp Pro Pro Lys Lys Lys Arg Leu Ile Ser Leu
1               5                   10                  15

Cys Val Gly Cys Gly Asn Gln Ile His Asp Gln Tyr Ile Leu Arg Val
            20                  25                  30

Ser Pro Asp Leu Glu Trp His Ala Ala Cys Leu Lys Cys Ala Glu Cys
        35                  40                  45

Asn Gln Tyr Leu Asp Glu Ser Cys Thr Cys Phe Val Arg Asp Gly Lys
    50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125

Cys Arg Ala Asp His Asp Val Val Glu Arg Ala Ser Leu Gly Ala Gly
    130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
                165                 170                 175

Gln Pro Glu Lys Thr Thr Arg Val Arg Thr Val Leu Asn Glu Lys Gln
            180                 185                 190

Leu His Thr Leu Arg Thr Cys Tyr Ala Ala Asn Pro Arg Pro Asp Ala
        195                 200                 205

Leu Met Lys Glu Gln Leu Val Glu Met Thr Gly Leu Ser Pro Arg Val
    210                 215                 220

```
Ile Arg Val Trp Phe Gln Asn Lys Arg Cys Lys Asp Lys Lys Arg Ser
225                 230                 235                 240

Ile Met Met Lys Gln Leu Gln Gln Gln Pro Asn Asp Lys Thr Asn
        245                 250                 255

Ile Gln Gly Met Thr Gly Thr Pro Met Val Ala Ala Ser Pro Glu Arg
            260                 265                 270

His Asp Gly Gly Leu Gln Ala Asn Pro Val Glu Val Gln Ser Tyr Gln
        275                 280                 285

Pro Pro Trp Lys Val Leu Ser Asp Phe Ala Leu Gln Ser Asp Ile Asp
        290                 295                 300

Gln Pro Ala Phe Gln Gln Leu Val Asn Phe Ser Glu Gly Gly Pro Gly
305                 310                 315                 320

Ser Asn Ser Thr Gly Ser Glu Val Ala Ser Met Ser Ser Gln Leu Pro
            325                 330                 335

Asp Thr Pro Asn Ser Met Val Ala Ser Pro Ile Glu Ala
            340                 345
```

<210> SEQ ID NO 43
<211> LENGTH: 473
<212> TYPE: PRT
<213> ORGANISM: Homo sapiens

<400> SEQUENCE: 43

```
Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
                20                  25                  30

Tyr Glu Leu Ser Val Leu Cys Asp Cys Glu Ile Ala Leu Ile Ile Phe
            35                  40                  45

Asn Ser Thr Asn Lys Leu Phe Gln Tyr Ala Ser Thr Asp Met Asp Lys
        50                  55                  60

Val Leu Leu Lys Tyr Thr Glu Tyr Asn Glu Pro His Glu Ser Arg Thr
65                  70                  75                  80

Asn Ser Asp Ile Val Glu Thr Leu Arg Lys Lys Gly Leu Asn Gly Cys
                85                  90                  95

Asp Ser Pro Asp Pro Asp Ala Asp Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Pro Asn Phe Glu Met Pro
130                 135                 140

Val Ser Ile Pro Val Ser Ser His Asn Ser Leu Val Tyr Ser Asn Pro
145                 150                 155                 160

Val Ser Ser Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190

Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Met Gln Ala Lys Ser
225                 230                 235                 240

Pro Pro Pro Met Asn Leu Gly Met Asn Asn Arg Lys Pro Asp Leu Arg
                245                 250                 255
```

-continued

Val Leu Ile Pro Pro Gly Ser Lys Asn Thr Met Pro Ser Val Ser Glu
             260                 265                 270

Asp Val Asp Leu Leu Asn Gln Arg Ile Asn Asn Ser Gln Ser Ala
         275                 280                 285

Gln Ser Leu Ala Thr Pro Val Val Ser Val Ala Thr Pro Thr Leu Pro
    290                 295                 300

Gly Gln Gly Met Gly Gly Tyr Pro Ser Ala Ile Ser Thr Thr Tyr Gly
305                 310                 315                 320

Thr Glu Tyr Ser Leu Ser Ser Ala Asp Leu Ser Ser Leu Ser Gly Phe
                325                 330                 335

Asn Thr Ala Ser Ala Leu His Leu Gly Ser Val Thr Gly Trp Gln Gln
             340                 345                 350

Gln His Leu His Asn Met Pro Pro Ser Ala Leu Ser Gln Leu Gly Ala
    355                 360                 365

Cys Thr Ser Thr His Leu Ser Gln Ser Ser Asn Leu Ser Leu Pro Ser
370                 375                 380

Thr Gln Ser Leu Asn Ile Lys Ser Glu Pro Val Ser Pro Pro Arg Asp
385                 390                 395                 400

Arg Thr Thr Thr Pro Ser Arg Tyr Pro Gln His Thr Arg His Glu Ala
                405                 410                 415

Gly Arg Ser Pro Val Asp Ser Leu Ser Ser Cys Ser Ser Ser Tyr Asp
             420                 425                 430

Gly Ser Asp Arg Glu Asp His Arg Asn Glu Phe His Ser Pro Ile Gly
         435                 440                 445

Leu Thr Arg Pro Ser Pro Asp Glu Arg Glu Ser Pro Ser Val Lys Arg
    450                 455                 460

Met Arg Leu Ser Glu Gly Trp Ala Thr
465                 470

<210> SEQ ID NO 44
<211> LENGTH: 463
<212> TYPE: PRT
<213> ORGANISM: Homo sapiens

<400> SEQUENCE: 44

Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Thr Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ser Asp Ile Val Glu Ala Leu Asn Lys Glu Asn Lys Gly Cys
             85                  90                  95

Glu Ser Pro Asp Pro Asp Ser Ser Tyr Ala Leu Thr Pro Arg Thr Glu
        100                 105                 110

Glu Lys Tyr Lys Lys Ile Asn Glu Glu Phe Asp Asn Met Ile Lys Ser
            115                 120                 125

His Lys Ile Pro Ala Val Pro Pro Asn Phe Glu Met Pro Val Ser
    130                 135                 140

Ile Pro Val Ser Ser His Asn Ser Leu Val Tyr Ser Asn Pro Val Ser

-continued

```
            145                 150                 155                 160
    Ser Leu Gly Asn Pro Asn Leu Leu Pro Leu Ala His Pro Ser Leu Gln
                    165                 170                 175

Arg Asn Ser Met Ser Pro Gly Val Thr His Arg Pro Pro Ser Ala Gly
                180                 185                 190

Asn Thr Gly Gly Leu Met Gly Gly Asp Leu Thr Ser Gly Ala Gly Thr
                    195                 200                 205

Ser Ala Gly Asn Gly Tyr Gly Asn Pro Arg Asn Ser Pro Gly Leu Leu
            210                 215                 220

Val Ser Pro Gly Asn Leu Asn Lys Asn Met Gln Ala Lys Ser Pro Pro
    225                 230                 235                 240

Pro Met Asn Leu Gly Met Asn Asn Arg Lys Pro Asp Leu Arg Val Leu
                    245                 250                 255

Ile Pro Pro Gly Ser Lys Asn Thr Met Pro Ser Val Asn Gln Arg Ile
                260                 265                 270

Asn Asn Ser Gln Ser Ala Gln Ser Leu Ala Thr Pro Val Val Ser Val
                    275                 280                 285

Ala Thr Pro Thr Leu Pro Gly Gln Gly Met Gly Gly Tyr Pro Ser Ala
            290                 295                 300

Ile Ser Thr Thr Tyr Gly Thr Glu Tyr Ser Leu Ser Ser Ala Asp Leu
    305                 310                 315                 320

Ser Ser Leu Ser Gly Phe Asn Thr Ala Ser Ala Leu His Leu Gly Ser
                    325                 330                 335

Val Thr Gly Trp Gln Gln Gln His Leu His Asn Met Pro Pro Ser Ala
                340                 345                 350

Leu Ser Gln Leu Gly Ala Cys Thr Ser Thr His Leu Ser Gln Ser Ser
            355                 360                 365

Asn Leu Ser Leu Pro Ser Thr Gln Ser Leu Asn Ile Lys Ser Glu Pro
                    370                 375                 380

Val Ser Pro Pro Arg Asp Arg Thr Thr Thr Pro Ser Arg Tyr Pro Gln
    385                 390                 395                 400

His Thr Arg His Glu Ala Gly Arg Ser Pro Val Asp Ser Leu Ser Ser
                    405                 410                 415

Cys Ser Ser Ser Tyr Asp Gly Ser Asp Arg Glu Asp His Arg Asn Glu
                420                 425                 430

Phe His Ser Pro Ile Gly Leu Thr Arg Pro Ser Pro Asp Glu Arg Glu
            435                 440                 445

Ser Pro Ser Val Lys Arg Met Arg Leu Ser Glu Gly Trp Ala Thr
                    450                 455                 460

<210> SEQ ID NO 45
<211> LENGTH: 938
<212> TYPE: PRT
<213> ORGANISM: Homo sapiens

<400> SEQUENCE: 45

Met Thr Leu Leu Gly Ser Glu His Ser Leu Leu Ile Arg Ser Lys Phe
    1               5                   10                  15

Arg Ser Val Leu Gln Leu Arg Leu Gln Gln Arg Arg Thr Gln Glu Gln
                    20                  25                  30

Leu Ala Asn Gln Gly Ile Ile Pro Pro Leu Lys Arg Pro Ala Glu Phe
                35                  40                  45

His Glu Gln Arg Lys His Leu Asp Ser Asp Lys Ala Lys Asn Ser Leu
            50                  55                  60
```

-continued

```
Lys Arg Lys Ala Arg Asn Arg Cys Asn Ser Ala Asp Leu Val Asn Met
 65                  70                  75                  80

His Ile Leu Gln Ala Ser Thr Ala Glu Arg Ser Ile Pro Thr Ala Gln
                 85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
        195                 200                 205

Asp Ser Ala Ser Gln Pro Ser His Gln Ser Asp Ala Gly Lys Gln Gly
210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
            260                 265                 270

Gln Lys Ala Glu Lys Ser Pro Pro Met Asp Ser Ala Tyr Ala Arg
        275                 280                 285

Leu Leu Gln Gln Gln Gln Leu Phe Leu Gln Leu Gln Ile Leu Ser Gln
290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335

Ser Ser Thr Pro Leu Ser Asn Thr Pro Leu Ser Pro Val Lys Asn Ser
            340                 345                 350

Phe Ser Gly Gln Thr Gly Val Ser Ser Phe Lys Pro Gly Pro Leu Pro
        355                 360                 365

Pro Asn Leu Asp Asp Leu Lys Val Ser Glu Leu Arg Gln Gln Leu Arg
370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                405                 410                 415

Asp Ile Thr Thr Val Thr Phe Pro Val Thr Pro Asn Thr Leu Pro Asn
            420                 425                 430

Tyr Gln Ser Ser Ser Ser Thr Ser Ala Leu Ser Asn Gly Phe Tyr His
        435                 440                 445

Phe Gly Ser Thr Ser Ser Pro Pro Ile Ser Pro Ala Ser Ser Asp
450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
```

```
                    485              490              495
Leu Met Ser Ser Leu Asn Gly Gly Ser Val Pro Ser Glu Leu Asp Gly
                500              505              510
Leu Asp Ser Glu Lys Asp Lys Met Leu Val Glu Lys Gln Lys Val Ile
            515              520              525
Asn Glu Leu Thr Trp Lys Leu Gln Gln Glu Gln Arg Gln Val Glu Glu
        530              535              540
Leu Arg Met Gln Leu Gln Lys Gln Lys Arg Asn Asn Cys Ser Glu Lys
545              550              555              560
Lys Pro Leu Pro Phe Leu Ala Ala Ser Ile Lys Gln Glu Glu Ala Val
                565              570              575
Ser Ser Cys Pro Phe Ala Ser Gln Val Pro Val Lys Arg Gln Ser Ser
            580              585              590
Ser Ser Glu Cys His Pro Pro Ala Cys Glu Ala Ala Gln Leu Gln Pro
        595              600              605
Leu Gly Asn Ala His Cys Val Glu Ser Ser Asp Gln Thr Asn Val Leu
    610              615              620
Ser Ser Thr Phe Leu Ser Pro Gln Cys Ser Pro Gln His Ser Pro Leu
625              630              635              640
Gly Ala Val Lys Ser Pro Gln His Ile Ser Leu Pro Pro Ser Pro Asn
                645              650              655
Asn Pro His Phe Leu Pro Ser Ser Gly Ala Gln Gly Glu Gly His
            660              665              670
Arg Val Ser Ser Pro Ile Ser Ser Gln Val Cys Thr Ala Gln Met Ala
        675              680              685
Gly Leu His Ser Ser Asp Lys Val Gly Pro Lys Phe Ser Ile Pro Ser
    690              695              700
Pro Thr Phe Ser Lys Ser Ser Ala Ile Ser Glu Val Thr Gln Pro
705              710              715              720
Pro Ser Tyr Glu Asp Ala Val Lys Gln Gln Met Thr Arg Ser Gln Gln
                725              730              735
Met Asp Glu Leu Leu Asp Val Leu Ile Glu Ser Gly Glu Met Pro Ala
            740              745              750
Asp Ala Arg Glu Asp His Ser Cys Leu Gln Lys Val Pro Lys Ile Pro
        755              760              765
Arg Ser Ser Arg Ser Pro Thr Ala Val Leu Thr Lys Pro Ser Ala Ser
    770              775              780
Phe Glu Gln Ala Ser Ser Gly Ser Gln Ile Pro Phe Asp Pro Tyr Ala
785              790              795              800
Thr Asp Ser Asp Glu His Leu Glu Val Leu Leu Asn Ser Gln Ser Pro
                805              810              815
Leu Gly Lys Met Ser Asp Val Thr Leu Leu Lys Ile Gly Ser Glu Glu
            820              825              830
Pro His Phe Asp Gly Ile Met Asp Gly Phe Ser Gly Lys Ala Ala Glu
        835              840              845
Asp Leu Phe Asn Ala His Glu Ile Leu Pro Gly Pro Leu Ser Pro Met
    850              855              860
Gln Thr Gln Phe Ser Pro Ser Ser Val Asp Ser Asn Gly Leu Gln Leu
865              870              875              880
Ser Phe Thr Glu Ser Pro Trp Glu Thr Met Glu Trp Leu Asp Leu Thr
                885              890              895
Pro Pro Asn Ser Thr Pro Gly Phe Ser Ala Leu Thr Thr Ser Ser Pro
            900              905              910
```

```
Ser Ile Phe Asn Ile Asp Phe Leu Asp Val Thr Asp Leu Asn Leu Asn
        915                 920                 925

Ser Ser Met Asp Leu His Leu Gln Gln Trp
    930                 935
```